(12) United States Patent
Fay et al.

(10) Patent No.: US 8,338,571 B2
(45) Date of Patent: Dec. 25, 2012

(54) RECOMBINANT FACTOR VIII HAVING INCREASED STABILITY

(75) Inventors: Philip J. Fay, Pittsford, NY (US); Hironao Wakabayashi, Rochester, NY (US)

(73) Assignee: University of Rochester, Rochester, NY (US)

( * ) Notice: Subject to any disclaimer, the term of this patent is extended or adjusted under 35 U.S.C. 154(b) by 504 days.

(21) Appl. No.: 12/179,801

(22) Filed: Jul. 25, 2008

(65) Prior Publication Data

US 2009/0118184 A1 May 7, 2009

Related U.S. Application Data

(60) Provisional application No. 60/984,518, filed on Nov. 1, 2007, provisional application No. 60/991,304, filed on Nov. 30, 2007.

(51) Int. Cl.
*A61K 38/37* (2006.01)
*C07K 14/755* (2006.01)
(52) U.S. Cl. ........................ 530/383; 514/14.1
(58) Field of Classification Search .................. None
See application file for complete search history.

(56) References Cited

U.S. PATENT DOCUMENTS

| | | | |
|---|---|---|---|
| 5,576,291 | A | 11/1996 | Curtis et al. |
| 5,859,204 | A | 1/1999 | Lollar |
| 5,880,327 | A | 3/1999 | Lubon et al. |
| 5,998,589 | A | 12/1999 | Buettner et al. |
| 6,271,025 | B1 | 8/2001 | Négrier et al. |
| 6,376,463 | B1 | 4/2002 | Lollar |
| 6,458,563 | B1 | 10/2002 | Lollar |
| 6,593,291 | B1 | 7/2003 | Green et al. |
| 6,599,724 | B1 | 7/2003 | Mikaelsson et al. |
| 6,759,216 | B1 | 7/2004 | Lollar |
| 6,770,744 | B2 | 8/2004 | Lollar |
| 6,780,614 | B2 | 8/2004 | Négrier et al. |
| 6,800,461 | B2 | 10/2004 | Négrier et al. |
| 7,205,278 | B2 | 4/2007 | Griffin et al. |
| 2003/0125232 | A1 | 7/2003 | Griffin et al. |
| 2003/0166536 | A1 | 9/2003 | Lollar |
| 2004/0092442 | A1 | 5/2004 | Kaufman et al. |
| 2004/0147436 | A1 | 7/2004 | Kim et al. |
| 2004/0197815 | A1 | 10/2004 | Singh et al. |
| 2006/0293238 | A1 | 12/2006 | Kaufman et al. |
| 2007/0265199 | A1 | 11/2007 | Fay et al. |

FOREIGN PATENT DOCUMENTS

WO    2005/055930 A2    6/2005

OTHER PUBLICATIONS

Pemberton, S., et al. 1997 Blood 89(7): 2413-2421.*
Sammond, D.W., et al. 2007 J. Mol. Biol. 371: 1392-1404.*
Sergel, T.A., et al. 2000 Journal of Virology 74(11): 5101-5107.*
Yuan, S-M., et al. 1998 Proteins: Structure, Function, Genetics 30: 136-143.*
Hakeos et al., "Hemophilia A Mutations Within the Factor VIII A2-A3 Subunit Interface Destabilize Factor VIIIa and Cause One-stage/Two-stage Activity Discrepancy," Thromb Haemost 88:781-7 (2002).
International Search Report for International Patent Application No. PCT/US08/71170 (Nov. 21, 2008).
Amano et al., "Mutation at either Arg336 or Arg562 in Factor VIII is Insufficient for Complete Resistance to Activated Protein C (APC)-Mediated Inactivation: Implications for the APC Resistance Test," Thromb Haemost 79:557-563 (1998).
Gale et al., "An Engineered Interdomain Disulfide Bond Stabilizes Human Blood Coagulation Factor VIIIa," J Thrombosis and Haemostasis 1(9):1966-1971 (2003) (abstract only).
Hernández (editor), "Factor VIII/von Willebrand Factor Complex in Hemophilia A Treatment: Recent Findings, Emerging Major Role," Journal of Hematology 88(9):1-27 (2003).
Lenting et al., "The Life Cycle of Coagulation Factor VIII in View of Its Structure and Function," Blood 92 (11):3983-3996 (1998).
Lenting et al., "The Sequence of Glu1811-Lys1818 of Human Blood Coagulation Factor VIII Comprises a Binding Site for Activated Factor IX," J Biol Chem 271(4):1935-1940 (1996).
Pipe et al., "Characterization of a Genetically Engineered Inactivation-Resistant Coagulation Factor VIIIa," Proc Natl Acad Sci USA 94:11851-11856 (1997).
Sarafanov et al., "Cell Surface Heparan Sulfate Proteoglycans Participate in Factor VIII Catabolism Mediated by Low Density Lipoprotein Receptor-Related Protein," J Biol Chem 276(15):11970-11979 (2001).
Swaroop et al., "Mutagenesis of a Potential Immunoglobulin-Binding Protein-Binding Site Enhances Secretion of Coagulation Factor VIII," J Biol Chem 272(39):24121-24124 (1997).
Wakabayahi et al., "Factor VIII: E113A Represents a High Specific Activity Factor VIII Arising From a Single Point Mutation within the Ca2+ Binding Site," Blood 104(11):479a Abstract 1735 (2004).
Wakabayashi et al., "Residues 110-126 in the A1 Domain of Factor VIII Contain a Ca2+ Binding Site Required for Cofactor Activity," J Biol Chem 279(13):12677-12684 (2004).
Wakabayashi et al., "Residues 110-126 in the Factor VIII Heavy Chain Contain a CA2+ Binding Site Required for Cofactor Activity," Blood 102(11):542a Abstract 1988 (2003).
Wakabayashi et al., "Ca2+ Binding to Both the HEavy and Light Chains of Factor VIII Is Required for Cofactor Activity," Biochem 41:8485-8492 (2002).
Wakabayashi et al., "Identification of Residues Contributing to A2 Domain-Dependent Structural Stability in Factor VIII and Factor VIIIa," J Biol. Chem. 283:11645-11651 (2008).

* cited by examiner

*Primary Examiner* — Marsha Tsay
(74) *Attorney, Agent, or Firm* — LeClairRyan, a Professional Corporation

(57) ABSTRACT

The present invention relates to a recombinant factor VIII that includes one or more mutations that result in enhanced stability of both factor VIII and factor VIIIa. Methods of making and using the recombinant factor VIII, and pharmaceutical compositions containing the same are also disclosed. The present invention further relates to an isolated nucleic acid molecule that encodes the recombinant factor VIII, as well as DNA expression systems and host cells containing the isolated nucleic acid molecule.

46 Claims, 21 Drawing Sheets

SEQUENCE LISTING

<160> NUMBER OF SEQ ID NOS: 2

<210> SEQ ID NO 1
<211> LENGTH: 6999
<212> TYPE: DNA
<213> ORGANISM: Homo sapiens

<400> SEQUENCE: 1
gccaccagaa gatactacct gggtgcagtg gaactgtcat gggactatat gcaaagtgat      60
ctcggtgagc tgcctgtgga cgcaagattt cctcctagag tgccaaaatc ttttccattc     120

```
aacacctcag tcgtgtacaa aaagactctg tttgtagaat tcacggatca ccttttcaac      180
atcgctaagc caaggccacc ctggatgggt ctgctaggtc ctaccatcca ggctgaggtt      240
tatgatacag tggtcattac acttaagaac atggcttccc atcctgtcag tcttcatgct      300
gttggtgtat cctactggaa agcttctgag ggagctgaat atgatgatca gaccagtcaa      360
agggagaaag aagatgataa agtcttccct ggtggaagcc atacatatgt ctggcaggtc      420
ctgaaagaga atggtccaat ggcctctgac ccactgtgcc ttacctactc atatcttcct      480
catgtggacc tggtaaaaga cttgaattca ggcctcattg gagccctact agtatgtaga      540
gaagggagtc tggccaagga aaagacacag accttgcaca aatttatact acttttgct       600 gtatttgatg aagggaaaag ttggcactca gaaacaaaga actccttgat gcaggatagg      660
gatgctgcat ctgctcgggc ctggcctaaa atgcacacag tcaatggtta tgtaaacagg      720
tctctgccag gtctgattgg atgccacagg aaatcagtct attggcatgt gattggaatg      780
ggcaccactc ctgaagtgca ctcaatattc ctcgaaggtc acacatttct tgtgaggaac      840
catcgccagg cgtccttgga aatctcgcca ataactttcc ttactgctca aacactcttg      900
atggaccttg gacagtttct actgttttgt catatctctt cccaccaaca tgatggcatg      960
gaagcttatg tcaaagtaga cagctgtcca gaggaacccc aactacgaat gaaaaataat     1020
gaagaagcgg aagactatga tgatgatctt actgattctg aaatggatgt ggtcaggttt     1080
gatgatgaca actctccttc ctttatccaa attcgctcag ttgccaagaa gcatcctaaa     1140
acttgggtac attacattgc tgctgaagag gaggactggg actatgctcc cttagtcctc     1200
gcccccgatg acagaagtta taaaagtcaa tatttgaaca atggccctca gcggattggt     1260
aggaagtaca aaaaagtccg atttatggca tacacagatg aaacctttaa gactcgtgaa     1320
gctattcagc atgaatcagg aatcttggga cctttacttt atggggaagt tggagacaca     1380
ctgttgatta tatttaagaa tcaagcaagc agaccatata acatctaccc tcacggaatc     1440
actgatgtcc gtcctttgta ttcaaggaga ttaccaaaag gtgtaaaaca tttgaaggat     1500
tttccaattc tgccaggaga aatattcaaa tataaatgga cagtgactgt agaagatggg     1560
ccaactaaat cagatcctcg gtgcctgacc cgctattact ctagtttcgt taatatggag     1620
agagatctag cttcaggact cattggcccct ctcctcatct gctacaaaga atctgtagat     1680
caaagaggaa accagataat gtcagacaag aggaatgtca cctgtttttc tgtatttgat     1740
gagaaccgaa gctggtacct cacagagaat atacaacgct ttctccccaa tccagctgga     1800
gtgcagcttg aggatccaga gttccaagcc tccaacatca tgcacagcat caatggctat     1860 gttttgata gtttgcagtt gtcagtttgt ttgcatgagg tggcatactg gtacattcta     1920
agcattggag cacagactga cttcctttct gtcttcttct ctggatatac cttcaaacac     1980
aaaatggtct atgaagacac actcacccta ttcccattct caggagaaac tgtcttcatg     2040
tcgatggaaa acccaggtct atggattctg gggtgccaca actcagactt tcggaacaga     2100
ggcatgaccg ccttactgaa ggtttctagt tgtgacaaga cactggtga ttattacgag      2160 gacagttatg aagatatttc agcatacttg ctgagtaaaa acaatgccat gaaccaaga      2220 agcttctccc agaattcaag acaccctagc actaggcaaa agcaatttaa tgccaccaca     2280
attccagaaa atgacataga gaagactgac ccttggtttg cacacagaac acctatgcct     2340
aaaatacaaa atgtctcctc tagtgatttg ttgatgctct tgcgacagag tcctactcca     2400
catgggctat ccttatctga tctccaagaa gccaaatatg agacttttc tgatgatcca     2460 tcacctggag caatagacag taataacagc ctgtctgaaa tgacacactt caggccacag     2520
```

```
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggacccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720 gacgggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag cttttgaaaca attcagactc    3960 ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctcccttta tcagattgcc ttacgaggag tcatagcatc    4140
cctcaagcaa atagatctcc attacccatt gcaaaggtat catcatttcc atctattaga    4200
cctatatatc tgaccaggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg tgatcaaag agaggttggc    4380 tccctgggga caagtgccac aaattcagtc acatacaaga aagttgagaa cactgttctc    4440
ccgaaaccag acttgcccaa acatctggcc aaagttgaat tgcttccaaa agttcacatt    4500
tatcagaagg acctattccc tacgaaaact agcaatgggt tcctggcca tctggatctc    4560 gtggaaggga gccttcttca gggaacagag ggagcgatta agtggaatga agcaaacaga    4620
cctgaaaaag ttcccttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gctttttaaga aaaaggatac cattttgtcc    4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
```

```
ccagtcttga aacgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag cccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa cttttcagaaa tcaggcctct    5340 cgtccctatt ccttctattc tagccttatt tcttatgagg aagatcagag gcaaggagca    5400
gaacctagaa aaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaaagatgt gcactcaggc ctgattggac cccttctggt ctgccacact    5580
aacacactga accctgctca tgggagacaa gtgacagtac aggaatttgc tctgtttttc    5640
accatctttg atgagaccaa aagctggtac ttcactgaaa atatggaaag aaactgcagg    5700
gctccctgca atatccagat ggaagatccc actttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaaatgg cactgtacaa tctctatcca    5940 ggtgttttg agacagtgga aatgttacca tccaaagctg gaatttggcg gtggaatgc    6000 cttattggcg agcatctaca tgctgggatg agcacacttt tctggtgta cagcaataag    6060 tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaaca caatattttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct ttttcagaa tggcaaagta    6840 aaggttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctactga                          6999
```

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

-continued

```
Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
        835                 840                 845
```

-continued

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
    995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Glu Gly Ala Tyr Ala Pro Val Leu
    1235                1240                1245

Gln Asp Phe Arg Ser Leu Asn Asp Ser Thr Asn Arg Thr Lys Lys
    1250                1255                1260

-continued

His Thr Ala His Phe Ser Lys Lys Gly Glu Glu Glu Asn Leu Glu
1265                1270            1275

Gly Leu Gly Asn Gln Thr Lys Gln Ile Val Glu Lys Tyr Ala Cys
1280                1285            1290

Thr Thr Arg Ile Ser Pro Asn Thr Ser Gln Gln Asn Phe Val Thr
1295                1300            1305

Gln Arg Ser Lys Arg Ala Leu Lys Gln Phe Arg Leu Pro Leu Glu
1310                1315            1320

Glu Thr Glu Leu Glu Lys Arg Ile Ile Val Asp Asp Thr Ser Thr
1325                1330            1335

Gln Trp Ser Lys Asn Met Lys His Leu Thr Pro Ser Thr Leu Thr
1340                1345            1350

Gln Ile Asp Tyr Asn Glu Lys Glu Lys Gly Ala Ile Thr Gln Ser
1355                1360            1365

Pro Leu Ser Asp Cys Leu Thr Arg Ser His Ser Ile Pro Gln Ala
1370                1375            1380

Asn Arg Ser Pro Leu Pro Ile Ala Lys Val Ser Ser Phe Pro Ser
1385                1390            1395

Ile Arg Pro Ile Tyr Leu Thr Arg Val Leu Phe Gln Asp Asn Ser
1400                1405            1410

Ser His Leu Pro Ala Ala Ser Tyr Arg Lys Lys Asp Ser Gly Val
1415                1420            1425

Gln Glu Ser Ser His Phe Leu Gln Gly Ala Lys Lys Asn Asn Leu
1430                1435            1440

Ser Leu Ala Ile Leu Thr Leu Glu Met Thr Gly Asp Gln Arg Glu
1445                1450            1455

Val Gly Ser Leu Gly Thr Ser Ala Thr Asn Ser Val Thr Tyr Lys
1460                1465            1470

Lys Val Glu Asn Thr Val Leu Pro Lys Pro Asp Leu Pro Lys Thr
1475                1480            1485

Ser Gly Lys Val Glu Leu Leu Pro Lys Val His Ile Tyr Gln Lys
1490                1495            1500

Asp Leu Phe Pro Thr Glu Thr Ser Asn Gly Ser Pro Gly His Leu
1505                1510            1515

Asp Leu Val Glu Gly Ser Leu Leu Gln Gly Thr Glu Gly Ala Ile
1520                1525            1530

Lys Trp Asn Glu Ala Asn Arg Pro Gly Lys Val Pro Phe Leu Arg
1535                1540            1545

Val Ala Thr Glu Ser Ser Ala Lys Thr Pro Ser Lys Leu Leu Asp
1550                1555            1560

Pro Leu Ala Trp Asp Asn His Tyr Gly Thr Gln Ile Pro Lys Glu
1565                1570            1575

Glu Trp Lys Ser Gln Glu Lys Ser Pro Glu Lys Thr Ala Phe Lys
1580                1585            1590

Lys Lys Asp Thr Ile Leu Ser Leu Asn Ala Cys Glu Ser Asn His
1595                1600            1605

Ala Ile Ala Ala Ile Asn Glu Gly Gln Asn Lys Pro Glu Ile Glu
1610                1615            1620

Val Thr Trp Ala Lys Gln Gly Arg Thr Glu Arg Leu Cys Ser Gln
1625                1630            1635

Asn Pro Pro Val Leu Lys Arg His Gln Arg Glu Ile Thr Arg Thr
1640                1645            1650

Thr Leu Gln Ser Asp Gln Glu Glu Ile Asp Tyr Asp Asp Thr Ile
1655                1660            1665

```
Ser Val Glu Met Lys Lys Glu Asp Phe Asp Ile Tyr Asp Glu Asp
    1670            1675                1680

Glu Asn Gln Ser Pro Arg Ser Phe Gln Lys Lys Thr Arg His Tyr
    1685            1690                1695

Phe Ile Ala Ala Val Glu Arg Leu Trp Asp Tyr Gly Met Ser Ser
    1700            1705                1710

Ser Pro His Val Leu Arg Asn Arg Ala Gln Ser Gly Ser Val Pro
    1715            1720                1725

Gln Phe Lys Lys Val Val Phe Gln Glu Phe Thr Asp Gly Ser Phe
    1730            1735                1740

Thr Gln Pro Leu Tyr Arg Gly Glu Leu Asn Glu His Leu Gly Leu
    1745            1750                1755

Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830

Ala Trp Ala Tyr Phe Ser Asp Val Asp Leu Glu Lys Asp Val His
    1835            1840                1845

Ser Gly Leu Ile Gly Pro Leu Leu Val Cys His Thr Asn Thr Leu
    1850            1855                1860

Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995

Glu Cys Leu Ile Gly Glu His Leu His Ala Gly Met Ser Thr Leu
    2000            2005                2010

Phe Leu Val Tyr Ser Asn Lys Cys Gln Thr Pro Leu Gly Met Ala
    2015            2020                2025

Ser Gly His Ile Arg Asp Phe Gln Ile Thr Ala Ser Gly Gln Tyr
    2030            2035                2040

Gly Gln Trp Ala Pro Lys Leu Ala Arg Leu His Tyr Ser Gly Ser
    2045            2050                2055

Ile Asn Ala Trp Ser Thr Lys Glu Pro Phe Ser Trp Ile Lys Val
    2060            2065                2070
```

-continued

```
Asp Leu Leu Ala Pro Met Ile Ile His Gly Ile Lys Thr Gln Gly
    2075                2080            2085

Ala Arg Gln Lys Phe Ser Ser Leu Tyr Ile Ser Gln Phe Ile Ile
    2090            2095                2100

Met Tyr Ser Leu Asp Gly Lys Lys Trp Gln Thr Tyr Arg Gly Asn
    2105            2110                2115

Ser Thr Gly Thr Leu Met Val Phe Phe Gly Asn Val Asp Ser Ser
    2120            2125                2130

Gly Ile Lys His Asn Ile Phe Asn Pro Pro Ile Ile Ala Arg Tyr
    2135            2140                2145

Ile Arg Leu His Pro Thr His Tyr Ser Ile Arg Ser Thr Leu Arg
    2150            2155                2160

Met Glu Leu Met Gly Cys Asp Leu Asn Ser Cys Ser Met Pro Leu
    2165            2170                2175

Gly Met Glu Ser Lys Ala Ile Ser Asp Ala Gln Ile Thr Ala Ser
    2180            2185                2190

Ser Tyr Phe Thr Asn Met Phe Ala Thr Trp Ser Pro Ser Lys Ala
    2195            2200                2205

Arg Leu His Leu Gln Gly Arg Ser Asn Ala Trp Arg Pro Gln Val
    2210            2215                2220

Asn Asn Pro Lys Glu Trp Leu Gln Val Asp Phe Gln Lys Thr Met
    2225            2230                2235

Lys Val Thr Gly Val Thr Thr Gln Gly Val Lys Ser Leu Leu Thr
    2240            2245                2250

Ser Met Tyr Val Lys Glu Phe Leu Ile Ser Ser Ser Gln Asp Gly
    2255            2260                2265

His Gln Trp Thr Leu Phe Phe Gln Asn Gly Lys Val Lys Val Phe
    2270            2275                2280

Gln Gly Asn Gln Asp Ser Phe Thr Pro Val Val Asn Ser Leu Asp
    2285            2290                2295

Pro Pro Leu Leu Thr Arg Tyr Leu Arg Ile His Pro Gln Ser Trp
    2300            2305                2310

Val His Gln Ile Ala Leu Arg Met Glu Val Leu Gly Cys Glu Ala
    2315            2320                2325

Gln Asp Leu Tyr
    2330
```

RECOMBINANT FACTOR VIII HAVING INCREASED STABILITY

Figure 1:
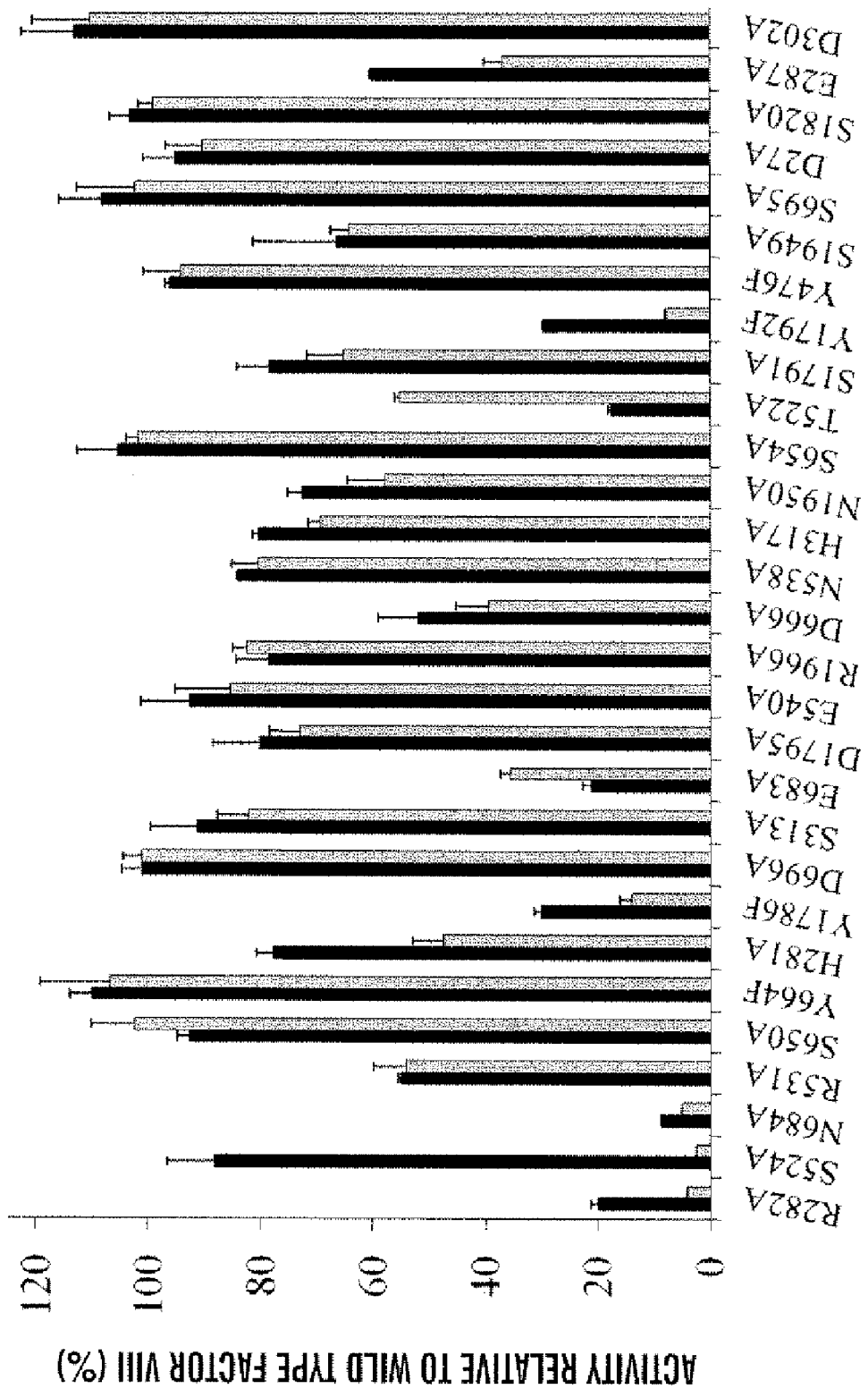

This application claims the priority benefit of U.S. Provisional Patent Application Ser. No. 60/984,518, filed Nov. 1, 2007, and U.S. Provisional Patent Application Ser. No. 60/991,304, filed Nov. 30, 2007, each of which is hereby incorporated by reference in its entirety.

This invention was made with government support under grant numbers HL 76213 and HL 38199 awarded by the National Institutes of Health. The government has certain rights in the invention.

BACKGROUND OF THE INVENTION

Hemophilia A, the most common of the severe, inherited bleeding disorders, results from a deficiency or defect in the plasma protein factor VIII. There is no cure for Hemophilia A and treatment consists of replacement therapy using preparations of (purified) plasma or the recombinant protein.

Factor VIII circulates as a non-covalent, metal ion-dependent heterodimer. This procofactor form of the protein contains a heavy chain (HC) comprised of A1(a1)A2(a2)B domains and a light chain (LC) comprised of (a3)A3C1C2 domains, with the lower case a representing short (~30-40 residue) segments rich in acidic residues (see Fay, "Activation of Factor VIII and Mechanisms of Cofactor Action," *Blood Rev.* 18:1-15 (2004)). Factor VIII is activated by proteolytic cleavages at the A1A2, A2B and A3A3 junctions catalyzed by thrombin or factor Xa. The product of this reaction, factor VIIIa, is a heterotrimer comprised of subunits designated A1, A2, and A3C1C2 that functions as a cofactor for the serine protease factor IXa in the membrane-dependent conversion of zymogen factor X to the serine protease, factor Xa (see Fay, "Activation of Factor VIII and Mechanisms of Cofactor Action," *Blood Rev.* 18:1-15 (2004)).

Reconstitution studies have shown that the factor VIII heterodimeric structure is supported by both electrostatic and hydrophobic interactions (Fay, "Reconstitution of Human Factor VIII from Isolated Subunits," *Arch Biochem Biophys.* 262:525-531 (1988); Ansong et al., "Factor VIII A1 Domain Residues 97-105 Represent a Light Chain-interactive Site," *Biochemistry.* 45:13140-13149 (2006), and the inter-chain affinity is further strengthened by factor VIII binding von Willebrand factor (Fay, "Reconstitution of Human Factor VIII from Isolated Subunits," *Arch Biochem Biophys.* 262:525-531 (1988); Kaufman et al., "Regulation of Factor VIII Expression and Activity by von Willebrand Factor," *Thromb Haemost.* 82:201-208 (1999)). Metal ions also contribute to the inter-chain affinity and activity parameters (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001)), Calcium is required to yield the active factor VIII conformation. Mutagenesis studies mapped a calcium-binding site to a segment rich in acidic residues within the A1 domain (residues 110-126) and identified specific residues within this region prominent in the coordination of the ion (Wakabayashi et al., "Residues 110-126 in the A1 Domain of Factor VIII Contain a $Ca^{2+}$ Binding Site Required for Cofactor Activity," *J Biol Chem.* 279:12677-12684 (2004)). A recent intermediate resolution X-ray structure (Shen et al., "The Tertiary Structure and Domain Organization of Coagulation Factor VIII," *Blood* 111:1240-1247 (2008)) confirmed this calcium-binding site as well as suggested a second potential site within the A2 domain. This structure also showed occupancy of the two type 1 copper ion sites within the A1 and A3 domains. Earlier functional studies have shown that copper ions facilitate the association of the heavy and light chains to form the heterodimer, increasing the inter-chain affinity by several-fold at physiologic pH (Fay et al., "Human Factor VIIIa Subunit Structure: Reconstruction of Factor VIIIa from the Isolated A1/A3-C1-C2 Dimer and A2 Subunit," *J Biol Chem.* 266:8957-8962 (1991); Wakabayashi et al., "pH-dependent Association of Factor VIII Chains: Enhancement of Affinity at Physiological pH by $Cu^{2+}$," *Biochim Biophys Acta.* 1764:1094-1101 (2006); Ansong et al., "Factor VIII A3 Domain Residues 1954-1961 Represent an A1 Domain-Interactive Site," *Biochemistry* 44:8850-8857 (2005)).

The instability of factor VIIIa results from weak electrostatic interactions between the A2 subunit and the A1/A3C1C2 dimer (Fay et al., "Human Factor VIIIa Subunit Structure: Reconstruction of Factor VIIIa from the Isolated A1/A3-C1-C2 Dimer and A2 Subunit," *J Biol Chem.* 266:8957-8962 (1991); Lollar et al., "pH-dependent Denaturation of Thrombin-activated Porcine Factor VIII," *J Biol Chem.* 265:1688-1692 (1990)) and leads to dampening of factor Xase activity (Lollar et al., "Coagulant Properties of Hybrid Human/Porcine Factor VIII Molecules," *J Biol Chem.* 267:23652-23657 (1992); Fay et al., "Model for the Factor VIIIa-dependent Decay of the Intrinsic Factor Xase: Role of Subunit Dissociation and Factor IXa-catalyzed Proteolysis," *J Biol Chem.* 271:6027-6032 (1996)). Limited information is available regarding the association of the AS subunit in factor VIIIa, and residues in both the A1 and A3 domains appear to make contributions to the retention of this subunit. Several factor VIII point mutations have been shown to facilitate the dissociation of A2 relative to WT and these residues localize to either the A1-A2 domain interface (Pipe et al., "Mild Hemophilia A Caused by Increased Rate of Factor VIII A2 Subunit Dissociation: Evidence for Nonproteolytic Inactivation of Factor VIIIa in vivo," *Blood* 93:176-183 (1999); Pipe et al., "Hemophilia A Mutations Associated with 1-stage/2-stage Activity Discrepancy Disrupt Protein-protein Interactions within the Triplicated A Domains of Thrombin-activated Factor VIIIa," *Blood* 97:685-691 (2001)) or the A2-A3 domain interface (Hakeos et al., "Hemophilia A Mutations within the Factor VIII A2-A3 Subunit Interface Destabilize Factor VIIIa and Cause One-stage/Two-stage Activity Discrepancy," *Thromb Haemost.* 88:781-787 (2002)). These factor VIII variants demonstrate a characteristic one-stage/two-stage assay discrepancy (Duncan et al., "Familial Discrepancy Between the One-stage and Two-stage Factor VIII Methods in a Subgroup of Patients with Haemophilia A,", *Br J Haematol.* 87:846-848 (1994); Rudzki et al., "Mutations in a Subgroup of Patients with Mild Haemophilia A and a Familial Discrepancy Between the One-stage and Two-stage Factor VIII:C Methods," *Br J Haematol.* 94:400-406 (1996)), with significant reductions in activity values determined by the latter assay as a result of increased rates of A2 subunit dissociation.

Examination of the ceruloplasmin-based homology model for the A domains of factor VIII (Pemberton et al., "A Molecular Model for the Triplicated A Domains of Human Factor VIII Based on the Crystal Structure of Human Ceruloplasmin," *Blood* 89:2413-2421 (1997)) suggests an extended interface between the A2 domain and each of the A1 and A3 domains, with multiple potential contacts contributing to binding interactions.

Figure 4A:

Significant interest exists in stabilizing factor VIIIa, since a more stable form of the protein would represent a superior therapeutic for hemophilia A, potentially requiring less material to treat the patient (Fay et al., "Mutating Factor VIII:

Lessons from Structure to Function," *Blood Reviews* 19:15-27 (2005)). To this end, preparations of factor VIII have been described where mutations have been made in the recombinant protein to prevent the dissociation of the A2 subunit by introducing novel covalent bonds between A2 and other factor VIII domains (Pipe et al., "Characterization of a Genetically Engineered Inactivation-resistant Coagulation Factor VIIIa," *Proc Natl Acad Sci USA* 94:11851-11856 (1997); Gale et al., "An Engineered Interdomain Disulfide Bond Stabilizes Human Blood Coagulation Factor VIIIa," *J. Thromb. Haemostasis* 1:1966-1971 (2003)). However, it has since been suggested that these types of mutation may not be desirable in a therapeutic factor VIII, because they substantially eliminate means for down-regulation. This situation could yield a prothrombotic condition, which may cause harm. Thus, it would be desirable to enhance the stability of both factor VIII and factor VIIIa, but in a manner that minimizes the likelihood of promoting prothrombotic conditions.

The present invention is directed to overcoming these and other deficiencies in the art.

SUMMARY OF THE INVENTION

A first aspect of the present invention relates to a recombinant factor VIII that includes one or more mutations that result in enhanced stability of both factor VIII and factor VIIIa.

Preferably, the one or more mutations constitute a replacement of one or more charged amino acid residues with a hydrophobic amino acid residue at either or both of the A1A2 or A2A3 domain interfaces, Particularly preferred recombinant factor VII of the present invention includes a substitution of a Glu287 residue of wildtype factor VIII, a substitution of an Asp302 residue of wildtype factor VIII, a substitution of an Asp519 residue of wildtype factor VIII, a substitution of a Glu665 residue of wildtype factor VIII, a substitution of a Glu1984 residue of wildtype factor VIII, or combinations thereof.

A second aspect of the present invention relates to a pharmaceutical composition that includes the recombinant factor VIII according to the first aspect of the present invention.

A third aspect of the present invention relates to an isolated nucleic acid molecule encoding a recombinant factor VIII according to the first aspect of the present invention. Also included within this aspect of the present invention are recombinant DNA expression systems that contain a DNA molecule encoding the recombinant factor VIII of the present invention, and recombinant host cells that contain the DNA molecule and/or recombinant expression system.

A fourth aspect of the present invention relates to a method of making a recombinant factor VIII that includes: growing a host cell according to the third aspect of the present invention under conditions whereby the host cell expresses the recombinant factor VIII; and isolating the recombinant factor VIII.

A fifth aspect of the present invention relates to a method of treating an animal for hemophilia A. This method of treatment includes: administering to an animal exhibiting hemophilia A an effective amount of the recombinant factor VIII according to the first aspect of the present invention, whereby the animal exhibits effective blood clotting following vascular injury.

The present invention demonstrates that a number of charged residues at the A1A2 and A2A3 domain interfaces do not participate in hydrogen bonding, but instead may be destabilizing to factor VIII structure and/or may facilitate the dissociation of the A2 subunit following activation of the factor VIII procofactor. Replacement of these charged residues with hydrophobic residues—with the aim of increasing the buried hydrophobic area and reducing the buried hydrophilic area—was shown in the accompanying Examples to enhance inter-domain binding affinity. Stability parameters were assessed following the activity of the factor VIII variants at elevated temperature and time courses for the decay of factor VIIIa activity resulting from A2 subunit dissociation. Results from these studies demonstrated that a number of mutations yielded increased stability parameters consistent with the elimination of destabilizing forces likely due to buried charge at the AS domain interface. These stabilized variants of factor VIII and activated cofactor VIIIa should afford an improved therapeutic for treatment of hemophilia A.

BRIEF DESCRIPTION OF THE DRAWINGS

FIG. 1 is a graph illustrating the activity of factor VIII mutants relative to WT factor VIII, as measured by one-stage clotting assay (black bar) and two-stage chromogenic factor Xa generation assay (grey bar). Activity for WT and mutant factor VIII forms were measured as described in the Examples. Error bars show the values for standard deviation averaged from three separate determinations.

FIGS. 2A-B illustrate the activity decay of WT and mutant factor VIII and factor VIIIa, respectively. In FIG. 2A, factor VIII (4 nM) was incubated at 55° C. and at the indicated times aliquots were removed and assayed for activity by factor Xa generation assays as described in the Examples. Results are shown for WT (dashed line, open circles), R282A (open triangles), S524A (open squares), N684A (open diamonds), R531A (closed circles), S650A (closed triangles), E287A (closed squares), and D302A (closed diamonds). In FIG. 2B, thrombin-activated factor VIIIa (4 nM) in the presence of 40 nM factor IXa was incubated at 23° C., aliquots were taken at indicated time points and activity was measured by factor Xa generation assay as described in the Examples. Results are shown for WT (dashed line, open circles), R282A (open triangles), S524A (open squares), Y1792F (open diamonds), N684A (closed circles), Y1786F (closed triangles), R531A (closed squares), E287A (closed diamonds), and D302A (grey circles), Results for selected fast decay variants are shown in an expanded scale in the inset to FIG. 2B.

FIGS. 3A-B illustrate SDS-PAGE and Western blot analysis of factor VIII mutants and WT factor VIII. FIG. 3A shows purified WT and mutant factor VIII proteins (0.77 μg) following SDS-PAGE on 8% polyacrylamide gels that were visualized by GelCode. FIG. 3B shows purified WT and mutant factor VIII proteins (0.34 μg) that were electrophoresed on 8% polyacrylamide gels, transferred to PVDF membranes, and probed by biotinylated R8B12 antibody. Bands were visualized by chemifluorescence as described in accompanying Examples. WT (lane 1), Glu272Ala (lane 2), Glu272Val (lane 3), Asp519Ala (lane 4), Asp519Val (lane 5), Glu665Ala (lane 6), Glu665Val (lane 7), Glu1984Ala (lane 8), and Glu1984Val (lane 9). MW, molecular weight marker: sFVIII, single chain form factor VIII: SC, heavy chain: LC, light chain. An apparent stoichiometry ratios of single chain form to heterodimer of WT and mutant factor VIII forms were 0.96 (WT), 0.64 (Glu272Ala), 0.92 (Glu272Val), 0.74 (Asp519Ala), 0.8 (Asp519Val), 0.64 (Glu665Ala), 0.63 (Glu665Val), 0.91 (Glu 1984Ala), and 0.5 (Glu 1984Val).

FIGS. 4A-D illustrate specific activity of factor VIII mutants relative to WT factor VIII and thrombin generation assays. FIG. 4A shows activity values that were determined using a one-stage clotting assay (grey bar) and two-stage chromogenic factor Xa generation assay (solid bar) as described in the accompanying Examples. FIG. 4B-C illustrate thrombogram of factor VIII proteins. WT (dashed line), Glu272Ala (open squares), Glu272Val (closed squares), Asp519Ala (open circles), Asp519Val (closed circles), Glu665Ala (open triangles), Glu665Val (closed triangles), Glu1984Ala (open diamonds), and Glu1984Val (closed diamonds). FIG. 4D illustrates parameter values obtained from thrombin generation assays. Thrombin generation assays were performed as described in the accompanying Examples. Thrombograms show the average values of triplicated samples. The parameter values were expressed as values (%) relative to WT. The actual values for WT were 7.5±0.5 min (lag time), 13.7±0.3 min (peak time), 157.3±14.7 nM (peak value), 979.8±37.9 nM/min (FTP). Lag time (open bar), Peak time (grey bar), Peak Value (closed bar), and ETP (lined bar) are shown. Error bars show the standard deviation values averaged from three separate determinations.

Figure 5A:
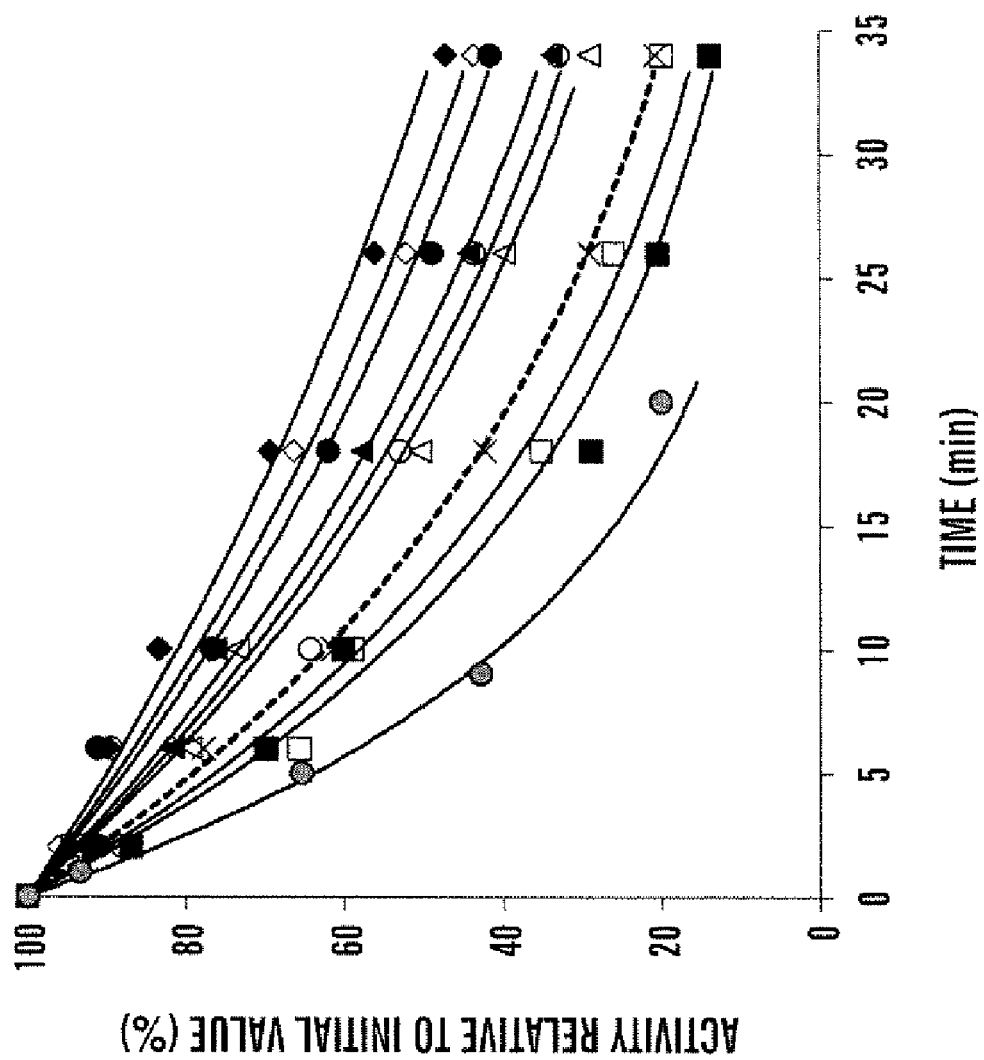
Figure 5B:
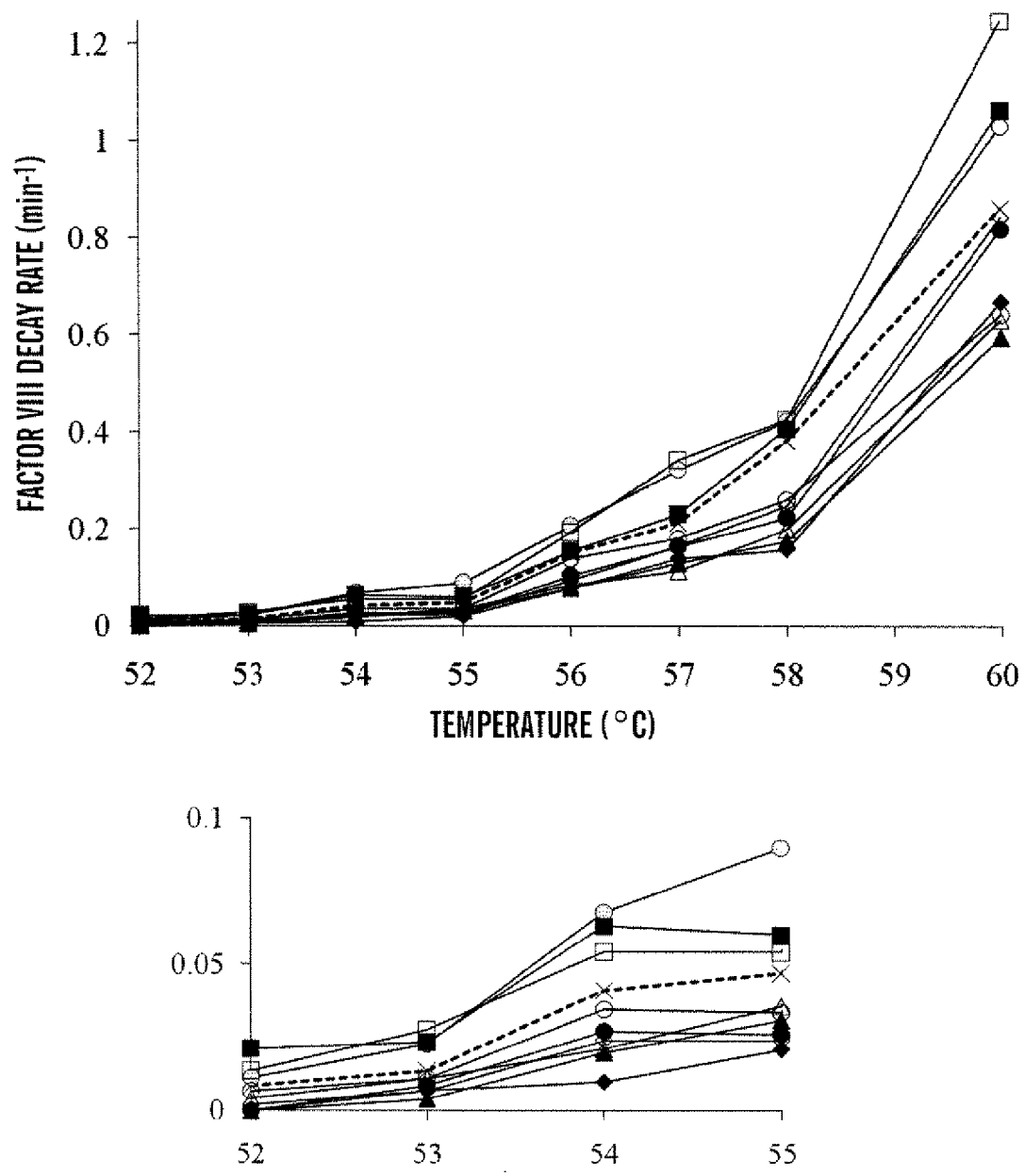

FIGS. 5A-B illustrate activity decay of WT and mutant factor VIII. Factor VIII (4 nM) was incubated at various temperatures (52-60° C.) and at the indicated times aliquots were removed and assayed for activity by factor Xa generation assays as described in the accompanying Examples. Data were fitted by non-linear least squares regression, and decay rates were obtained. Each point represents the value averaged from three separate determinations. Results are shown for WT (dashed line, cross symbols), Glu272Ala (open squares), Glu272Val (closed squares), Asp519Ala (open circles), Asp519Val (closed circles), Glu665Ala (open triangles), Glu665Val (closed triangles), Glu1984Ala (open diamonds), Glu1984Val (closed diamonds), and full-length Kogenate factor VIII (grey circles). FIG. 5A illustrates representative factor VIII decay curves after 55° C. incubation. FIG. 5B illustrates plots of factor VIII decay rate at various temperatures. The inset graph in FIG. 5B is an enlargement of the decay results over the temperature range of 52-55° C.

Figure 6:
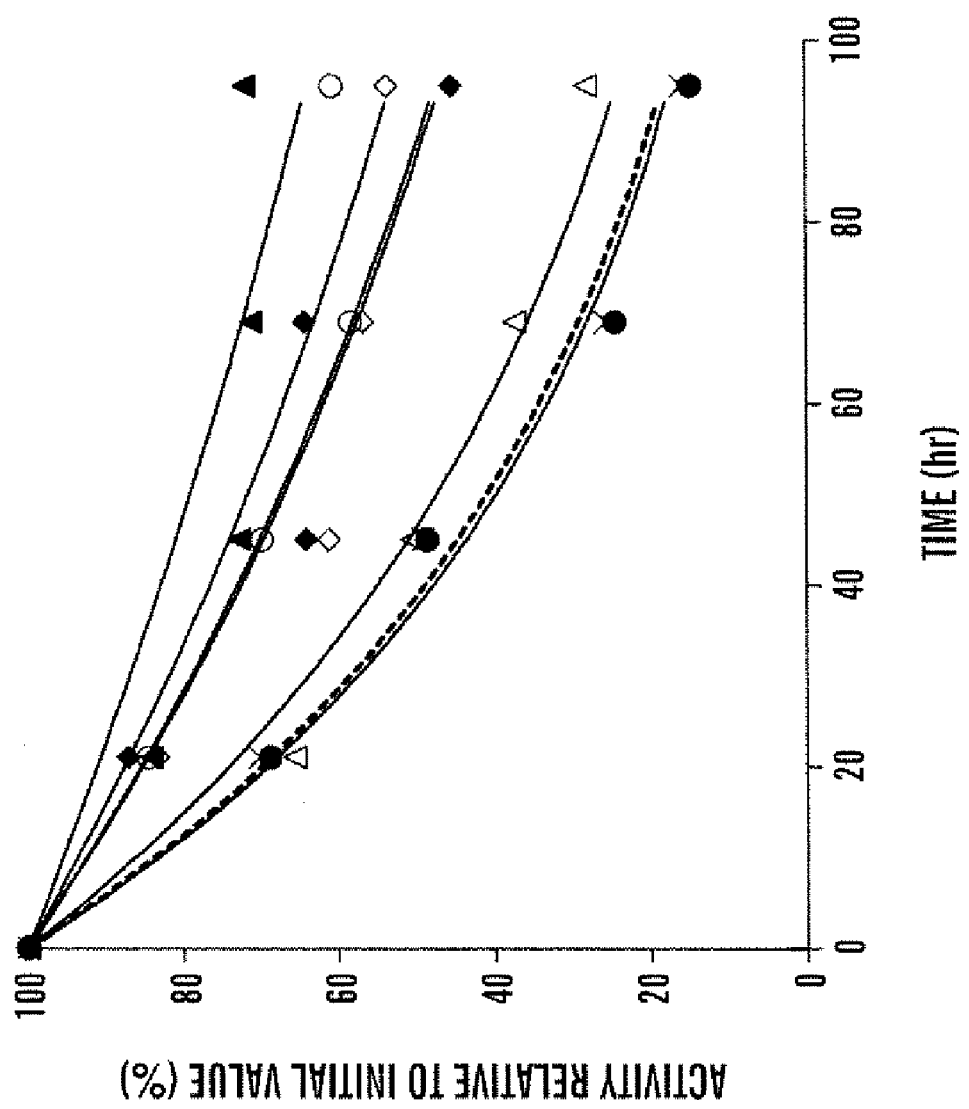

FIG. 6 is a graph illustrating activity decay of factor VIII in plasma at 37° C. Factor VIII (1 nM) was incubated at 37° C. in factor VIII deficient plasma and at the indicated times aliquots were removed and assayed for one-stage clotting assays as described in the accompanying Examples. Results are shown for WT (dashed line, cross symbols), Asp519Ala (open circles), Asp519Val (closed circles), Glu665Ala (open triangles), Glu665Val (closed triangles), Glu1984Ala (open diamonds), and Glu1984Val (closed diamonds). Data were fitted by non-linear least squares regression and each point represents the value averaged from three separate determinations.

Figure 7A:
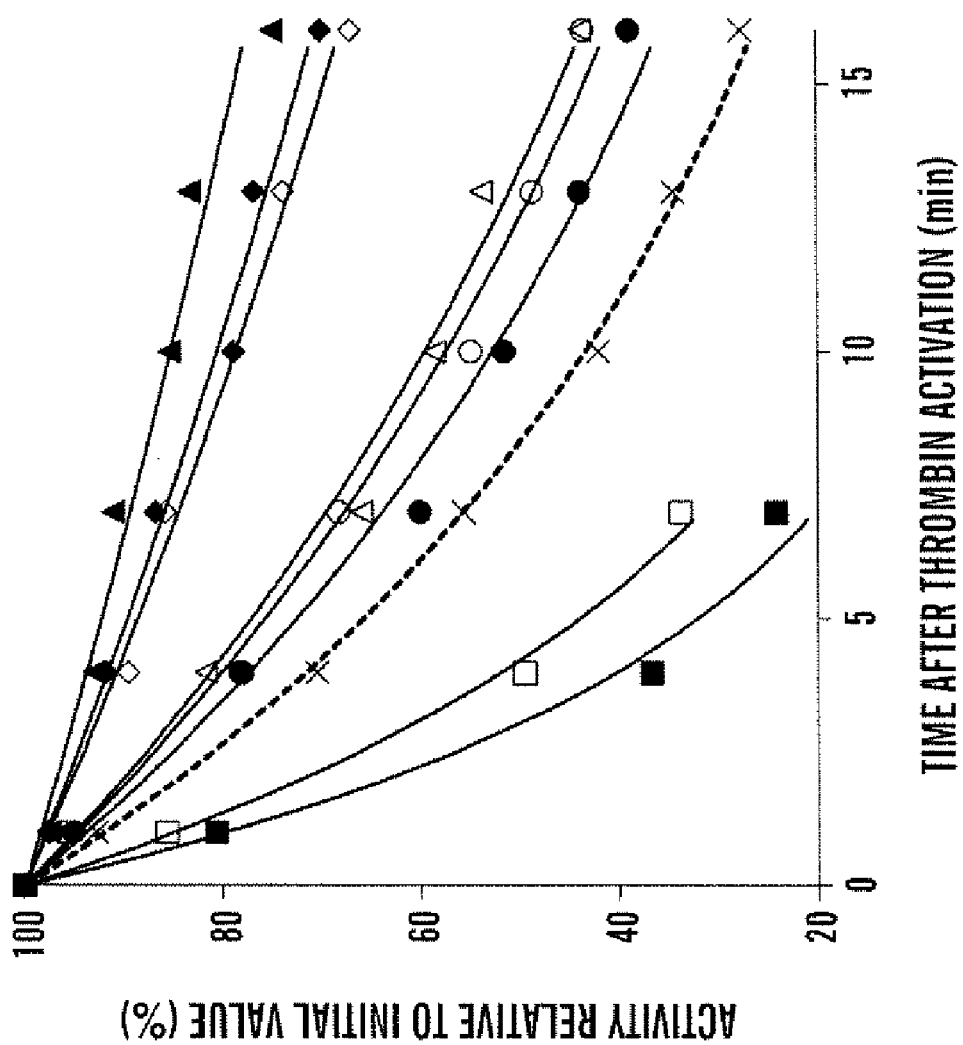
Figure 7B:
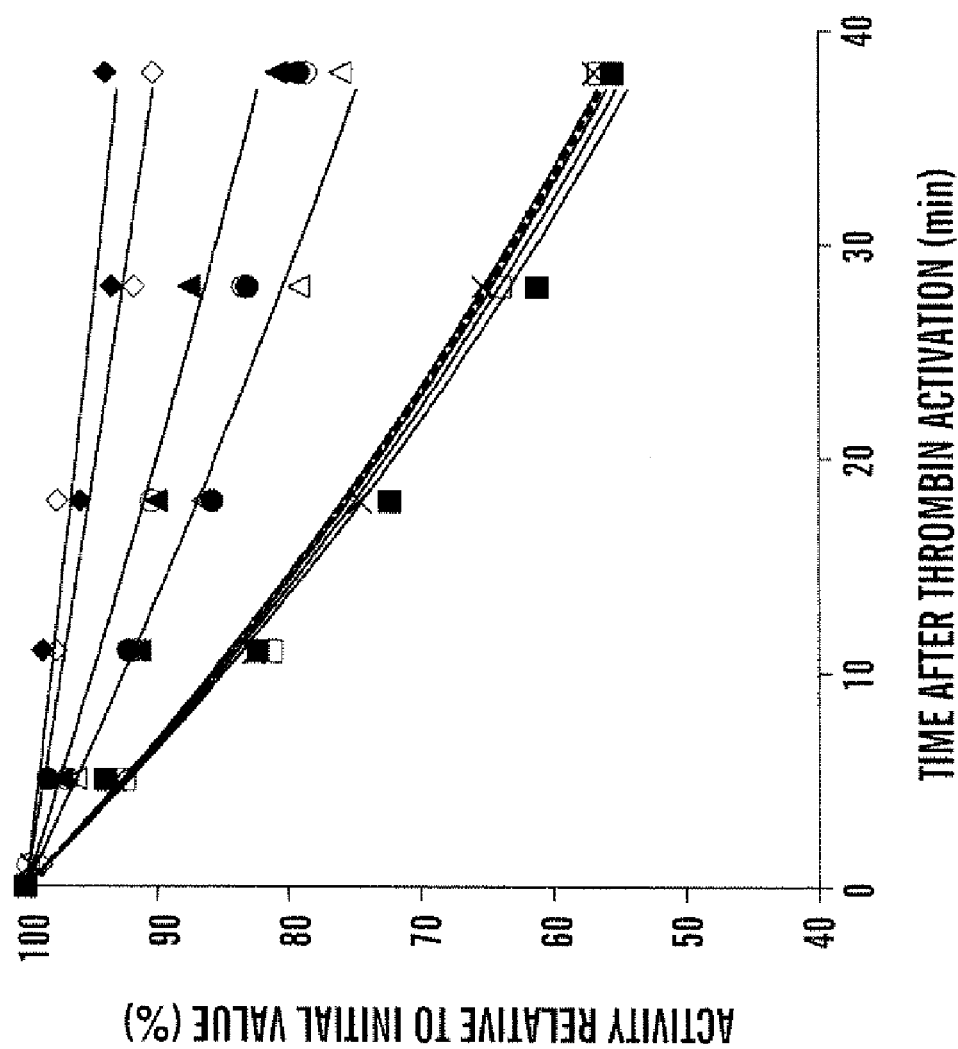

FIGS. 7A-B are graphs illustrating the activity decay of WT and mutant factor VIIIa in the absence or presence of factor IXa. FIG. 7A shows thrombin-activated factor VIIIa (4 nM) that was incubated at 23° C. Aliquots were taken at indicated time points and activity was measured by factor Xa generation assay as described in the accompanying Examples. FIG. 7B shows activity decay of WT and mutant factor VIIIa in the presence of factor IXa. Factor VIIIa (4 nM) was activated with thrombin in the presence of 40 nM factor IXa. Aliquots were taken at indicated time points and activity was measured by factor Xa generation assay as described in the accompanying Examples. Results are shown for WT (dashed line, cross symbols), Glu272Ala (open squares), Glu272Val (closed squares), Asp519Ala (open circles), Asp519Val (closed circles), Glu665Ala (open triangles), Glu665Val (closed triangles), Glu1984Ala (open diamonds), and Glu1984Val (closed diamonds) Data were fitted by non-linear least squares regression and each point represents the value averaged from three separate determinations.

Figure 8:
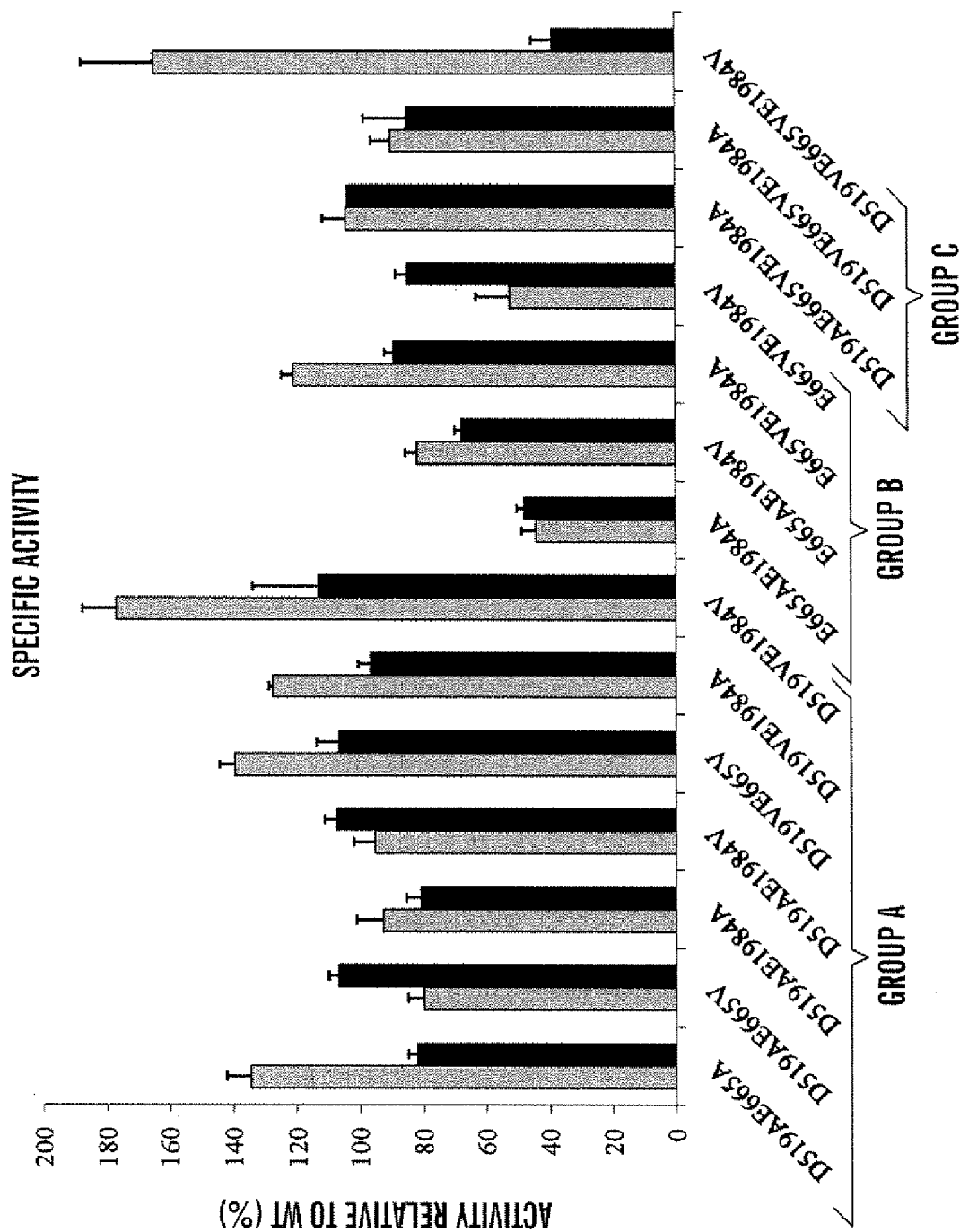

FIG. 8 is a graph illustrating the specific activity of factor VIII double or triple combination mutants having Asp519, Glu665, and/or Glu1984 residues changed to Ala or Val. Activity values were determined using a one-stage clotting assay (grey bar) and two-stage chromogenic factor Xa generation assay (black bar) as described in the Examples. Error bars show the standard deviation values averaged from three separate determinations.

Figure 9:
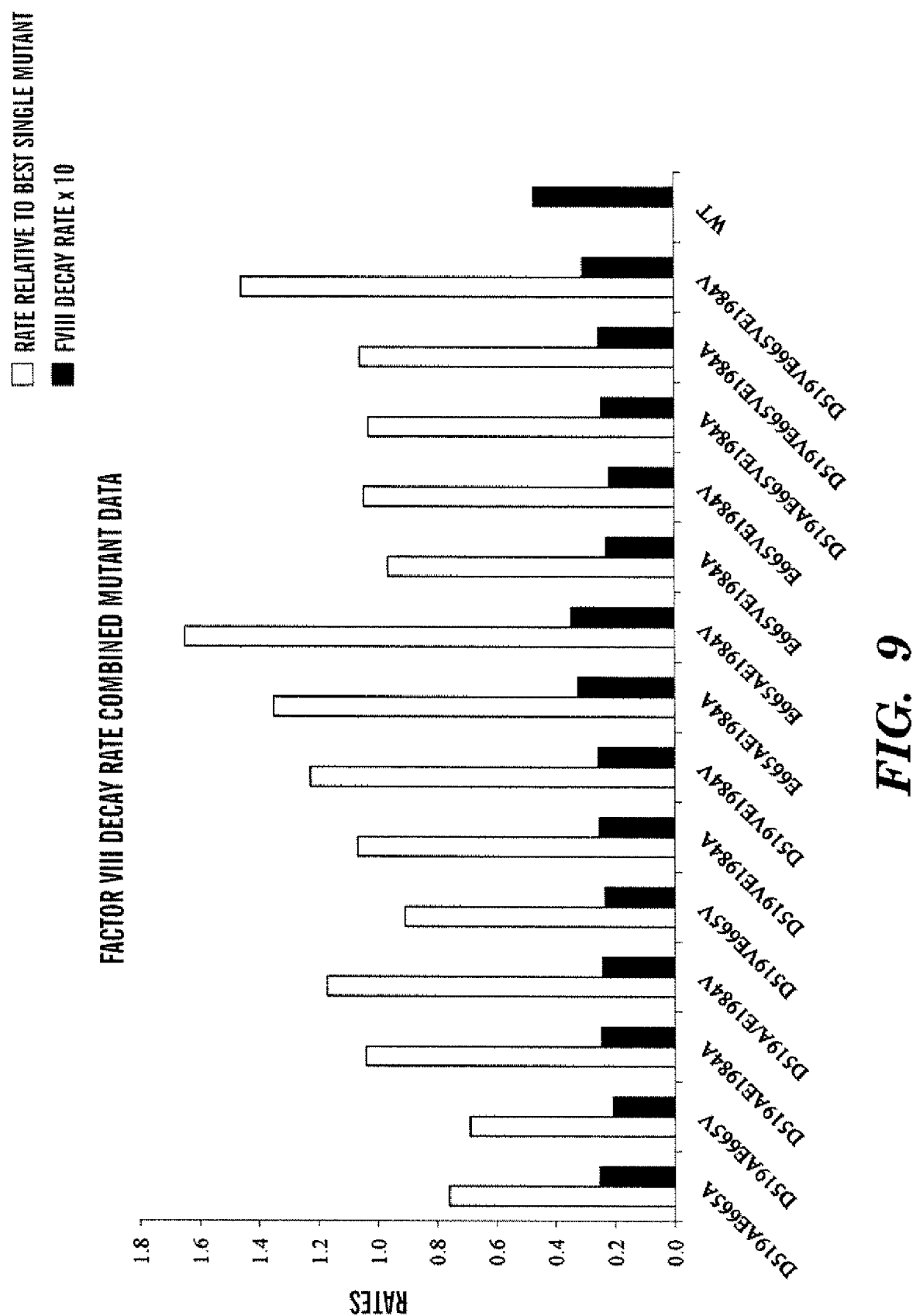

FIG. 9 is a graph illustrating factor VIII activity decay rates for WT and factor VIII double or triple combination mutants having Asp519, Glu665, and/or Glu1984 residues changed to Ala or Val. Factor VIII activity decay experiments were performed and decay rates were estimated by non-linear least squares regression as described in the Examples. Grey bars show the rates relative to the best single mutants (see Example 5, FIG. 5A) and were calculated after division by the rate of best (lowest) value. For example, the rate relative values to the best single mutant of the D5519AE665A pairing equals the decay rate for D5519AE665A divided by the decay rate of D519A. Black bars show the actual decay rate parameter values represented×10.

Figure 10:
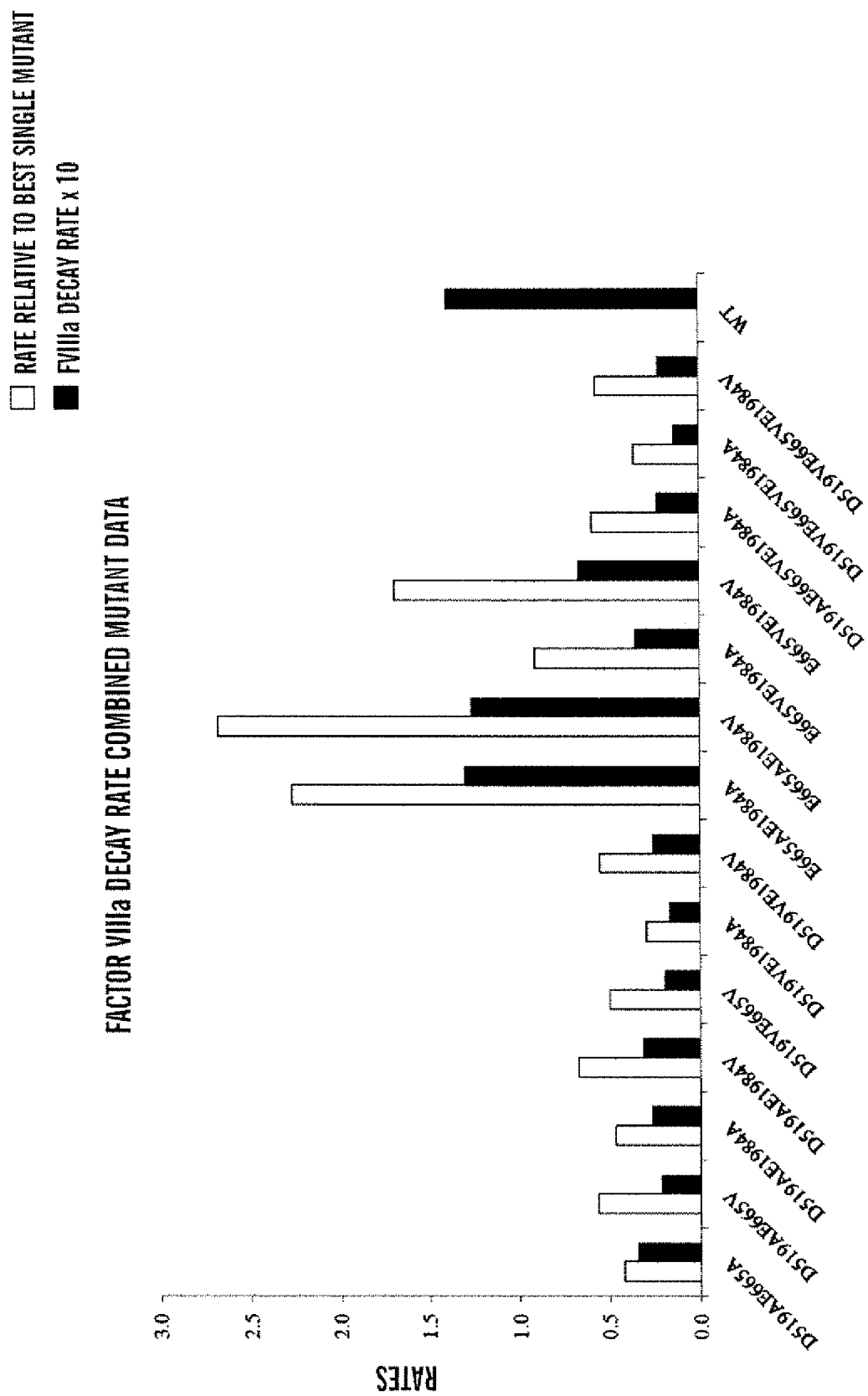

FIG. 10 is a graph illustrating factor VIIIa activity decay rate of WT and factor VIII double or triple combination mutants having Asp519, Glu665, and Glu1984 residues changed to Ala or Val. Factor VIIIa activity decay measurements after incubation of 1.5 nM factor VIIIa in the absence of factor IXa were performed and decay rates were estimated by non-linear least squares regression as described in the Examples. Grey bars show the rates relative to best single mutants (see Example 7, FIG. 7A), and were calculated as described in the legend to FIG. 9. Black bars show the actual decay rate parameter values represented×10.

Figure 11A:
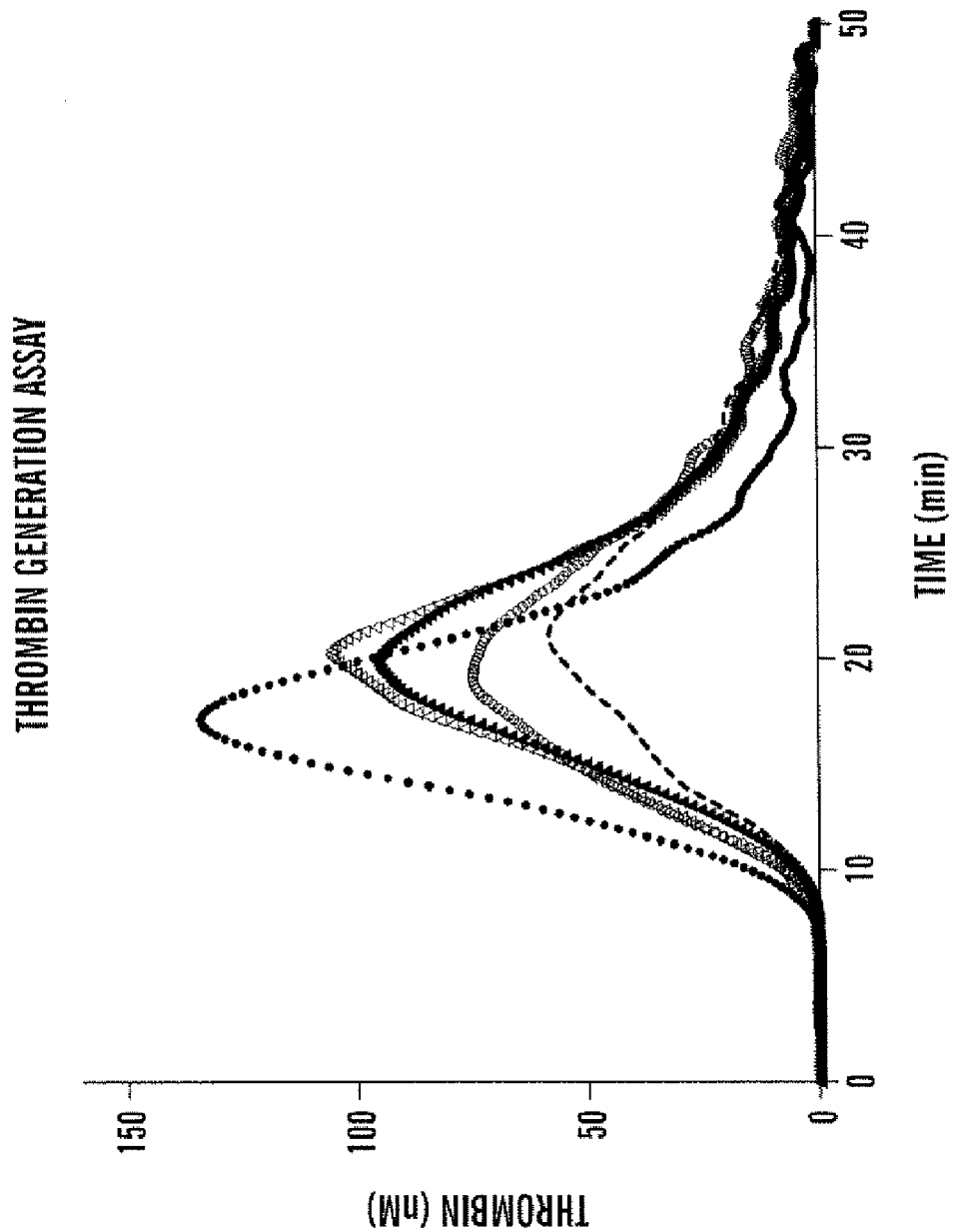
Figure 11B:
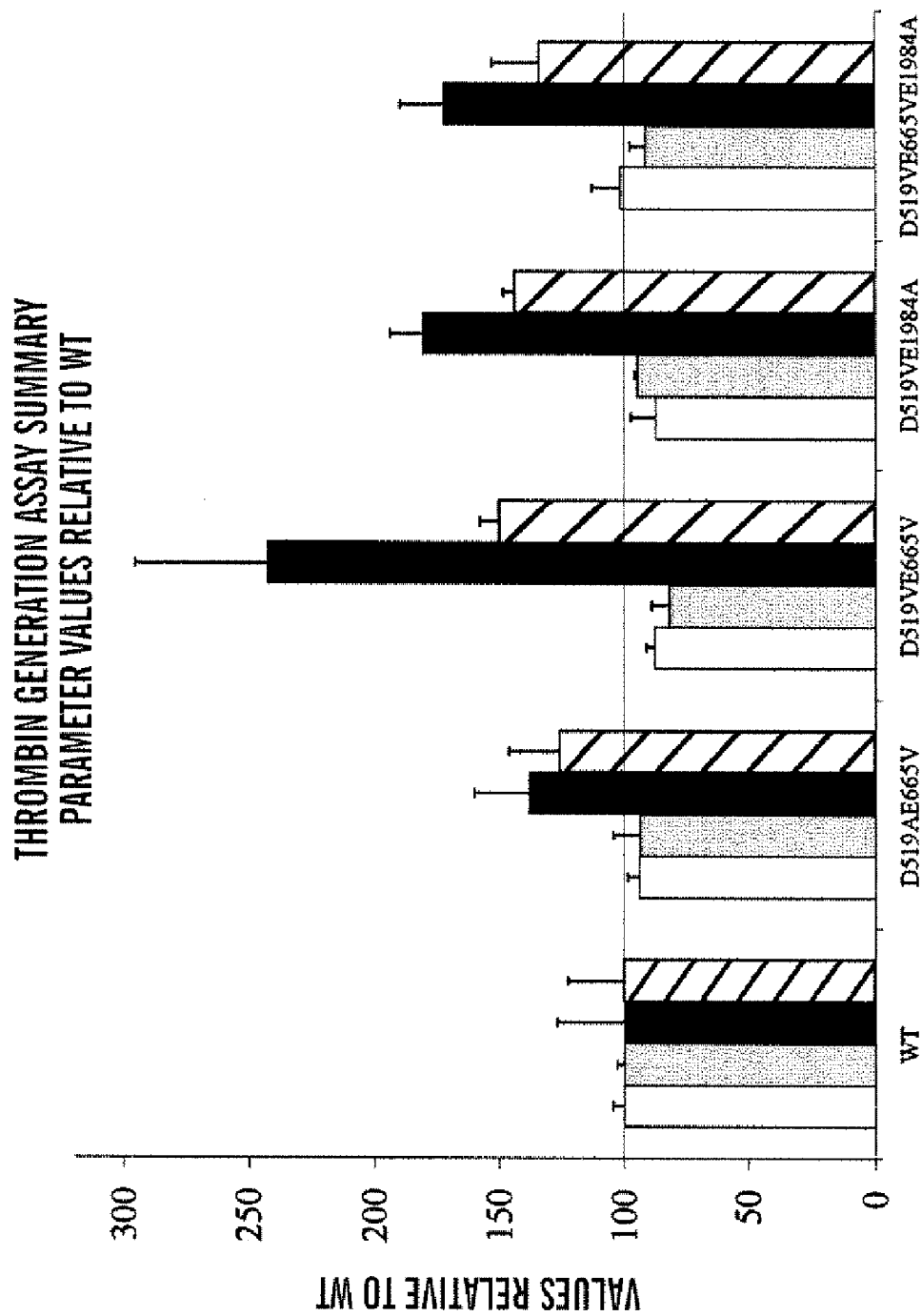

FIGS. 11A-B illustrate the results of thrombin generation assay using the combination mutants. FIG. 11A shows the thrombogram of factor VIII proteins. Thrombin generation assays were performed as described in the Examples. Final concentrations of reagents were 0.2 nM (factor VIII), 0.5 µM (rTF), 4 µM (PSPCPE vesicles), 433 µM (fluorogenic substrate), 13.3 mM CaCl$_2$, and 105 nM (thrombin calibrator). The results are shown for WT (dashed line), D519AE665V (open circles), D519VE665V (closed circles), D519VE1984A (open triangles), and D519VE665VE1984A (closed triangles). FIG. 11B shows parameter values obtained from thrombin generation assay. Thrombograms show the average values of triplicated samples. The parameter values were expressed as values (%) relative to WT. The actual values for WT were 8.5±0.4 min (lag time), 21.3±0.6 min (peak time), 58.5±15.6 nM (peak value), 883.6±199.8 nM/min (ETP). Lag time (open bar), Peak time (grey bar), Peak Value (closed bar), and ETP (lined bar). Error bars show the standard deviation values averaged from three separate determinations.

Figure 12A:
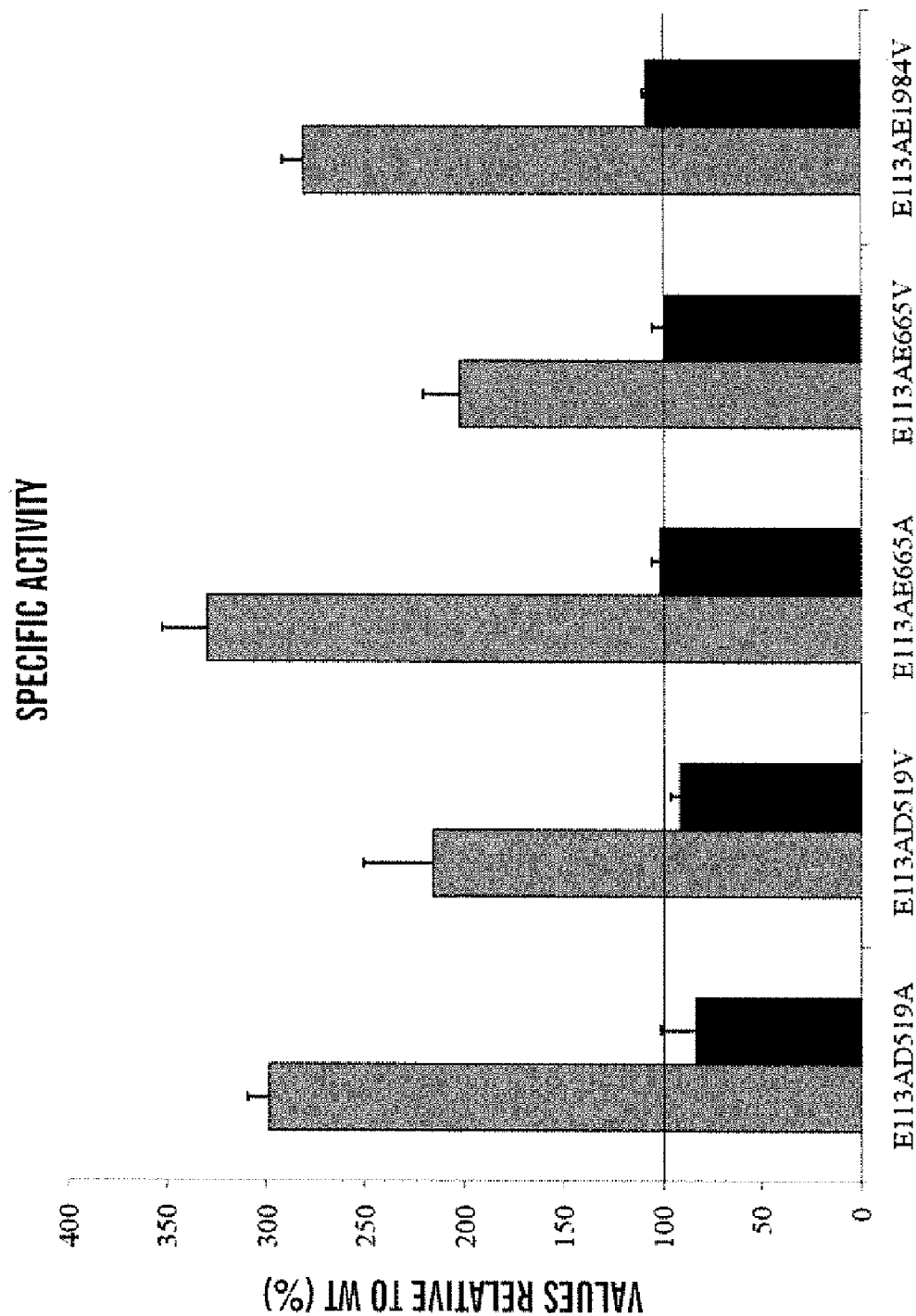
Figure 12B:
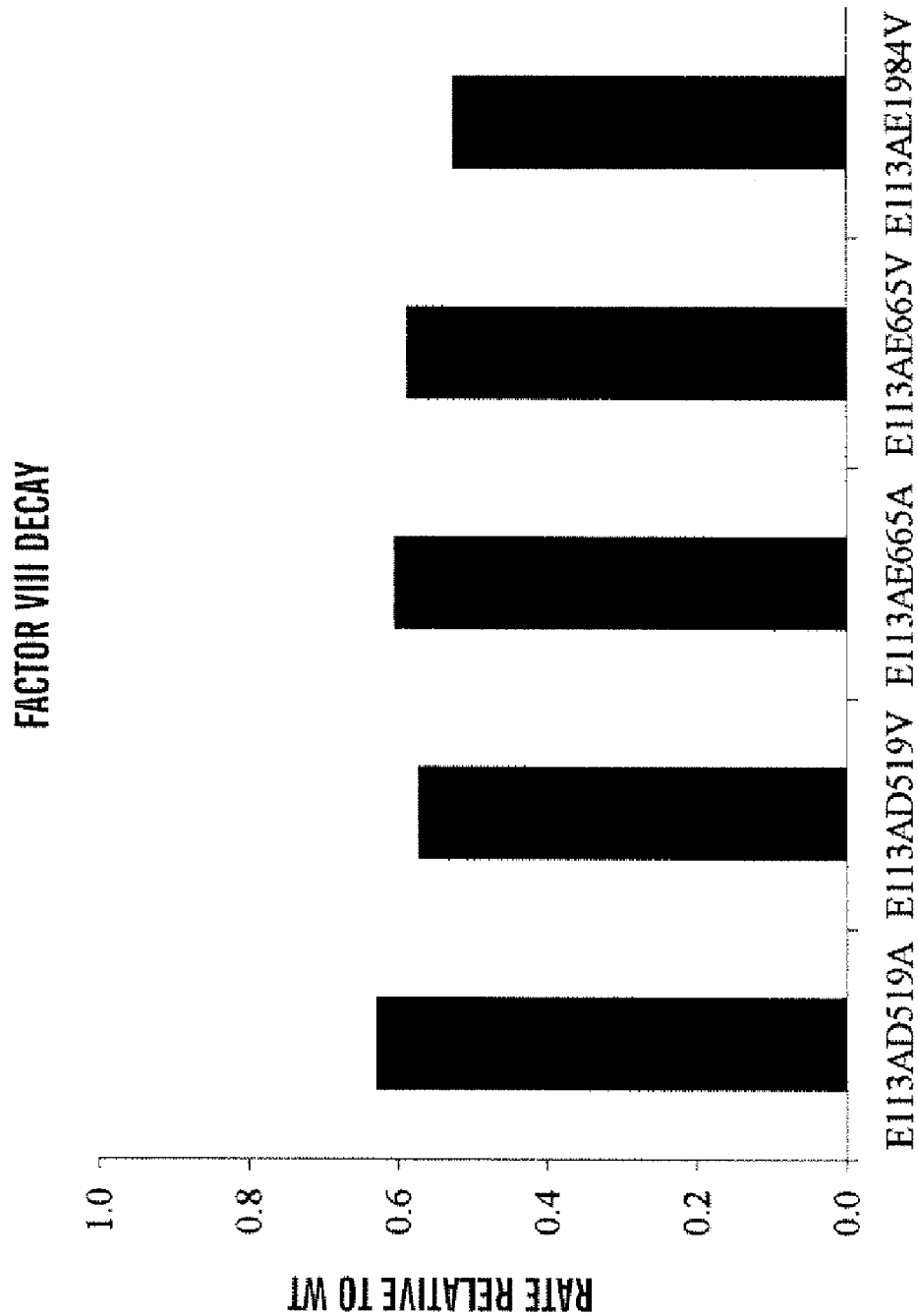
Figure 12C:
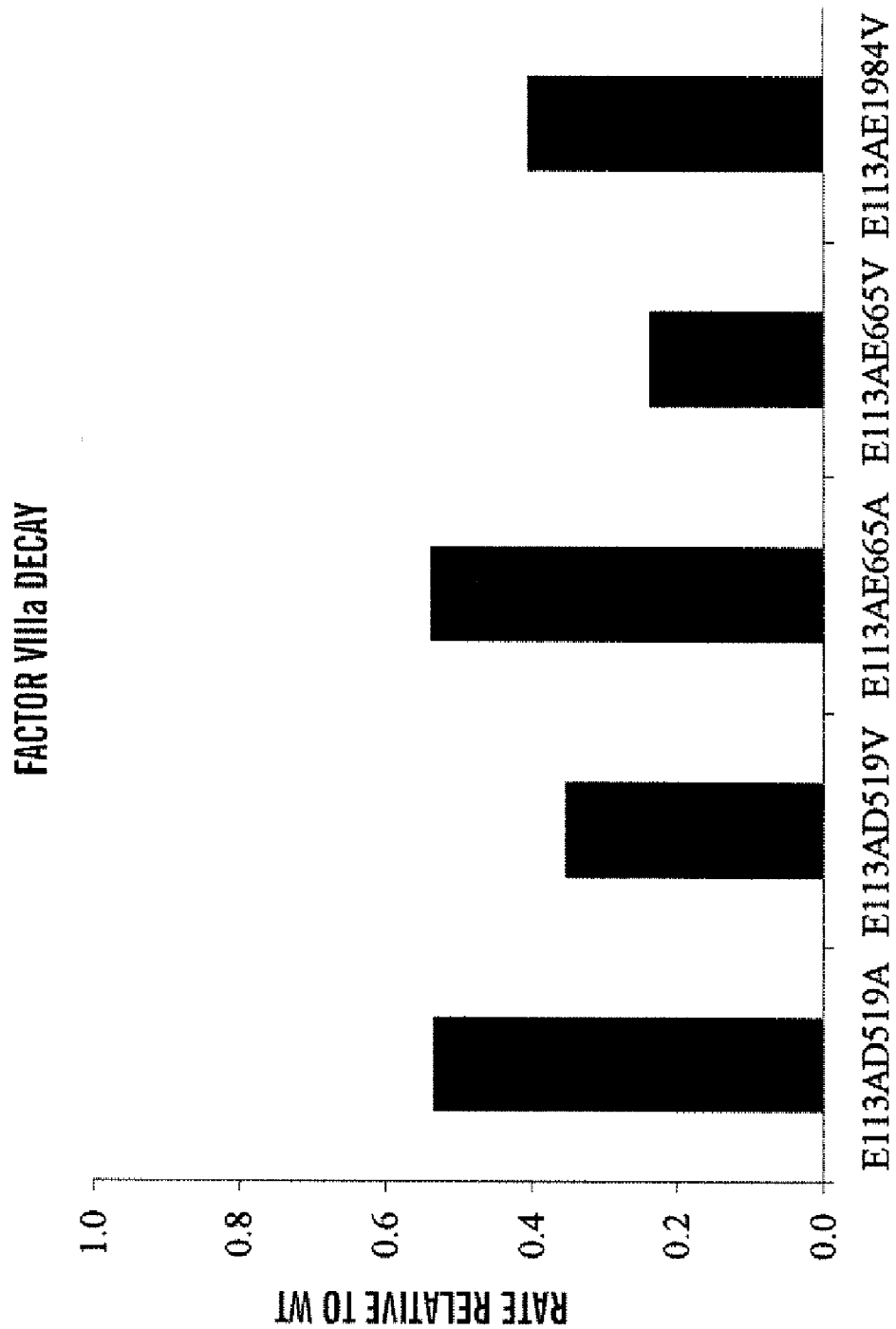

FIGS. 12A-C illustrate the specific activity and activity decay rates for factor VIII and factor VIIIa relative to WT for Ala or Val mutants at residues Asp519, Glu665, and/or Glu1984 in combination with Glu113Ala mutation. FIG. 12A shows specific activity of the combination mutants versus WT, as determined using a one-stage clotting assay (grey bar) and two-stage chromogenic factor Xa generation assay (black bar) as described in the Examples. Error bars show the standard deviation values averaged from three separate determinations. FIG. 12B shows the results of factor VIII activity decay assays at 55° C.; decay rates were estimated by non-linear least squares regression as described in the Examples. FIG. 12C shows the results of factor VIIIa activity decay measurements after incubation of 1.5 nM factor VIIIa in the absence of factor IXa; decay rates were estimated by nonlinear least squares regression as described in the Examples.

DETAILED DESCRIPTION OF THE INVENTION

The present invention relates to a recombinant factor VIII having one or more mutations that result in enhanced stability of both factor VIII and factor VIIIa.

The recombinant factor VIII of the present invention can be prepared by modifying the amino acid sequence of a wild-type factor VIII or a mutant factor VIII that has otherwise been modified to affect other properties of the factor VIII, such as antigenicity, circulating half-life, protein secretion, affinity for factor IXa and/or factor X, altered factor VIII-inactivation cleavage sites, immunogenicity, shelf-life, etc.

Suitable wild-type factor VIII that can be modified in accordance with the present invention can be from various animals including, without limitation, mammals such as humans (see, e.g., GenBank Accession Nos. AAA52484 (amino acid) and K01740 (nucleotide); and GenBank Accession Nos. CAD97566 (amino acid) and AX746360 (nucleotide), which are hereby incorporated by reference in their entirety), rats (see, e.g., GenBank Accession Nos. AAQ21580 (amino acid) and AY362193 (nucleotide), which are hereby incorporated by reference in their entirety), mice (see, e.g., GenBank Accession Nos. AAA37385 (amino acid) and L05573 (nucleotide), which are hereby incorporated by reference in their entirety), guinea pigs, dogs (see, e.g., GenBank Accession Nos. AAB87412 (amino acid) and AF016234 (nucleotide); and GenBank Accession Nos. AAC05384 (amino acid) and AF049489 (nucleotide), which are hereby incorporated by reference in their entirety), cats, monkeys, chimpanzees (see, e.g., GenBank Accession Nos. XP_529212 (amino acid) and XM_529212 (nucleotide), which are hereby incorporated by reference in their entirety), orangutans, cows, horses, sheep, pigs (see, e.g., GenBank Accession Nos. NP_999332 (amino acid) and NM_214167 (nucleotide), which are hereby incorporated by reference in their entirety), goats, rabbits, and chickens. These and other sequences are also available electronically via the Haemophilia A Mutation, Structure, Test and Resource Site (or HAMSTeRS), which further provides an alignment of human, porcine, murine, and canine factor VIII proteins. Thus, the conservation and homology among mammalian factor VIII proteins is well known.

By way of example, the human factor VIII cDNA nucleotide and predicted amino acid sequences are shown below in SEQ ID NOs: 1 and 2, respectively. Human factor VIII is synthesized as an approximately 300 kDa single chain protein with internal sequence homology that defines the "domain" sequence $NH_2$-A1-A2-B-A3-C1-C2-COOH. In a factor VIII molecule, a "domain," as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO: 2):

A1, residues $Ala_1$-$Arg_{372}$;
A2, residues $Ser_{373}$-$Arg_{740}$;
B, residues $Ser_{741}$-$Arg_{1648}$;
A3, residues $Ser_{1690}$-$Ile_{2032}$;
C1, residues $Arg_{2033}$-$Asn_{2172}$; and
C2, residues $Ser_{2173}$-$Tyr_{2332}$.

The A3-C1-C2 sequence includes residues $Ser_{1690}$-$Tyr_{2332}$. The remaining sequence, residues $Glu_{1649}$-$Arg_{1689}$, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

The gene encoding the wild-type human factor VIII has a nucleotide sequence of SEQ ID NO: 1, as follows:

gccaccagaagatactacctgggtgcagtggaactgtcatgggactatat gcaaagtgatctcggtgagctgcctgtggacgcaagatttcctcctagag tgccaaaatcttttccattcaacacctcagtcgtgtacaaaaagactctg tttgtagaattcacggatcaccttttcaacatcgctaagccaaggccacc ctggatgggtctgctaggtcctaccatccaggctgaggtttatgatacag tggtcattacacttaagaacatggcttcccatcctgtcagtcttcatgct gttggtgtatcctactggaaagcttctgagggagctgaatatgatgatca gaccagtcaaagggagaaagaagatgataaagtcttccctggtggaagcc atacatatgtctggcaggtcctgaaagagaatggtccaatggcctctgac ccactgtgccttacctactcatatctttctcatgtggacctggtaaaaga cttgaattcaggcctcattggagccctactagtatgtagagaagggagtc tggccaaggaaaagacacagaccttgcacaaatttatactactttttgct gtatttgatgaagggaaaagttggcactcagaaacaaagaactccttgat gcaggatagggatgctgcatctgctcgggcctggcctaaaatgcacacag tcaatggttatgtaaacaggtctctgccaggtctgattggatgccacagg aaatcagtctattggcatgtgattggaatgggcaccactcctgaagtgca ctcaatattcctcgaaggtcacacatttcttgtgaggaaccatcgccagg cgtccttggaaatctcgccaataactttccttactgctcaaacactcttg atggaccttggacagtttctactgttttgtcatatctcttcccaccaaca tgatggcatggaagcttatgtcaaagtagacagctgtccagaggaacccc aactacgaatgaaaaataatgaagaagcggaagactatgatgatgatctt actgattctgaaatggatgtggtcaggtttgatgatgacaactctccttc ctttatccaaattcgctcagttgccaagaagcatcctaaaacttgggtac attacattgctgctgaagaggaggactgggactatgctcccttagtcctc gcccccgatgacagaagttataaaagtcaatatttgaacaatggccctca gcggattggtaggaagtacaaaaaagtccgatttatggcatacacagatg aaacctttaagactcgtgaagctattcagcatgaatcaggaatcttggga cctttactttatgggaagttggagacacactgttgattatatttaagaa tcaagcaagcagaccatataacatctaccctcacggaatcactgatgtcc gtccttgtattcaaggagattaccaaaaggtgtaaaacatttgaaggat tttccaattctgccaggagaaatattcaaatataaatggacagtgactgt agaagatgggccaactaaatcagatcctcggtgcctgacccgctattact ctagtttcgttaatatggagagagatctagcttcaggactcattggccct -continued ctcctcatctgctacaaagaatctgtagatcaaagaggaaaccagataat gtcagacaagaggaatgtcatcctgttttctgtatttgatgagaaccgaa gctggtacctcacagagaatatacaacgctttctccccaatccagctgga gtgcagcttgaggatccagagttccaagcctccaacatcatgcacagcat caatggctatgttttgatagtttgcagttgtcagtttgtttgcatgagg tggcatactggtacattctaagcattggagcacagactgacttcctttct gtcttcttctctggatataccttcaaacacaaaatggtctatgaagacac actcaccctattcccattctcaggagaaactgtcttcatgtcgatggaaa acccaggtctatggattctggggtgccacaactcagactttcggaacaga ggcatgaccgccttactgaaggtttctagttgtgacaagaacactggtga ttattacgaggacagttatgaagatatttcagcatacttgctgagtaaaa acaatgccattgaaccaagaagcttctcccagaattcaagacaccctagc actaggcaaaagcaatttaatgccaccacaattccagaaaatgacataga gaagactgaccctggtttgcacacagaacctatgcctaaaatacaaa atgtctcctctagtgatttgttgatgctcttgcgacagagtcctactcca catgggctatccttatctgatctccaagaagccaaatatgagacttttc tgatgatccatcacctggagcaatagacagtaataacagcctgtctgaaa tgacacacttcaggccacagctccatcacagtggggacatggtatttacc cctgagtcaggcctccaattaagattaaatgagaaactggggacaactgc agcaacagagttgaagaaacttgatttcaaagtttctagtacatcaaata atctgatttcaacaattccatcagacaattggcagcaggtactgataat acaagttccttaggaccccaagtatgccagttcattatgatagtcaatt agataccactctatttggcaaaaagtcatctccccttactgagtctggtg gacctctgagcttgagtgaagaaaataatgattcaaagttgttagaatca ggtttaatgaatagccaagaaagttcatggggaaaaaatgtatcgtcaac agagagtggtaggttatttaaagggaaaagagctcatggacctgctttgt tgactaaagataatgccttattcaaagttagcatctctttgttaaagaca aacaaaacttccaataattcagcaactaatagaaagactcacattgatgg cccatcattattaattgagaatagtccatcagtctggcaaaatatattag aaagtgacactgagtttaaaaaagtgacacctttgattcatgacagaatg cttatgacaaaaatgctacagctttgaggctaaatcatatgtcaaataa aactacttcatcaaaaaacatggaaatggtccaacagaaaaaagagggcc ccattccaccagatgcacaaaatccagatatgtcgttctttaagatgcta ttcttgccagaatcagcaaggtggatacaaaggactcatggaagaactc tctgaactctgggcaaggcccagtccaaagcaattagtatccttaggac cagaaaatctgtggaaggtcagaattcttgtctgagaaaaacaaagtg gtagtaggaaagggtgaatttacaaaggacgtaggactcaaagagatggt ttttccaagcagcagaaacctatttcttactaacttggataatttacatg aaataatacacacaatcaagaaaaaaaaattcaggaagaaatagaaaag aaggaaacattaatccaagagaatgtagttttgcctcagatacatacagt -continued gactggcactaagaatttcatgaagaaccttttcttactgagcactaggc aaaatgtagaaggttcatatgacggggcatatgctccagtacttcaagat tttaggtcattaaatgattcaacaaatagaacaaagaaacacacagctca tttctcaaaaaaggggaggaagaaaacttggaaggcttgggaaatcaaa ccaagcaaattgtagagaaatatgcatgcaccacaaggatatctcctaat acaagccagcagaattttgtcacgcaacgtagtaagagagctttgaaaca attcagactcccactagaagaaacagaacttgaaaaaggataattgtgg atgacacctcaacccagtggtccaaaaacatgaaacatttgaccccgccc ttatcagattgccttacgaggagtcatagcatccctcaagcaaatagatc tccattacccattgcaaaggtatcatcatttccatctattagacctatat atctgaccagggtcctattccaagacaactcttctcatcttccagcagca tcttatagaaagaaagattctggggtccaagaaagcagtcatttcttaca aggagccaaaaaaataaccttcttttagccattctaaccttggagatga ctggtgatcaaagagaggttggctccctggggacaagtgccacaaattca gtcacatacaagaaagttgagaacactgttctcccgaaaccagacttgcc caaaacatctggcaaagttgaattgcttccaaaagttcacatttatcaga aggacctattccctacggaaactagcaatgggtctcctggccatctggat ctcgtggaagggagccttcttcagggaacagagggagcgattaagtggaa tgaagcaaacagacctggaaaagttccctttctgagagtagcaacagaaa gctctgcaaagactcccctccaagctattggatcctcttgcttgggataac cactatggtactcagataccaaaagaagagtggaaatcccaagagaagtc accagaaaaacagctttaagaaaaaggataccattttgtccctgaacg cttgtgaaagcaatcatgcaatagcagcaataaatgagggacaaaataag cccgaaatagaagtcacctgggcaaagcaaggtaggactgaaaggctgtg ctctcaaaacccaccagtcttgaaacgccatcaacgggaaataactcgta ctactcttcagtcagatcaagaggaaattgactatgatgataccatatca gttgaaatgaagaaggaagattttgacatttatgatgaggatgaaaatca gagccccgcagctttcaaaagaaaacacgacactattttattgctgcag tggagaggctctgggattatgggatgagtagctccccacatgttctaaga aacagggctcagagtggcagtgtccctcagttcaagaaagttgttttcca ggaatttactgatggctcctttactcagcccttataccgtggagaactaa atgaacatttgggactcctggggccatatataagagcagaagttgaagat aatatcatggtaactttcagaaatcaggcctctcgtccctattccttcta ttctagccttatttcttatgaggaagatcagaggcaaggagcagaaccta gaaaaaactttgtcaagcctaatgaaaccaaaacttactttggaaagtg caacatcatatggcacccactaaagatgagtttgactgcaaagcctgggc ttatttctctgatgttgacctggaaaaagatgtgcactcaggcctgattg gaccccttctggtctgccacactaacacactgaaccctgctcatgggaga caagtgacagtacaggaatttgctctgttttcaccatctttgatgagac caaaagctggtacttcactgaaaatatggaagaaactgcagggctccct gcaatatccagatggaagatcccactttaaagagaattatcgcttccat

```
gcaatcaatggctacataatggatacactacctggcttagtaatggctca ggatcaaaggattcgatggtatctgctcagcatgggcagcaatgaaaaca tccattctattcatttcagtggacatgtgttcactgtacgaaaaaagag gagtataaaatggcactgtacaatctctatccaggtgttttgagacagt ggaaatgttaccatccaaagctggaatttggcgggtggaatgccttattg gcgagcatctacatgctgggatgagcacacttttctggtgtacagcaat aagtgtcagactcccctgggaatggcttctggacacattagagattttca gattacagcttcaggacaatatggacagtgggccccaaagctggccagac ttcattattccggatcaatcaatgcctggagcaccaaggagccctttct tggatcaaggtggatctgttggcaccaatgattattcacggcatcaagac ccagggtgcccgtcagaagttctccagcctctacatctctcagtttatca tcatgtatagtcttgatgggaagaagtggcagacttatcgaggaaattcc actggaaccttaatggtcttctttggcaatgtggattcatctgggataaa acacaatattttaaccctccaattattgctcgatacatccgtttgcacc caactcattatagcattcgcagcactcttcgcatggagttgatgggctgt gatttaaatagttgcagcatgccattgggaatggagagtaaagcaatatc agatgcacagattactgcttcatcctacttttaccaatatgtttgccacct ggtctccttcaaaagctcgacttcacctccaagggaggagtaatgcctgg agacctcaggtgaataatccaaaagagtggctgcaagtggacttccagaa gacaatgaaagtcacaggagtaactactcagggagtaaaatctctgctta ccagcatgtatgtgaaggagttcctcatctccagcagtcaagatggccat cagtggactctcttttcagaatggcaaagtaaaggtttttcagggaaa tcaagactccttcacacctgtggtgaactctctagacccaccgttactga ctcgctaccttcgaattcaccccagagttgggtgcaccagattgccctg aggatggaggttctgggctgcgaggcacaggacctctactga
```

The wild-type human factor VIII encoded by SEQ ID NO: 1 has an amino acid sequence of SEQ ID NO:2, as follows:

ATRRYYLGAVELSWDYMQSDLGELPVDARFPPRVPKSFPFNTSVVYKKTL

FVEFTVHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVNRSLPGLIGCHR

KSVYWHVIGMGTTPEVHSIFLEGHTFLVRNHRQASL<u>E</u>ISPITFLTAQTLL

M<u>D</u>LGQFLLGCHISSHQHDGMEAYVKVDSCPEEPQLRMKNNEEAEDYDDDL

TDSEMDVVRFDDDNSPSFIQIRSVAKKHPKTWVHYIAAEEEDWDYPALVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPILPGEIFKYKWTVTVE<u>D</u>GPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVY<u>E</u>DTLTLFPFSGETVFMSMENPGLWILGCHNSDFRNR

GMTALLKVSSCDKNTGDYYEDSYEDISAYLLSKNNAIEPRSFSQNSRHPS

TRQKQFNATTIPENDIEKTDPWFAHRTPMPKIQNVSSSDLLMLLRQSPTP

HGLSLSDLQEAKYETFSDDPSPGAIDSNNSLSEMTHFRPQLHHSGDMVFT

PESGLQLRLNEKLGTTAATELKKLDFKVSSTSNNLISTIPSDNLAAGTDN

TSSLGPPSMPVHYDSQLDTTLFGKKSSPLTESGGPLSLSEENNDSKLLES

GLMNSQESSWGKNVSSTESGRLFKGKRAHGPALLTKDNALFKVSISLLKT

NKTSNNSATNRKTHIDGPSLLIENSPSVWQNILESDTEFKKVTPLIHDRM

LMDKNATALRLNHMSNKTTSSKNMEMVQQKKEGPIPPDAQNPDMSFFKML

FLPESARWIQRTHGKNSLNSGQGPSPKQLVSLGPEKSVEGQNFLSEKNKV

VVGKGEFTKDVGLKEMVFPSSRNLFLTNLDNLHENNTHNQEKKIQEEIEK

KETLIQENVVLPQIHTVTGTKNFMKNLFLLSTRQNVEGSYEGAYAPVLQD

FRSLNDSTNRTKKHTAHFSKKGEEENLEGLGNQTKQIVEKYACTTRISPN

TSQQNFVTQRSKRALKQFRLPLEETELEKRIIVDDTSTQWSKNMKHLTPS

TLTQIDYNEKEKGAITQSPLSDCLTRSHSIPQANRSPLPIAKVSSFPSIR

PIYLTRVLFQDNSSHLPAASYRKKDSGVQESSHFLQGAKKNNLSLAILTL

EMTGDQREVGSLGTSATNSVTYKKVENTVLPKPDLPKTSGKVELLPKVHI

YQKDLFPTETSNGSPGHLELVEGSLLQGTEGAIKWNEANRPGKVPFLRVA

TESSAKTPSKLLDPLAWDNHYGTQUPKEEWKSQEKSPEKTAFKKKDTILS

LNACESNHAIAAINEGQNKPEIEVTWASQGRTERLCSQNPPVLKRHQREI

TRTTLQSDQEEIDYDDTISVEMKKEDFDIYDEDENQSPRSFQKKTRHYFI

AAVERLWDYGMSSSPHVLRNRAQSGSVPQFKKVVFQEFTDGSFTQPLYRG

ELNEHLGLLGPYIRAEVEDNIMNTFRNQASRPYSFYSSLISYEEDQRQGA

EPRKNFVKPNETKTYFWKVQHHMAPTKDEFDCKAWAYFSDVDLEKDVHSG

LIGPLLVCHTNTLNPAHGRQVTVQEFALFFTIFDETKSWYFTENMERNCR

APCNIQMEDPTFKENYRFHAINGYIMDTLPGLVMAQDQRIRWYLLSMGSN

ENIHSIHFSGHVFTVRKKEEYKMALYNLYPGVF<u>E</u>TVMELPSKAGIWRVEV

LIGEHLHAGMSTLFLVYSNKCQTPLGMASGHIRDFQITASGQYGQWAPKL

ARLHYSGSINAWSTKEPFSWIKVDLLAPMIIHGIKTQGARQKFSSLYISQ

FIIMYSLDGKKWQTYRGNSTGTLMVFFGNVDSSGIKHNIFNPPIIARYIR

LHPTHYSIRSTLRMELMGCDLNSCSMPLGMESKAISDAQITASSYFTNMF

ATWSPSKARLHLQGRSNAWRPQVNNPKEWLQVDFQKTMKVTGVTTQGVKS

LLTSMYVKEFLISSSQDGHQWTLFFQNGKVKVFQGNQDSFTPVVNSLDPP

LLTRYLRISPQSWVHQIALRMEVLGCEAQDLY

In the above sequences several charged residues are identified by bold typeface and underlining, including Glu287, Asp302, Asp519, Glu665, and Glu1984

The recombinant factor VIII of the present invention is characterized by the replacement of one or more charged amino acid residues with a hydrophobic amino acid residue at either or both of the A1 A2 or A2A3 domain interfaces. Preferably, the charged residue to be replaced is either a Glu or Asp residue that does not participate in hydrogen bonding between the A1 A2 or A2A3 domains. The hydrophobic amino acid residue that replaces the charged residue can be any of Ala, Val, Ile, Leu, Met, Phe, or Trp. Particularly preferred recombinant factor VIII of the present invention includes a substitution of the Glu287 residue of wildtype factor VIII, a substitution of the Asp302 residue of wildtype factor VIII, a substitution of the Asp519 residue of wildtype factor VIII, a substitution of the Glu665 residue of wildtype factor VIII, a substitution of the Glu1984 residue of wildtype factor VIII, or combinations thereof. The D302A, E287A, E665A, E665V, D519A, D519V, E1984A, and E1984V substitutions are preferred for achieving a recombinant factor VIII that has enhanced stability of both factor VIII and factor VIIIa. Preferred combinations of these substitutions include, without limitation, D519AF665V, D519VE665V, and D519VE1984A double mutants, as well as D519AE665VE1984A and D519VE665VE1984A triple mutants. The enhanced stability of these mutants is believed to be achieved by stabilizing the inter-domain interface in factor VIII as well as reducing A2 subunit dissociation from A1/A3C1C2 as compared to wildtype factor VIIIa.

Suitable mutant factor VIII sequences that can be modified in accordance with the present invention can also include any previously known or subsequently identified mutant factor VIII sequences that have modified properties with regard to various attributes, including, without limitation, antigenicity, circulating half-life, protein secretion, affinity for factor IXa and/or factor X, altered factor VIII-inactivation cleavage sites, enhanced specific activity of factor VIIIa, immunogenicity, and shelf-life.

One example of a suitable mutant factor VIII that can be modified in accordance with the present invention is a factor VIII having a modified calcium binding site, preferably at residue 113 of SEQ ID NO: 2. This affords a factor VIIIa having enhanced specific activity. Exemplary mutants of this type are described in U.S. patent application Ser. No. 10/581,471 to Fay et al., which is hereby incorporated by reference in its entirety. Preferably, the residue 113 mutant also is modified in accordance with one or more of the mutations described above (e.g., at positions 287, 302, 519, 665, and/or 1984) to afford a high stability/high specific activity factor VIII protein. Exemplary high stability/high specific activity factor VIII proteins include, without limitation: those possessing combined E113AD519A, E113AD519V, E113AE665A, E113AE665V, or E113AE1984V substitutions.

A second example of a suitable mutant factor VIII that can be modified in accordance with the present invention is a B-domainless factor VIII that contains amino acid residues 1-740 and 1690-2332 of SEQ ID NO: 2 (see, e.g., U.S. Pat. No. 6,458,563 to Lollar, which is hereby incorporated by reference in its entirety).

In one embodiment of the B-domainless recombinant factor VIII of the present invention, the B-domain is replaced by a DNA linker segment and at least one codon is replaced with a codon encoding an amino acid residue that has the same charge as a corresponding residue of porcine factor VIII (see, e.g., U.S. Patent Application Publication No. 2004/0197875 to Hauser et al., which is hereby incorporated by reference in its entirety).

In another embodiment of the B-domainless recombinant factor VIII of the present invention, the modified mutant factor VIII is encoded by a nucleotide sequence having a truncated factor IX intron 1 inserted in one or more locations (see, e.g., U.S. Pat. No. 6,800,461 to Negrier and U.S. Pat. No. 6,780,614 to Negrier, each of which is hereby incorporated by reference in its entirety). This recombinant factor VIII can be used for yielding higher production of the recombinant factor VIII in vitro as well as in a transfer vector for gene therapy (see, e.g., U.S. Pat. No. 6,800,461 to Negrier, which is hereby incorporated by reference in its entirety). In a particular example of this embodiment, the recombinant factor VIII can be encoded by a nucleotide sequence having a truncated factor IX intron 1 inserted in two locations, and having a promoter that is suitable for driving expression in hematopoietic cell lines, and specifically in platelets (see, e.g., U.S. Pat. No. 6,780,614 to Negrier, which is hereby incorporated by reference in its entirety).

Regardless of the embodiment, the B-domainless factor VIII preferably contains one or more of the mutations described above (e.g., at positions 287, 302, 519, 665, and/or 1984). Recombinant factor VIII proteins prepared in accordance with the Examples herein are B-domainless.

A third example of a suitable mutant factor VIII that can be modified in accordance with the present invention is a chimeric human/animal factor VIII that contains one or more animal amino acid residues as substitution(s) for human amino acid residues that are responsible for the antigenicity of human factor VIII. In particular, animal (e.g., porcine) residue substitutions can include, without limitation, one or more of the following: R484A, R488G, P485A, L486S, Y487L, Y487A, S488A, S488L, R489A, R489S, R490G, L491S, P492L, P492A, K493A, G494S, V495A, K496M, H497L, L498S, K499M, D500A, F501A, P502L, 1503M, L504M, P505A, G506A, E507G, I508M, I508A, M2199I, F2200L, L2252F, V2223A, K2227E, and/or L2251 (U.S. Pat. No. 5,859,204 to Lollar, U.S. Pat. No. 6,770,744 to Lollar, and U.S. Patent Application Publication No. 2003/0166536 to Lollar, each of which is hereby incorporated by reference in its entirety). Preferably, the recombinant chimeric factor VIII contains one or more of the mutations described above (e.g., at positions 287, 302, 519, 665, and/or 1984).

A fourth example of a suitable mutant factor VIII that can be modified in accordance with the present invention is a factor VII that has enhanced affinity for factor IXa (see, e.g., Fay et al., "Factor VIIIa A2 Subunit Residues 558-565 Represent a Factor IXa Interactive Site," J. Biol. Chem. 269(32): 20522-7 (1994); Bajaj et al., "Factor IXa: Factor VIIIa Interaction. Helix 330-338 of Factor IXa Interacts with Residues 558-565 and Spatially Adjacent Regions of the A2 Subunit of Factor VIIIa," J. Biol. Chem. 276(19):16302-9 (2001); and Lenting et al., "The Sequence Glu1811-Lys1818 of Human Blood Coagulation Factor VIII Comprises a Binding Site for Activated Factor IX," J. Biol. Chem. 271(4), 193540 (1996), each of which is hereby incorporated by reference in its entirety) and/or factor X (see, e.g., Lapan et al., "Localization of a Factor X Interactive Site in the A1 Subunit of Factor VIIIa," J. Biol./Chem. 272:2082-88 (1997), which is hereby incorporated by reference in its entirety). Preferably, the enhanced-affinity factor VIII contains one or more of the mutations described above (e.g., at positions 287, 302, 519, 665, and/or 1984).

A fifth example of a suitable mutant factor VIII that can be modified in accordance with the present invention is a factor VIII that is modified to enhance secretion of the factor VIII (see, e.g., Swaroop et al., "Mutagenesis of a Potential Immunoglobulin-Binding Protein-Binding Site Enhances Secretion of Coagulation Factor VIII," J. Biol. Chem. 272(39): 24121-4 (1997), which is hereby incorporated by reference in its entirety). Preferably, the secretion enhanced mutant factor VIII contains one or more of the mutations identified above (e.g., at positions 287, 302, 519, 665, and/or 1984).

A sixth example of a suitable mutant factor VIII that can be modified in accordance with the present invention is a factor VIII with an increased circulating half-life. This modification can be made using various approaches, including, without limitation, by reducing interactions with heparan sulfate (Sarafanov et al., "Cell Surface Heparan Sulfate Proteoglycans Participate in Factor VIII Catabolism Mediated by Low Density Lipoprotein Receptor-Related Protein," *J. Biol. Chem.* 276(15):11970-9 (2001), which is hereby incorporated by reference in its entirety) and/or low-density lipoprotein receptor-related protein (4"LRP") (Saenko et al., "Role of the Low Density Lipoprotein-Related Protein Receptor in Mediation of Factor VIII Catabolism," *J. Biol. Chem.* 274 (53):37685-92 (1999); and Lenting et al., "The Light Chain of Factor VIII Comprises a Binding Site for Low Density Lipoprotein Receptor-Related Protein," *J. Biol. Chem.* 274(34): 23734-9 (1999), each of which is hereby incorporated by reference in its entirety). Preferably, the half-life enhanced mutant factor VIII contains one or more of the mutations described above (e.g., at positions 287, 302, 519, 665, and/or 1984).

A seventh example of a suitable mutant factor VIII that can be modified in accordance with the present invention is a modified factor VIII encoded by a nucleotide sequence modified to code for amino acids within known, existing epitopes to produce a recognition sequence for glycosylation at asparagines residues (see, e.g., U.S. Pat. No. 6,759,216 to Lollar, which is hereby incorporated by reference in its entirety). The mutant factor VIII of this example can be useful in providing a modified factor VIII that escapes detection by existing inhibitory antibodies (low antigenicity factor VIII) and which decreases the likelihood of developing inhibitory antibodies (low immunogenicity factor VIII). In one particular embodiment of this example, the modified factor VIII is mutated to have a consensus amino acid sequence for N-linked glycosylation. An example of such a consensus sequence is N-X-S/T, where N is asparagine, X is any amino acid, and S/T stands for serine or threonine (see U.S. Pat. No. 6,759,216 to Lollar, which is hereby incorporated by reference in its entirety). Preferably, the glycosylation site-modified factor VIII contains one or more of the mutations identified above (e.g., at positions 287, 302, 519, 665, and/or 1984).

An eighth example of a suitable mutant factor VIII that can be modified in accordance with the present invention is a modified factor VIII that is a procoagulant-active factor VIII having various mutations (see, e.g., U.S. Patent Application Publication No. 2004/0092442 to Kaufman et al., which is hereby incorporated by reference in its entirety). One example of this embodiment relates to a modified factor VIII that has been modified to (i) delete the von Willebrand factor binding site, (ii) add a mutation at Arg 740, and (iii) add an amino acid sequence spacer between the A2- and A3-domains, where the amino acid spacer is of a sufficient length so that upon activation, the procoagulant-active factor VIII protein becomes a heterodimer (see U.S. Patent Application Publication No. 2004/0092442 to Kaufman et al., which is hereby incorporated by reference in its entirety). Preferably, procoagulant active factor VIII is also modified to contain one or more of the mutations described above (e.g., at positions 287, 302, 519, 665, and/or 1984).

Further, the mutant factor VIII can be modified to take advantage of various advancements regarding recombinant coagulation factors generally (see, e.g., Saenko et al., "The Future of Recombinant Coagulation Factors," *J. Thrombosis and Haemostasis* 1:922-930 (2003), which is hereby incorporated by reference in its entirety).

The recombinant factor VIII of the present invention can be modified at any charged residue that destabilizes the A1A2 or A2A3 domain interfaces (including positions 287, 302, 519, 665, or 1984), as well as be modified to be B-domainless, to be chimeric, to have modified calcium binding sites that enhance factor VIIIa activity (e.g., at position 113), to have altered inactivation cleavage sites, to have enhanced factor IXa and/or factor X affinity, to have enhanced secretion, to have an increased circulating half-life, or to have mutant glycosylation sites; or to possess any one or more of such modifications in addition to the one or more modifications to charged residues, including a modified calcium-binding site that improves activity of the recombinant factor VIII. A number of exemplary B-domainless, enhanced specific activity, high stability recombinant factor VIII proteins are described in the Examples.

The recombinant factor VIII is preferably produced in a substantially pure form. In a particular embodiment, the substantially pure recombinant factor VIII is at least about 80% pure, more preferably at least 90% pure, most preferably at least 95% pure. A substantially pure recombinant factor VIII can be obtained by conventional techniques well known in the art. Typically, the substantially pure recombinant factor VIII is secreted into the growth medium of recombinant host cells. Alternatively, the substantially pure recombinant factor VIII is produced but not secreted into growth medium. In such cases, to isolate the substantially pure recombinant factor VIII, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure recombinant factor VIII is subjected to gel filtration in an appropriately sized dextran or polyacrylamide column to separate the recombinant factor VIII. If necessary, a protein fraction (containing the substantially pure recombinant factor VIII) may be further purified by high performance liquid chromatography ("HPLC").

Another aspect of the present invention relates to an isolated nucleic acid molecule that encodes the recombinant factor VIII of the present invention. The isolated nucleic acid molecule encoding the recombinant factor VIII can be either RNA or DNA.

In one embodiment, the isolated nucleic acid molecule can have a nucleotide sequence encoding a mutation at position 113 that enhances factor VIII specific activity, as modified with one or more of the substitutions of charged residues (e.g., at positions 287, 302, 519, 665, 1984, and/or 332-340 of SEQ ID NO: 2).

In another embodiment, the isolated nucleic acid molecule can have a nucleotide sequence encoding a B-domainless factor VIII of the type described above, as modified with one or more of the substitutions of charged residues (e.g., at positions 287, 302, 519, 665, and/or 1984 of SEQ ID NO:2).

In another embodiment, the isolated nucleic acid molecule can have a nucleotide sequence encoding a chimeric human/porcine of the type described above, as modified with one or more of the substitutions of charged residues (e.g., at positions 287, 302, 519, 665, and/or 1984 of SEQ ID NO:2).

In another embodiment, the isolated nucleic acid molecule can have a nucleotide sequence encoding a factor VIII whose inactivation sites have been modified as described above, as further modified with one or more of the substitutions of charged residues (e.g., at positions 287, 302, 519, 665, and/or 1984 of SEQ ID NO:2).

In yet another embodiment, the isolated nucleic acid molecule can have a nucleotide sequence encoding a factor VIII whose affinity for factor IXa and/or factor X has been enhanced, as further modified with one or more of the substitutions of charged residues (e.g., at positions 287, 302, 519, 665, and/or 1984 of SEQ ID NO:2).

In a still further embodiment, the isolated nucleic acid molecule can have a nucleotide sequence encoding a factor VIII whose affinity for various serum-binding proteins has been altered to increase its circulating half-life, as further modified with one or more of the substitutions of charged residues (e.g., at positions 287, 302, 519, 665, and/or 1984 of SEQ ID NO:2).

In a further embodiment, the isolated nucleic acid molecule can have a nucleotide sequence encoding a factor VIII that has increased secretion in culture, as further modified with one or more of the substitutions of charged residues (e.g., at positions 287, 302, 519, 665, and/or 1984 of SEQ ID NO:2).

In a further embodiment, the isolated nucleic acid molecule can have a nucleotide sequence encoding a factor VIII that possesses one or more non-naturally occurring glycosylation site, as further modified with one or more of the substitutions of charged residues (e.g., at positions 287, 302, 519, 665, and/or 1984 of SEQ ID NO:2).

In yet another embodiment, the isolated nucleic acid molecule encodes a recombinant factor VIII that is modified at any one or more charged residues as described above and is also modified to possess any two or more of the following: modified to be B-domainless, modified to be chimeric, modified to have altered inactivation cleavage sites, modified to have enhanced factor IXa and/or factor X affinity, modified to have enhanced secretion, modified to have an increased circulating half-life, modified to possess one or more non-naturally occurring glycosylation site, and modified within a calcium-binding site (e.g., at position 113) such that the specific activity of the recombinant factor VIII is improved.

Another aspect of the present invention relates to a recombinant DNA expression system that includes an isolated DNA molecule of the present invention, which expression system encodes a recombinant factor VIII. In one embodiment, the DNA molecule is in sense orientation relative to a promoter.

A further aspect of the present invention relates to a host cell including an isolated nucleic acid molecule encoding the recombinant factor VIII of the present invention. In a particular embodiment, the host cell can contain the isolated nucleic acid molecule in DNA molecule form, either as a stable plasmid or as a stable insertion or integration into the host cell genome. In another embodiment, the host cell can contain a DNA molecule in an expression system. Suitable host cells can be, without limitation, animal cells (e.g., baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), or algal cells.

The recombinant DNA expression system and host cells can be produced using various recombinant techniques well-known in the art, as further discussed below.

The DNA molecule encoding the recombinant factor VIII of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements for the transcription and translation of the inserted protein-coding sequences. Thus, one embodiment of the present invention provides a DNA construct containing the isolated nucleic acid of the present invention, which is operably linked to both a 5' promoter and a 3' regulatory region (i.e., transcription terminator) capable of affording transcription and expression of the encoded recombinant factor VIII of the present invention in host cells or host organisms.

With respect to the recombinant expression system of the present invention, an expression vector containing a DNA molecule encoding the recombinant factor VIII of the present invention can be made using common techniques in the art. The nucleic acid molecules of the present invention can be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

A variety of host-vector systems may be utilized to express the recombinant factor VIII-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, etc.); insect cell systems infected with virus (e.g. baculovirus); and plant cells infected by bacteria (e.g., *Agrobacterium*). The expression elements of these vectors vary in their strength and specificities. Depending upon the host-vector system utilized, any one of a number of suitable transcription and translation elements can be used.

When recombinantly produced, the factor VIII protein or polypeptide (or fragment or variant thereof) is expressed in a recombinant host cell, typically, although not exclusively, a eukaryote.

Suitable vectors for practicing the present invention include, but are not limited to, the following viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV 40, pbluescript II SK +/− or KS +/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology* 185:60-89 (1990), which is hereby incorporated by reference in its entirety), and any derivatives thereof. Any appropriate vectors now known or later described for genetic transformation are suitable for use with the present invention.

Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Harbor, N.Y.: Cold Springs Laboratory, (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *Escherichia coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon (4"ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one embodiment, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The DNA construct of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons (1989), each of which is hereby incorporated by reference in its entirety.

As noted, one alternative to the use of prokaryotic host cells is the use of eukaryotic host cells, such as mammalian cells, which can also be used to recombinantly produce the recombinant factor VIII of the present invention. Mammalian cells suitable for carrying out the present invention include, among others: COS (e.g., ATCC No. CRL 1650 or 1651), BHK (e.g., ATCC No. CRL 6281), CHO (e.g., ATCC No. CCL 61), HeLa (e.g., ATCC No. CCL 2), 293 (ATCC No. 1573), CHOP, and NS-1 cells.

Suitable expression vectors for directing expression in mammalian cells generally include a promoter, as well as other transcription and translation control sequences known in the art. Common promoters include SV40, MMTV, metallothionein-1, adenovirus E1a, CMV, immediate early, immunoglobulin heavy chain promoter and enhancer, and RSV-LTR.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation.

In view of the recombinant technology discussed herein, another aspect of the present invention relates to a method of making a recombinant factor VIII of the present invention. This method involves growing a host cell of the present invention under conditions whereby the host cell expresses the recombinant factor VIII. The recombinant factor VIII is then isolated. In one embodiment, the host cell is grown in vitro in a growth medium. In a particular embodiment, suitable growth media can include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the recombinant factor VIII. Once the recombinant factor VIII is secreted into the growth medium, it can then be isolated from the growth medium using techniques well-known by those of ordinary skill in the relevant recombinant DNA and protein arts (including those described herein). In another embodiment, the method of making the recombinant factor VIII of the present invention further involves disrupting the host cell prior to isolation of the recombinant factor VIII. In this embodiment, the recombinant factor VIII is isolated from cellular debris.

The modifications at positions 287, 302, 519, 665, and/or 1984 are particularly preferred, because they result in enhanced stability of both factor VIII and factor VIIIa. This increased stability is important with regard to circulating half-life of factor VIII and the activity of factor VIIIa during blood clotting. Furthermore, this property is significant in terms of enhancing the recovery of usable factor VIII during the purification and preparation of the protein for therapeutic use.

When an expression vector is used for purposes of in vivo transformation to induce factor VIII expression in a target cell, promoters of varying strength can be employed depending on the degree of enhancement desired. One of skill in the art can readily select appropriate mammalian promoters based on their strength as a promoter. Alternatively, an inducible promoter can be employed for purposes of controlling when expression or suppression of factor VIII is desired. One of skill in the art can readily select appropriate inducible mammalian promoters from those known in the art. Finally, tissue specific mammalian promoters can be selected to restrict the efficacy of any gene transformation system to a particular tissue. Tissue specific promoters are known in the art and can be selected based upon the tissue or cell type to be treated.

Another aspect of the present invention relates to a method of treating an animal for a blood disorder such as hemophilia, particularly hemophilia A. This method involves administering to an animal exhibiting hemophilia A an effective amount of the recombinant factor VIII of the present invention, whereby the animal exhibits effective blood clotting following vascular injury. A suitable effective amount of the recombinant factor VIII can include, without limitation, between about 10 to about 50 units/kg body weight of the animal. The animal can be any mammal, but preferably a human, a rat, a mouse, a guinea pig, a dog, a cat, a monkey, a chimpanzee, an orangutan, a cow, a horse, a sheep, a pig, a goat, or a rabbit.

The recombinant factor VIII of the present invention can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. In a particular embodiment, the recombinant factor VIII, alone, or in the form of a pharmaceutical composition (i.e., in combination with stabilizers, delivery vehicles, and/or carriers) is infused into patients intravenously according to the same procedure that is used for infusion of human or animal factor VIII.

Alternatively, or in addition thereto, the recombinant factor VIII can be administered by administering a viral vector such as an adeno-associated virus (Gnatenko et al., "Human Factor VIII Can Be Packaged and Functionally Expressed in an Adeno-associated Virus Background: Applicability to Hemophilia A Gene Therapy," *Br. J. Haematol.* 104:27-36 (1999), which is hereby incorporated by reference in its entirety), or by transplanting cells genetically engineered to produce the recombinant factor VIII, typically via implantation of a device containing such cells. Such transplantation typically involves using recombinant dermal fibroblasts, a non-viral approach (Roth et al., "Nonviral Transfer of the Gene Encoding Coagulation Factor VIII in Patients with Sever Hemophilia," *New Engl. J. Med.* 344; 1735-1742 (2001), which is hereby incorporated by reference in its entirety).

The treatment dosages of recombinant factor VIII that should be administered to a patient in need of such treatment will vary depending on the severity of the factor VIII deficiency. Generally, dosage level is adjusted in frequency, duration, and units in keeping with the severity and duration of each patient's bleeding episode. Accordingly, the recombinant factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of recombinant factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al., "Recombinant Factor VIII for the Treatment of Previously Untreated Patients with Hemophilia A—Safety, Efficacy, and Development of Inhibitors," *New Engl. J. Med.* 328:453-459 (1993); Pittman et al., "A2 Domain of Human Recombinant-derived Factor VIII is Required for Procoagulant Activity but not for Thrombin Cleavage," *Blood* 79:389-397 (1992); and Brinkhous et al., "Purified Human Factor VIII Procoagulant Protein Comparative Hemostatic Response After Infusions into Hemophilic and von Willebrand Disease Dogs," *Proc. Natl. Acad. Sci.* 82:8752-8755 (1985), which are hereby incorporated by reference in their entirety.

Usually, the desired plasma factor VIII activity level to be achieved in the patient through administration of the recombinant factor VIII is in the range of 30-100% of normal. In one embodiment, administration of the therapeutic recombinant factor VIII is given intravenously at a preferred dosage in the range from about 5 to 50 units/kg body weight, and particularly in a range of 10-50 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts and Jones, "Hemophilia and Related Conditions—Congenital Deficiencies of Prothrombin (Factor II, Factor V, and Factors VII to XII)," *Ch.* 153, 1453-1474, 1460, in *Hematology*, Williams, W. J., et al., ed. (1990), which is hereby incorporated by reference in its entirety. Patients with inhibitors may require a different amount of recombinant factor VIII than their previous form of factor VIII. For example, patients may require less recombinant factor VIII because of its higher specific activity than the wild-type VIII and its decreased antibody reactivity. As in treatment with human or plasma-derived factor VIII, the amount of therapeutic recombinant factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed recombinant factor VIII.

Treatment can take the form of a single intravenous administration of the recombinant factor VIII or periodic or continuous administration over an extended period of time, as required. Alternatively, therapeutic recombinant factor VIII can be administered subcutaneously or orally with liposomes in one or several doses at varying intervals of time.

The recombinant factor VIII can also be used to treat uncontrolled bleeding due to factor VIII deficiency in hemophiliacs who have developed antibodies to human factor VIII.

It has been demonstrated herein that the recombinant factor VIII of the present invention can differ in specific activity from the wild-type factor VIII. Factor VIII proteins having greater procoagulant activity from wild-type factor VIII are useful in treatment of hemophilia because lower dosages will be required to correct a patient's factor VIII deficiency. This will not only reduce medical expense for both the patient and the insurer, but also reduce the likelihood of developing an immune response to the factor VIII (because less antigen is administered).

EXAMPLES

The following examples are provided to illustrate embodiments of the present invention but they are by no means intended to limit its scope.

Materials & Methods

Reagents

Recombinant factor VIII (Kogenate™) was a generous gift from Dr. Lisa Regan of Bayer Corporation (Berkeley, Calif.). Phospholipid vesicles containing 20% phosphatidylcholine (PC), 40% phosphatidylethanolamine (PE), and 40% phosphatidylserine (PS) were prepared using octylglucoside as described previously (Mimms et al., "Phospholipid Vesicle Formation and Transmembrane Protein Incorporation Using Octyl Glucoside," *Biochemistry* 20:833-840 (1981), which is hereby incorporated by reference in its entirety). The reagents α-thrombin, factor VIIa, factor IXaβ, factor X, and factor Xa (Enzyme Research Laboratories, South Bend, 1N), hirudin and phospholipids (DiaPharma, West Chester, Ohio), the chromogenic Xa substrate, Pefachrome Xa (Pefa-5523, $CH_3OCO$-D-CHA-Gly-Arg-pNA-AcOH; Centerchem Inc. Norwalk Conn.), recombinant human tissue factor (rTF), Innovin (Dade Behring, Newark, Del.), fluorogenic substrate, Z-Gly-Gly-Arg-AMC (Calbiochem, San Diego, Calif.), and thrombin calibrator (Diagnostica Stago, Parsippany, N.J.) were purchased from the indicated vendors.

Construction, Expression and Purification of WT and Variant Factor VIII:

Ala mutants (at D27, H281, R282, E287, D302, S313, H317, T522, S524, R531, N538, E540, S650, S654, D666, ±683, N684, S695, 9696, S1791, D1795, Q1820, E1829, S1949, N1950, and R1966); Phe mutants (at Y476, Y664, Y1786, and Y1792); Ala and Val mutants (at charged residues E272, D519, E665, and E1984); and WT factor VIII forms were individually constructed as a B-domainless factor VIII, lacking residues Gin744-Ser1637 in the B-domain (Doering et al., "Expression and Characterization of Recombinant Murine Factor VIII," *Thromb Haemost.* 88:450-458 (2002), which is hereby incorporated by reference in its entirety). The cloning and expression constructs were generous gifts from Dr. Pete Lollar and John Healey. Recombinant WT and variant factor VIII forms were stably expressed in BHK cells and purified as described previously (Wakabayashi et al., "Residues 110-126 in the A1 Domain of Factor VIII Contain a $Ca^{2+}$ Binding Site Required for Cofactor Activity," *J Biol Chem.* 279:12677-12684 (2004), which is hereby incorporated by reference in its entirety). After transfection there were no significant differences in the amounts of factor VIII secretion among the variants. Protein yields for the variants ranged from >10 to ~100 μg from two 750 $cm^2$ culture flasks, with purity from ~85% to >95% as judged by SDS-PAGE. The primary contaminant in the factor VIII preparations was albumin and at the concentrations present in the factor VIII showed no effect on stability of activity parameters. Factor VIII concentration was measured using an Enzyme-Linked Immunoadsorbant Assay (ELISA) and factor VIII activity was determined by an one-stage clotting assay and a two-stage chromogenic factor Xa generation assay as described below.

SDS-PAGE and Western Blotting

Factor VIII proteins (0.77 μg for gel staining and 0.34 μg for Western blot) were electrophoresed on 8% polyacrylamide gel at constant voltage (100V). Gels were stained with Gelcode Blue (Thermo Scientific, Rockford, Ill.) or transferred to a polyvinylidene fluoride membrane and probed with biotinylated anti-A2 antibody (R8B12, Green Mountain Antibodies, Burlington, Vt.) followed by the incubation with peroxidase-conjugated streptoavidin (Calbiochem, San Diego, Calif.). The chemifluorescence substrate (ECF substrate, GE Healthcare, Piscataway, N.J.) was reacted and the fluorescence signal scanned using a phosphoimager (Storm 860, GE Healthcare), The density of single chain factor VIII form (170 kDa) and heavy chain (HC, 90 kDa) were quantified using ImageQuant software (GE Healthcare) and the amount ratios were calculated.

ELISA

A sandwich ELISA was performed to measure the concentration of factor VIII proteins as previously described (Wakabayashi et al., "A Glu113Ala Mutation within a Factor VIII $Ca^{2+}$-Binding Site Enhances Cofactor Interactions in Factor Xase," *Biochemistry* 44:10298-10304 (2005), which is hereby incorporated by reference in its entirety) using purified commercial recombinant factor VIII (Kogenate, Bayer Corporation) as a standard. Factor VIII capture used the anti-C2 antibody (ESH-8, American Diagnostica Inc., Stamford, Conn.) and a biotinylated R8B12 antibody, was employed for factor VIII detection.

One-stage Clotting Assay

One-stage clotting assays were performed using substrate plasma chemically depleted Of factor VII (Over, "Methodology of the One-stage Assay of Factor VIII (VIII:C)," *Scand J Haematol Suppl.* 41:13-24 (1984), which is hereby incorporated by reference in its entirety) and assayed using a Diagnostica Stago clotting instrument. Plasma was incubated with APTT reagent (General Diagnostics) for 6 min at 37° C. after which a dilution of factor VIII was added to the cuvette. After 1 min the mixture was recalcified, and clotting time was determined and compared to a pooled normal plasma standard.

Two-Stage Chromogenic Factor Xa Generation Assay

The rate of conversion of factor X to factor Xa was monitored in a purified system (Lollar et al., "Factor VIII and Factor VIIIa," *Methods Enzymol.* 222:128-143 (1993), which is hereby incorporated by reference in its entirety) according to methods previously described (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001); Wakabayashi et al., "$Ca^{2+}$ Binding to Both the Heavy and Light Chains of Factor VIII Is Required for Cofactor Activity," *Biochemistry* 41:8485-8492 (2002), each of which is hereby incorporated by reference in its entirety). Factor VIII (1 nM) in buffer containing 20 mM N-[2-hydroxyethyl] piperazine-N'-[2-ethanesulfonic acid] (HEPES), pH 7.2, 0.1 M NaCl, 0.01% Tween 20, 0.01% BSA, 5 mM $CaCl_2$, and 10 µM PSPCPE vesicles (Buffer A) was activated with 20 nM α-thrombin for 1 min. The reaction was stopped by adding hirudin (10 U/ml) and the resulting factor VIIIa was reacted with factor IXa (40 nM) for 1 min. Factor X (300 µM) was added to initiate reactions which were quenched after 1 min by the addition of 50 mM EDTA. Factor Xa generated was determined following reaction with the chromogenic substrate Pefachrome Xa (0.46 mM final concentration). All reactions were run at 23° C.

Thrombin Generation Assay

The amount of thrombin generated in plasma was measured by Calibrated Automated Thrombography (Hemker et al., "Calibrated Automated Thrombin Generation Measurement in Clotting Plasma," *Pathophysiol Haemost Thromb.* 33:4-15 (2003); Hemker et al., "Thrombin Generation in Plasma: Its Assessment via the Endogenous Thrombin Potential," *Thromb Haemost.* 74:134-138 (1995), each of which is hereby incorporated by reference in its entirety). In a 96-well plate, 80 µl of factor VIII deficient plasma (<1% residual activity, platelet-poor) from severe hemophilia A patient lacking factor VIII inhibitor (George King Bio-Medical, Overland Park, Kans.) was mixed with factor VIII samples (20 µl; 6 nM) in HEPES-BSA buffer (20 mM HEPES, pH 7.35, 0.15 M NaCl, 6% BSA) containing 3 pM rTF (the concentration of rTF stock was determined by factor Xa generation assay using known concentrations of factor VIIa), PSPCPE vesicles (24 µM) or 20 µl thrombin calibrator (630 nM) and reactions were immediately started by mixing with 20 µl fluorogenic substrate (2.5 mM, Z-Gly-Gly-Arg-AMC) in HEPES-BSA buffer including 0.1 M $CaCl_2$. All reagents were pre-warmed at 37° C. Final concentrations of reagents were 1 nM factor VIII (except as otherwise noted), 0.5 pM rTF, 4 µM PSPCPE vesicles, 433 µM fluorogenic substrate, 13.3 mM $CalCl_2$, and 105 nM thrombin calibrator. The development of a fluorescent signal at 37° C. was monitored at 8 second intervals using a Microplate Spectrofluorometer (Spetramax Gemini, Molecular Devices, Sunnyvale, Calif.) with a 355 nm (excitation)/460 nm (emission) filter set. Fluorescent signals were corrected by the reference signal from the thrombin calibrator samples (Hemker et al., "Calibrated Automated Thrombin Generation Measurement in Clotting Plasma," *Pathophysiol Haemost Thromb.* 33:4-15 (2003), each of which is hereby incorporated by reference in its entirety) and actual thrombin generation in nM was calculated as previously described (Hemker et al., "Thrombin Generation in Plasma: Its Assessment via the Endogenous Thrombin Potential," *Thromb Haemost.* 74:134-138 (1995), which is hereby incorporated by reference in its entirety).

Factor VIII Activity at Elevated Temperature

WT factor VIII or factor VIII variants (4 nM) in buffer A were incubated at 52-60° C. Aliquots were removed at the indicated times and residual factor VIII activity was determined using a two-stage chromogenic factor Xa generation assay.

Factor VIIIa Activity Time Course

WT and mutant factor VIII (4 nM) in buffer A containing 10 µM PSPCPE vesicles were activated by 20 nM thrombin for 1 min at 23° C. Reactions were immediately quenched by hirudin (10 U/ml), aliquots removed at the indicated times, and activity was determined using the factor Xa generation assay following addition of factor IXa (40 nM) and factor X (300 nM). For decay measurements run in the presence of factor IXa, factor IXa (40 nM) was added to reactions prior to thrombin addition.

Factor VIII Stability in Plasma

WT or variant factor VIII (1 nM) was added to factor VIII deficient plasma (<1% residual activity) from severe hemophilia A patient lacking factor VIII inhibitor (George King Bio-Medical). Plasma was supplemented with 0.02% $NaN_3$ to prevent the growth of microorganisms and samples were incubated at 37° C. Aliquots were removed at the indicated times and residual activity was determined by a one-stage clotting assay.

Data Analysis

Factor VIIIa activity values as a function of time were fitted to a single exponential decay curve by non-linear least squares regression using the equation, $$A = A_0 \times e^{-k \cdot 1}$$

where A is residual factor VIIIa activity (nM/min/nM factor VIII), $A_0$ is the initial activity, k is the apparent rate constant, and t is the time (minutes) of reaction of either factor VIII at elevated temperature (for factor VIII decay experiments) or after thrombin activation was quenched (for factor VIIIa decay measurements). Nonlinear least-squares regression analysis was performed by Kaleidagraph (Synergy, Reading, Pa.). Comparison of average values was performed by the Student's t-test. The factor VIII A domain modeled structure (Pemberton et al., "A Molecular Model for the Triplicated A Domains of Human Factor VIII Based on the Crystal Structure of Human Ceruloplasmin," *Blood* 89:2413-2421 (1997), which is hereby incorporated by reference in its entirety) was analyzed using Swiss PDB Viewer to identify charged residues that were located at the A2 domain interface and that showed little potential for hydrogen bonding interactions based on a threshold of >2.8 Å separating the polar atoms of the complementary domains (Weiner et al., "A New Force Field for Molecular Mechanical Simulation of Nucleic Acids Proteins," *J Am Chem Soc.* 106:765-784 (1984), which is hereby incorporated by reference in its entirety).

Example 1

Activity Values for Factor VIII Mutants Targeting Hydrogen Bonding Interactions

Bonding interactions involving the A2 domain in factor VIII remain poorly understood yet represent a primary mechanism for the regulation of cofactor activity. The factor VIII homology model (Pemberton et al., "A Molecular Model for the Triplicated A Domains of Human Factor VIII Based on the Crystal Structure of Human Ceruloplasmin," *Blood* 89:2413-2421 (1997), which is hereby incorporated by reference in its entirety) identifies the potential for many hydrogen bonds linking residues in the A2 domain with those in the A1 or A3 domains. Using a criterion for a spatial separation of <2.8 Å between hydrogen donor and acceptor atoms (Weiner et al., "A New Force Field for Molecular Mechanical Simulation of Nucleic Acids Proteins," *J Am Chem Soc.* 106:765-784 (1984), which is hereby incorporated by reference in its entirety) thirty residues were identified as having a side chain atom that may be involved in hydrogen bonding with an atom from a complementary A domain (see Table 1 below). In approximately half of the residues identified, side chain atoms were juxtaposed with either backbone carbonyl oxygen or amide hydrogen atoms, while the remainder represented possible interactions between neighboring side chains. Target residues in the factor VIII A domains were individually mutated to Ala, with the exception that Tyr residues were replaced with Phe, and the point mutations were stably expressed as B-domainless factor VIII.

Factor VIII activity was measured for the purified proteins using a one-stage clotting assay and a (two-stage) factor Xa generation assay. Results from the one-stage assay (FIG. 1) indicated that 9 of the 30 point mutants showed <50% activity relative to WT factor VIII. Five of these variants demonstrated a one-stage/two stage assay discrepancy (>1.5 fold difference), with three mutants (S524A, H281A, and E287A) showing reduction in only the two-stage assay. The reduced activity values for mutation in several targeted residues were consistent with a contribution of those side chains to the structural stability of factor VIII and/or factor VIIIa.

TABLE 1

Amino Acid Residues Capable of Hydrogen Bonding

| Residue (Atom) | Domain | Paired Residue (Atom) | Domain | Distance (Å) |
|---|---|---|---|---|
| D27 ($O_\delta$) | A1 | N538 ($H_\delta$) | A2 | 2.16 |
| H281 ($N_\delta$) | A1 | S524 ($H_\gamma$) | A2 | 2.12 |
| R282 ($H_\eta$) | A1 | G520 ($CO^a$) | A2 | 2.02 |
| E287 ($H_\epsilon$) | A1 | P672 (CO) | A2 | 1.79 |
| D302 ($H_\delta$) | A1 | D482 (CO) | A2 | 1.98 |
| S313 ($H_\gamma$) | A1 | G643 (CO) | A2 | 1.87 |
| H317 ($N_\delta$) | A1 | E540 ($H_\epsilon$) | A2 | 2.78 |
| Y476 ($H_\eta$) | A2 | E272 (CO) | A1 | 1.62 |
| T522 ($O_\gamma$) | A2 | R282 ($NH^b$) | A1 | 2.39 |
| S524 ($H_\gamma$) | A2 | H281 ($N_\delta$) | A1 | 2.12 |
| R531 ($H_\eta$) | A2 | R282 (CO) | A1 | 2.33 |
| N538 ($H_\delta$) | A2 | D27 ($O_\delta$) | A1 | 2.16 |
| E540 ($H_\epsilon$) | A2 | H317 ($N_\delta$) | A1 | 2.78 |
| S650 ($H_\gamma$) | A2 | P1980 (CO) | A3 | 1.54 |
| S654 ($H_\gamma$) | A2 | Y1786 ($O_\eta$) | A3 | 1.65 |
| Y664 ($H_\eta$) | A2 | H1822 (CO) | A3 | 1.94 |
| D666 ($O_\delta$) | A2 | L1789 (NH) | A3 | 1.93 |
| E683 ($O_\epsilon, H_\epsilon$) | A2 | Q1820 ($H_\epsilon, O_\epsilon$) | A3 | 2.58, 1.72 |
| N684 ($O_\epsilon$) | A2 | S1791 ($H_\gamma$) | A3 | 1.76 |
| S695 ($H_\gamma$) | A2 | L1843 (CO) | A3 | 2.03 |
| D696 ($H_\delta$) | A2 | S1949 ($O_\gamma$), N1950 (NH) | A3 | 1.99, 2.21 |
| Y1786 ($O_\eta$) | A3 | S654 ($H_\gamma$) | A2 | 1.65 |
| S1791 ($H_\gamma$) | A3 | N684 ($O_\epsilon$) | A2 | 1.76 |
| Y1792 ($H_\eta$) | A3 | S654 (CO) | A2 | 2.27 |
| D1795 ($O_\delta$) | A3 | L687 (NH) | A2 | 1.99 |
| Q1820 ($O_\epsilon, H_\epsilon$) | A3 | E683 ($H_\epsilon, O_\epsilon$) | A2 | 1.72, 2.58 |
| E1829 ($O_\epsilon, H_\epsilon$) | A3 | Y664 (NH, CO) | A2 | 2.15, 1.95 |
| S1949 ($O_\gamma$) | A3 | D696 ($H_\delta$) | A2 | 1.99 |
| N1950 ($H_\delta$) | A3 | T646 (CO) | A2 | 2.39 |
| R1966 ($H_{\eta 1}, H_{\eta 2}$) | A3 | K661 (CO) | A2 | 2.79, 2.01 |

[a]Backbone carbonyl oxygen atom.
[b]Backbone amide hydrogen atom.

Example 2

Thermostability of Factor VIII Variants

Figure 2A:
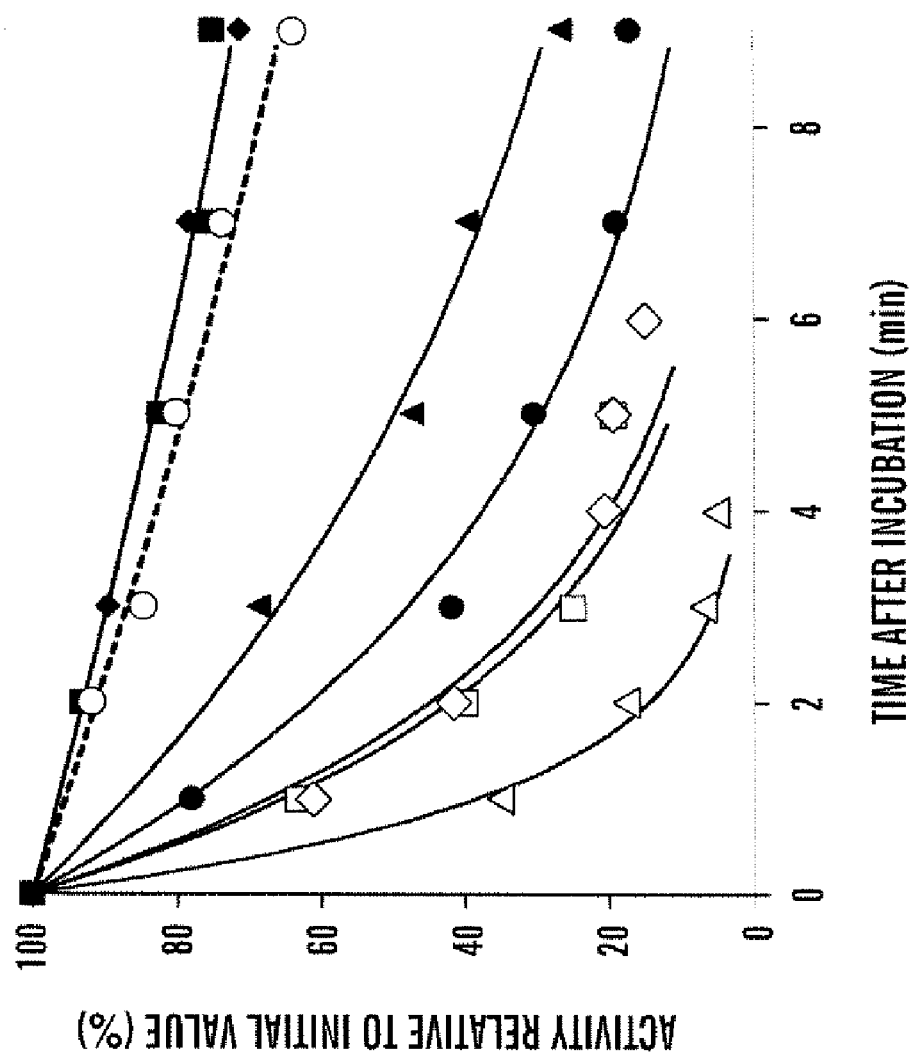
Figure 2B:
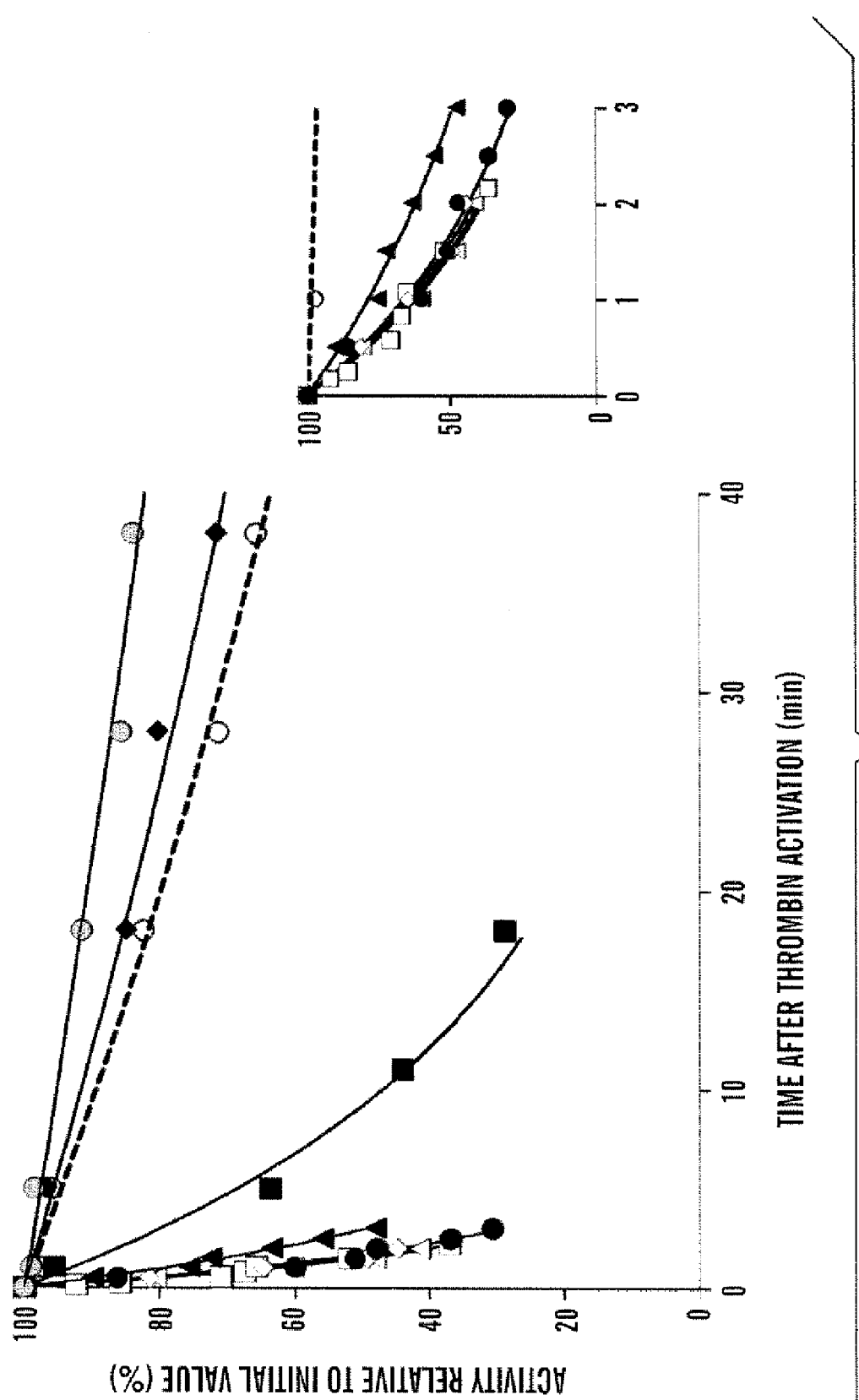

To assess the heat-stability of the WT procofactor and variants, a temperature at 55° C. was employed based upon factor VIII inactivation results described in an earlier study (Ansong et al., "Factor VIII A3 Domain Residues 1954-1961 Represent an A1 Domain-Interactive Site," *Biochemistry* 44:8850-8857 (2005), which is hereby incorporated by reference in its entirety). For these reactions, factor VIII was incubated for indicated times at the elevated temperature, after which the reaction mixture was immediately cooled to room temperature, and factor VIII reacted with thrombin and assayed for cofactor activity using a factor Xa generation assay. Rates of loss for factor VIII activity to the heat treatment, as judged by residual cofactor function, was determined as described in Methods. FIG. 2A shows results for variants showing the greatest and the least sensitivities to the heat treatment compared with WT.

Table 2 (below) summarizes the results obtained from factor VIII thermostability assays for the 30 variants. Overall, these activity data fit well to a single exponential decay function with correlation coefficients in most cases >0.98. While a number of mutations were benign with respect to the amino acid replacement (21 showing <2-fold differences in rates of decay), several residues including Arg282 (A1 domain), and A2 domain residues Ser524, Asn684 and Ser650 showed ~5- to ~20-fold increased rates in factor VIII decay suggesting an important role for these residues in maintaining factor VIII stability. Furthermore, the R282A and N684A variants showed significantly reduced specific activity values suggesting both activity and stability parameters were affected by the single point mutations. On the other hand, replacement of E287 and D302 with Ala yielded reduced rates for factor VIII decay at the elevated temperature. This apparent increase in protein stability following mutation is consistent with these acidic side chains destabilizing inter-domain interactions in the WT cofactor.

TABLE 2

Factor VIII and VIIIa Decay Rates and Activity Values

| | Decay rates (min$^{-1}$) | | | Specific Activity | |
|---|---|---|---|---|---|
| | | Factor VIIIa | | One-stage | Two-stage |
| | Factor VIII | FIXa (+)[a] | FIXa (−)[b] | assay | assay |
| WT | 0.0473 (1.00[c]) | 0.0113 (1.00) | 0.0631 (1.00) | 4.77[d] (1.00) | 44.5[e] (1.00) |
| R282A | 0.9646 (20.4) | 0.4708 (41.7) | 0.6738 (10.7) | 0.95 (0.20) | 1.77 (0.04) |
| S524A | 0.4332 (9.16) | 0.4554 (40.4) | 0.4416 (7.00) | 4.20 (0.88) | 1.02 (0.02) |
| N684A | 0.4002 (8.46) | 0.4096 (36.3) | 1.1837 (18.8) | 0.41 (0.09) | 2.15 (0.05) |
| R531A | 0.2448 (5.18) | 0.0758 (6.72) | | 2.62 (0.55) | 24.0 (0.54) |
| S650A | 0.1395 (2.95) | 0.0317 (2.81) | | 4.41 (0.93) | 45.5 (1.02) |

TABLE 2-continued

Factor VIII and VIIIa Decay Rates and Activity Values

| | Decay rates (min⁻¹) | | | Specific Activity | |
|---|---|---|---|---|---|
| | | Factor VIIIa | | One-stage | Two-stage |
| | Factor VIII | FIXa (+)[a] | FIXa (−)[b] | assay | assay |
| Y664F | 0.1173 (2.48) | 0.0148 (1.31) | | 5.25 (1.10) | 47.4 (1.07) |
| H281A | 0.1170 (2.47) | 0.0450 (3.99) | | 3.70 (0.78) | 21.1 (0.47) |
| Y1786F | 0.1138 (2.41) | 0.2361 (20.9) | 1.0740 (17.0) | 1.43 (0.30) | 6.21 (0.14) |
| D696A | 0.0889 (1.88) | 0.0118 (1.05) | | 4.82 (1.01) | 45.0 (1.01) |
| S313A | 0.0770 (1.63) | 0.0210 (1.86) | | 4.34 (0.91) | 36.5 (0.82) |
| E683A | 0.0743 (1.57) | 0.0263 (2.33) | | 1.00 (0.21) | 15.8 (0.36) |
| D1795A | 0.0697 (1.47) | 0.0238 (2.11) | | 3.82 (0.80) | 32.5 (0.73) |
| E540A | 0.0691 (1.46) | 0.0091 (0.81) | | 4.40 (0.92) | 37.9 (0.85) |
| R1966A | 0.0682 (1.44) | 0.0163 (1.44) | | 3.74 (0.78) | 36.6 (0.82) |
| D666A | 0.0646 (1.37) | 0.0545 (4.83) | | 2.47 (0.52) | 17.5 (0.39) |
| N538A | 0.0630 (1.33) | 0.0144 (1.28) | | 4.00 (0.84) | 35.7 (0.80) |
| H317A | 0.0629 (1.33) | 0.0145 (1.28) | | 3.83 (0.80) | 30.8 (0.69) |
| N1950A | 0.0618 (1.31) | 0.0195 (1.73) | | 3.46 (0.72) | 25.7 (0.58) |
| S654A | 0.0599 (1.27) | 0.0145 (1.28) | | 5.02 (1.05) | 45.2 (1.02) |
| T522A | 0.0596 (1.26) | 0.0270 (2.39) | | 0.83 (0.18) | 24.5 (0.55) |
| S1791A | 0.0595 (1.26) | 0.0208 (1.85) | | 3.73 (0.78) | 28.9 (0.65) |
| Y1792F | 0.0577 (1.22) | 0.4335 (38.4) | 0.7237 (11.5) | 1.41 (0.30) | 3.42 (0.08) |
| Y476F | 0.0579 (1.22) | 0.0139 (1.23) | | 4.57 (0.96) | 41.8 (0.94) |
| S1949A | 0.0573 (1.21) | 0.0129 (1.14) | | 3.17 (0.66) | 28.6 (0.64) |
| S695A | 0.0524 (1.11) | 0.0085 (0.75) | | 5.15 (1.08) | 45.4 (1.02) |
| D27A | 0.0489 (1.03) | 0.0089 (0.79) | | 4.53 (0.95) | 40.1 (0.90) |
| Q1820A | 0.0480 (1.01) | 0.0114 (1.01) | | 4.91 (1.03) | 44.0 (0.99) |
| E287A | 0.0367 (0.78) | 0.0088 (0.78) | | 2.86 (0.60) | 16.4 (0.37) |
| D302A | 0.0369 (0.78) | 0.0049 (0.43) | | 5.38 (1.03) | 49.0 (1.10) |

Mutant factor VIII forms are ordered based on decreasing rates of factor VIII decay. Standard deviations for rate decay values are estimated based on least squares curve-fitting and are within ~10% of mean values.
[a]Decay experiments performed in the presence of factor IXa.
[b]Decay experiments performed in the absence of factor IXa.
[c]values in parentheses are relative to wild type.
[d]Unit/µg.
[e]nM factor Xa generated/min/nM factor VIII.

Example 3

Factor VIIIa Decay Rates

Factor VIIIa activity is labile due to A2 subunit dissociation (Fay et al., "Human Factor VIIIa Subunit Structure: Reconstruction of Factor VIIIa from the Isolated A1/A3-C1-C2 Dimer and A2 Subunit," *J Biol Chem.* 266:8957-8962 (1991); Lollar et al., "pH-dependent Denaturation of Thrombin-activated Porcine Factor VIII," *J Biol Chem.* 265:1688-1692 (1990), each of which is hereby incorporated by reference in its entirety). Results from earlier studies showed that inclusion of factor IXa and phospholipid vesicles with factor VIIIa to form the Xase complex reduced the lability of the cofactor (Lollar et al., "Stabilization of Thrombin-activated Porcine Factor VIII:C by Factor IXa Phospholipid," *Blood* 63:1303-1308 (1984); Lamphear et al., "Factor IXa Enhances Reconstitution of Factor VIIIa from Isolated A2 Subunit and A1/A3-C1-C2 Dimer," *J. Biol. Chem.* 267:3725-3730 (1992), each of which is hereby incorporated by reference in its entirety) by partially stabilizing the A2 subunit within factor Xase (Fay et al., "Model for the Factor VIIIa-dependent Decay of the Intrinsic Factor Xase: Role of Subunit Dissociation and Factor IXa-catalyzed Proteolysis," *J Biol Chem.* 271:6027-6032 (1996), which is hereby incorporated by reference in its entirety). This approach was recently used to examine the decay rate for an E1829A factor VIIIa mutant (Wakabayashi et al., "A3 Domain Residue Glu 1829 Contributes to A2 Subunit Retention in Factor VIIIa," *J. Thromb. Haemost.* 5:996-1001 (2007), which is hereby incorporated by reference in its entirety) since the activity decay of this variant factor VIIIa, in the absence of factor IXa and membrane, was too rapid to measure accurately. This approach was similarly employed to assess rates for factor VIIIa decay for the panel of variants described in this Example. Factor VIII (4 nM) was incubated with a molar excess of factor IXa (40 µM) and phospholipid vesicles, rapidly activated with thrombin and subsequent factor Xase activity was measured over a time course at 23° C. Rates of decay of factor Xase activity was attributed to A2 subunit dissociation and data were fitted using a single exponential decay. Given the high $K_d$ value for the affinity of A2 subunit within factor VIIIa (144 nM) and the low factor VIIIa concentration (4 nM) used in the reactions, the effect of re-association of dissociated A2 subunit is negligible, supporting use of a simple single exponential applied for this regression analysis.

Results are presented in FIG. 29, which shows data for the most severely affected variants as well as those variants showing a positive response to the mutation. Seven variants possessing significant (>5-fold) increases in rates of factor VIIIa decay compared with WT (Table 2). These mutations included R282A, S524A, N684A, E1829A, Y1786F, D666A, and Y1792F. Factor VIII activity values for these variants as measured by a two-stage assay were significantly lower than those determined by one-stage assay (FIG. 1), consistent with the mutations leading to appreciable rates of A2 subunit dissociation. Furthermore, several of these mutations (including R282A, N684A and Y1792F) showed overall low specific activity in the one-stage assay. As is the case for factor VIII mutants possessing this assay discrepancy, activity determined from the one-stage assay was also reduced (Pipe et al., "Mild Hemophilia A Caused by Increased Rate of Factor VIII A2 Subunit Dissociation: Evidence for Nonproteolytic Inactivation of Factor VIIIa in vivo," *Blood* 93:176-183 (1999);

Pipe et al., "Hemophilia A Mutations Associated with 1-stage/2-stage Activity Discrepancy Disrupt Protein-protein Interactions within the Triplicated A Domains of Thrombin-activated Factor VIIIa," *Blood* 97:685-691 (2001); Hakeos et al., "Hemophilia A Mutations within the Factor VIII A2-A3 Subunit Interface Destabilize Factor VIIIa and Cause One-stage/Two-stage Activity Discrepancy," *Thromb Haemost.* 88:781-787 (2002), each of which is hereby incorporated by reference in its entirety), possibly reflecting direct effects of A2 dissociation rates on determining factor VIII activity.

Conversely, the variants E287A and D302A that possessed greater thermostabilities than WT factor VIII also yielded enhanced stability of factor VIIIa as judged by reductions in the rates of cofactor decay following activation by thrombin. Results with the D302A variant were more pronounced and showed an ~2-fold reduced rate of cofactor decay relative to WT factor VIIIa, retaining 90% of its original activity after 40 min. This observation was consistent with the mutations primarily altering conformation at the inter-domain interface in the procofactor.

Taken together, these results in Examples 1-3 identify contributions of multiple residues to inter-A2 (domain) subunit interactions in the procofactor and cofactor forms of factor VIII, with selected residues making disparate contributions to protein stability. While the observed effects of mutation at the target residues were for the most part either benign or detrimental, the mutations at two A1 domain acidic residues, D302 and E287, yielded modest enhancement in stability in both pro- and active cofactor forms. The relative activity of E287 was somewhat reduced compared with WT, whereas the activity values for the D302 variant were indistinguishable from the WT protein, and suggest the latter represents a gain-of-function mutation. These results indicate that some destabilization may result from burying the (negative) charge at the interface and/or an increase in stability when these residue side chains are hydrophobic.

Example 4

Identification of Additional Target Residues and Generation of Point Mutants at Glu272, Asp519, Glu665, and Glu1984

Based on the results of the preceding Examples, the substitution of other charged residues was explored. Using the ceruloplasmin-based homology model (Pemberton et al., "A Molecular Model for the Triplicated A Domains of Human Factor VIII Based on the Crystal Structure of Human Ceruloplasmin," *Blood* 89:2413-2421 (1997), which is hereby incorporated by reference in its entirety) for the A domains of factor VIII, four charged residues were identified (Glu272, Asp519, Glu665, and Glu1984). These four residues appear to be buried at the interface of the A2 domain with either the A1 domain (Glu272 and Asp519) or the A3 domain (Glu665, and Glu1984), but did not appear to contribute to H-bonding interactions based upon spatial separations of >2.8 Å with potential bonding neighbors. These residues were mutated to either Ala or Val to eliminate charge as well as provide for potential hydrophobic interactions with similar side chains from other buried residues Factor VIII variants were prepared as B-domainless factor VIII in stable-expressing BHK cell lines.

Figure 3A:
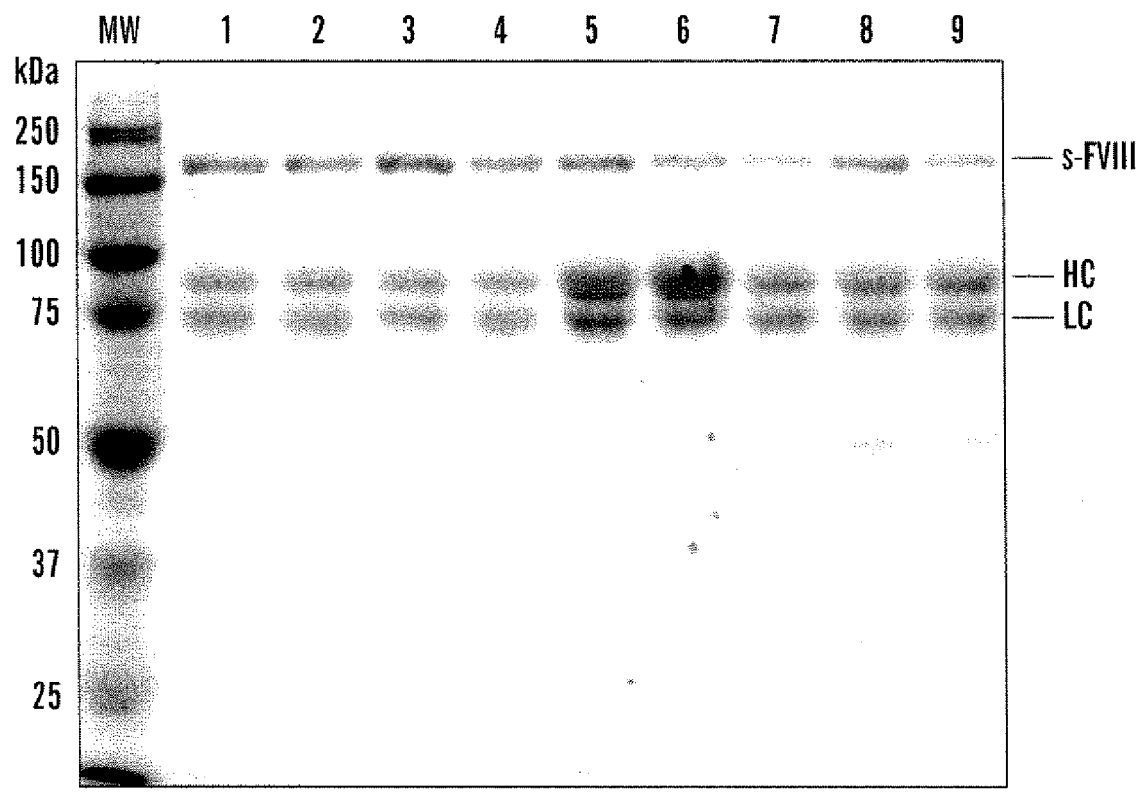
Figure 3B:
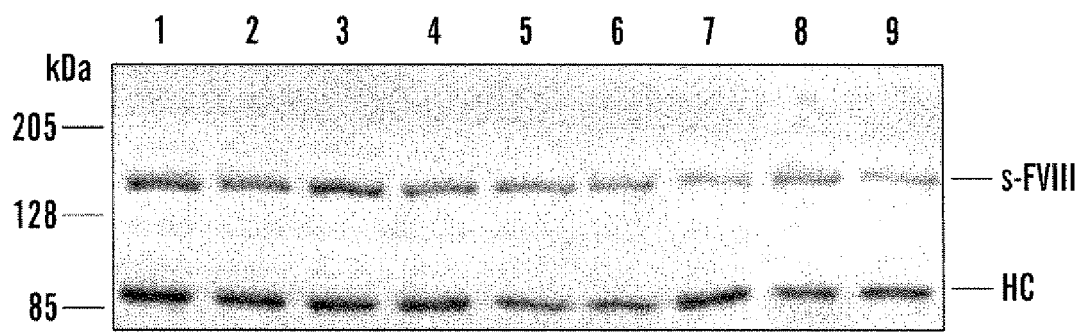

Factor VIII was expressed as a mixture of single chain and heterodimer forms. The purified proteins ranged from ~85% to >95% as judged by SDS-PAGE (FIG. 3A). Western blotting using an anti-A2 domain antibody was used to quantitate the stoichiometry of the single chain and heterodimer forms (FIG. 3B). This value was near unity for WT and was somewhat lower and variable for the factor VIII variants.

Figure 4B:
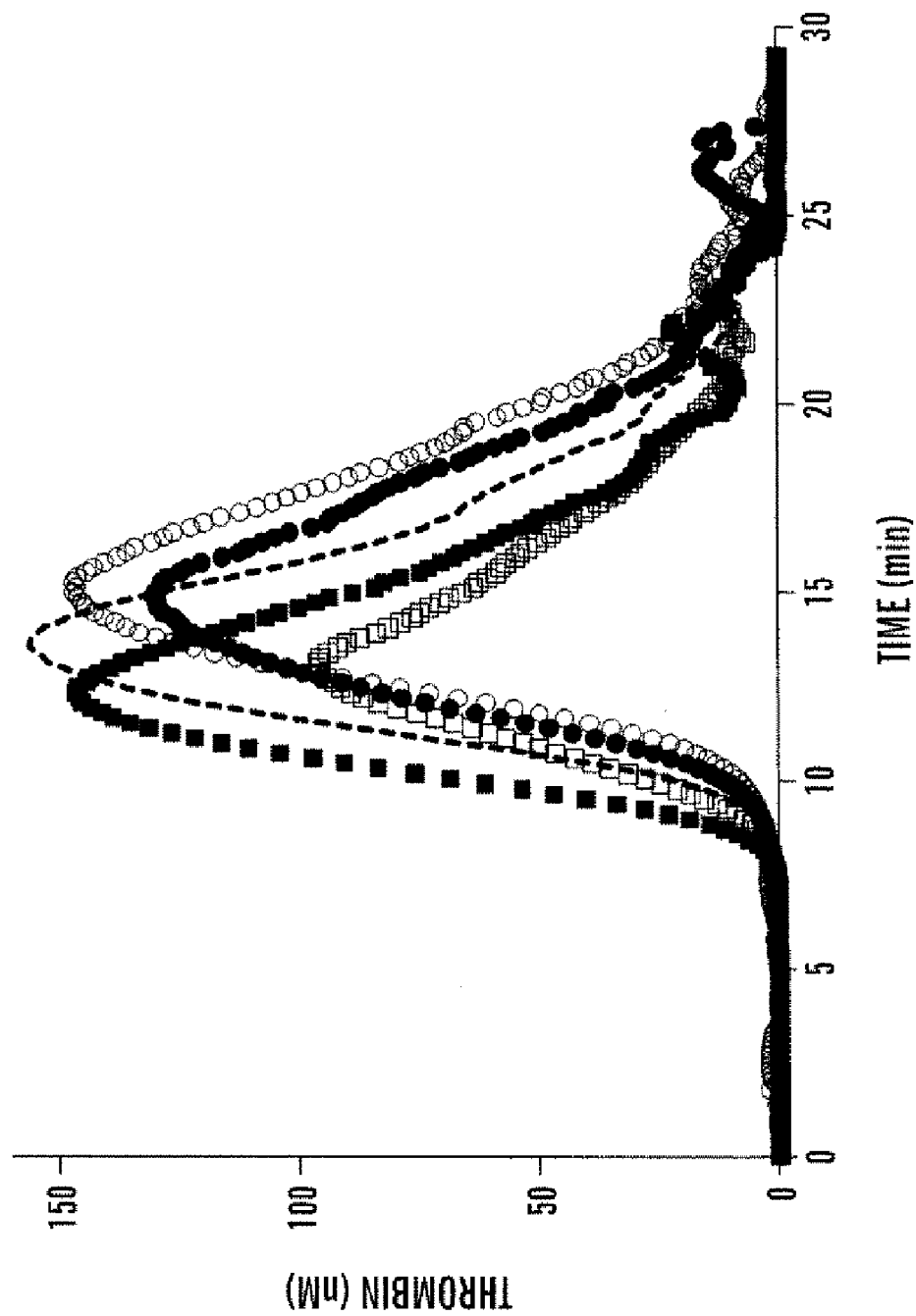
Figure 4C:
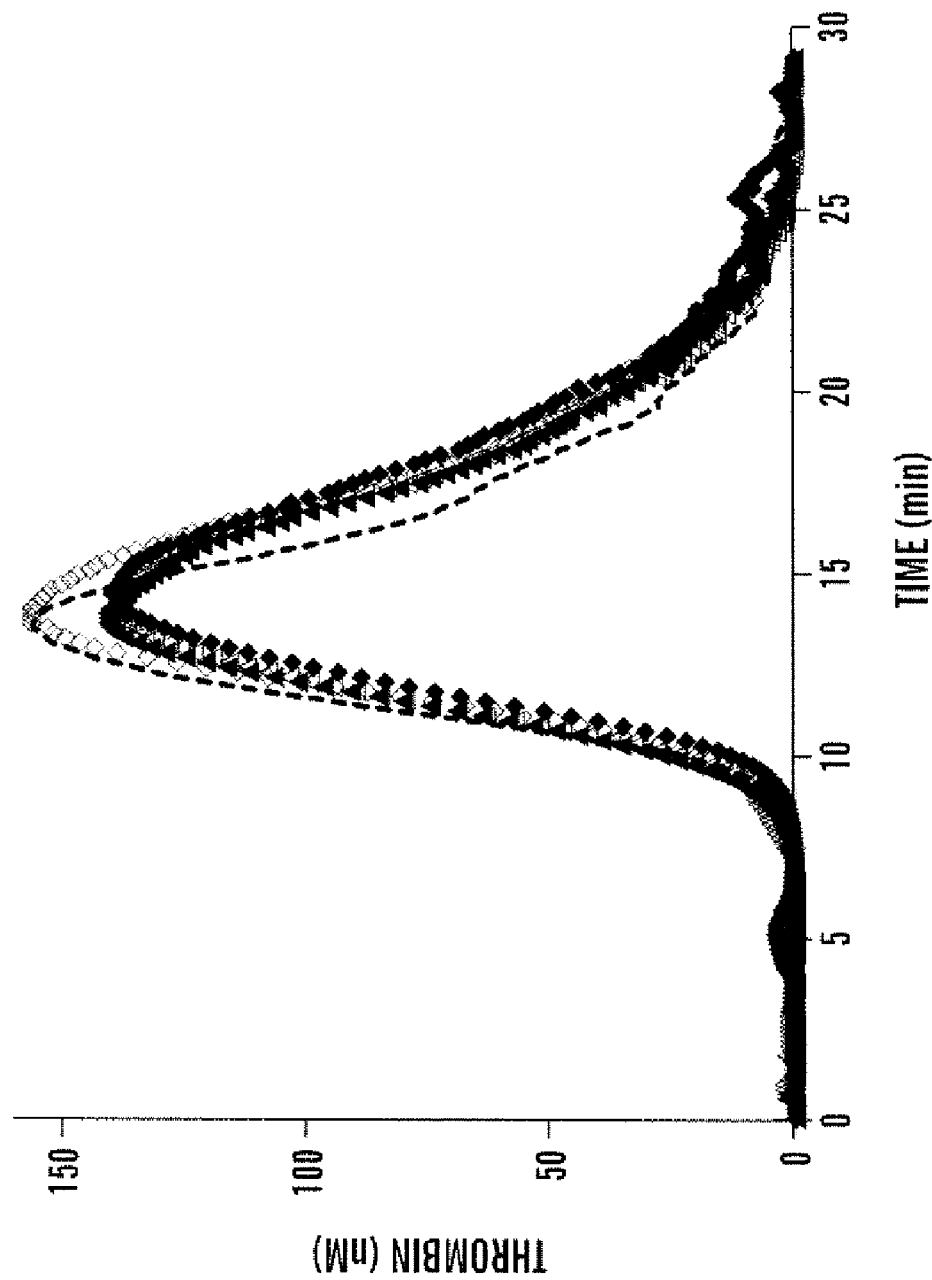
Figure 4D:
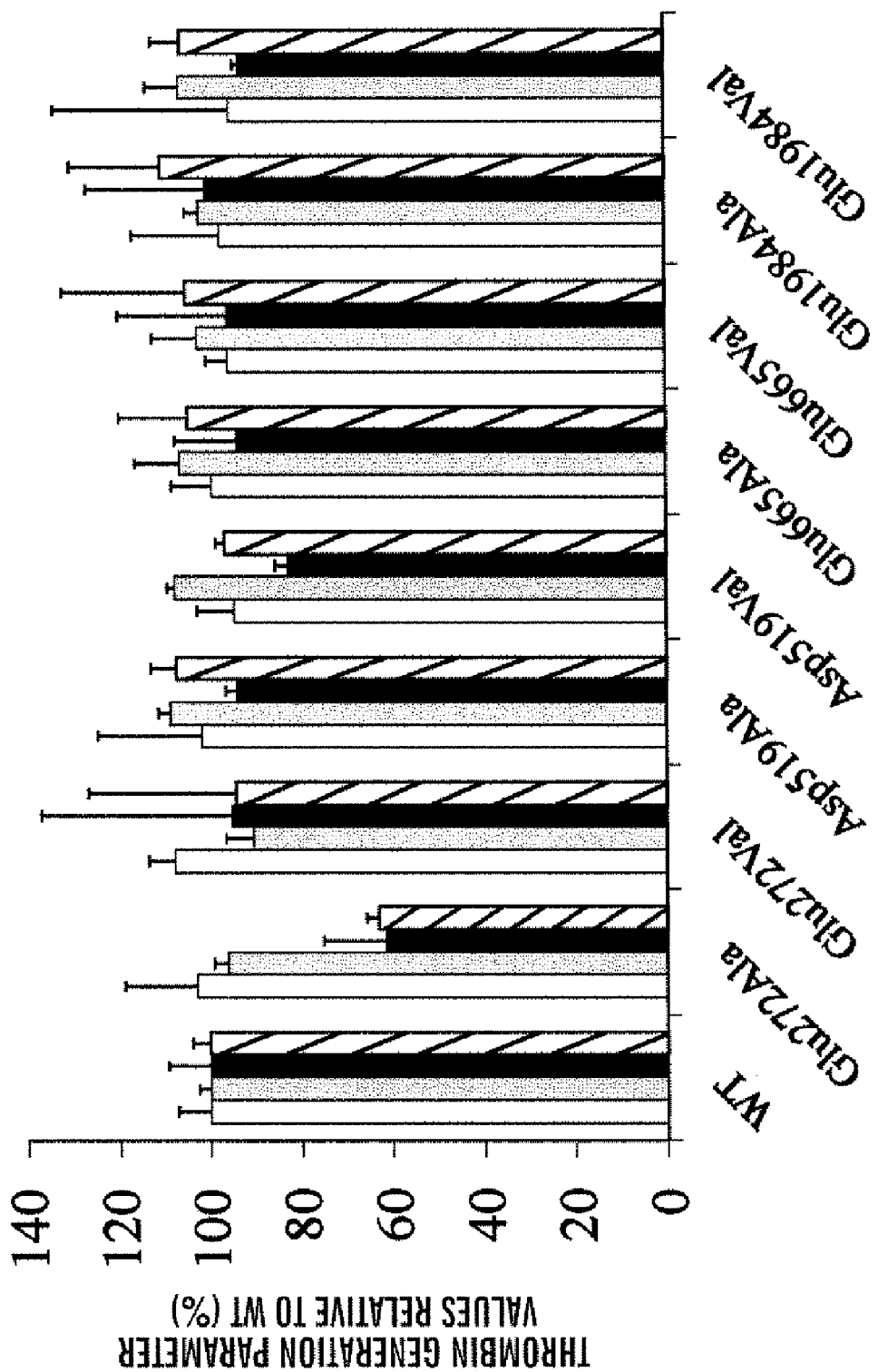

Purified proteins were assessed for specific activity using both one-stage and two-stage assays (FIG. 4A) and thrombin generation parameters (FIGS. 4B-D). All but the Glu272Ala variant yielded specific activity values that were at least 80% that of WT, suggesting the remaining mutations had little if any effect on factor VIII cofactor function. Thrombin generation performed at low rTF concentration (0.5 pM) and a physiologic concentration (1 nM) factor VIII yielded results that paralleled the specific activity values. Parameter values shown in FIG. 4D indicated the peak value and ETP for the Glu272Ala were reduced compared to WT, whereas all other parameter values for the remaining variants ranged from >80-110% the WT value.

Example 5

Thermostability of Glu272, Asp519, Glu665 and Glu1984 Factor VIII Variants

The purified factor VIII mutant proteins were assessed for stability at elevated temperatures as judged by rates of activity loss. Factor VIII (4 nM) was incubated at 52-60° C. and at the indicated times an aliquot was removed, cooled to room temperature, reacted with thrombin, and residual cofactor activity was measured using a factor Xa generation assay as described in the Materials and Methods. Results shown in FIG. 5A illustrate the time course for activity decay of the factor VIII WT and variants at 55° C. This temperature was chosen based upon an earlier study (Ansong et al., "Factor VIII A1 Domain Residues 97-105 Represent a Light Chain-interactive Site," *Biochemistry* 45:13140-13149 (2006), which is hereby incorporated by reference in its entirety) showing near-complete activity loss within 1 h for WT factor VIII. The WT protein lost 50% activity in ~15 min. It was observed that the Glu272Ala and Glu272Val variants displayed reduced stability as judged by somewhat faster activity decay, and this property may be related to the reduced specific activities observed for mutations at this site. On the other hand, Ala and Val replacements for Asp519, Glu665, and Glu 1984 all showed improved stability at the elevated temperature with variants possessing mutations at the two former sites retaining 50% activity through ~20-25 min while mutations at the latter site yielded variants that maintained this activity level through >30 min. Comparison of the decay rate values from the fitted curves (Table 1, below) indicated that factor VIII thermal stability was improved ~2-fold for the Glu1984 variants relative to WT with mutation to Val appearing somewhat preferred to Ala.

Results assessing a range of temperatures (FIG. 5B) indicated that both Ala and Val variants of Asp519, Glu665, and Glu1984 consistently showed reductions of decay rate up to 2-fold compared to WT at all temperatures tested. However, the presence of both single chain and heterodimer forms in somewhat varying ratios may impact these decay rate results should one form show greater stability. A control experiment using Kogenate factor VIII which is essentially all in the heterodimer form (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001), which is hereby incorporated by reference in its entirety) yielded decay rates that were 2-fold that of WT (FIG. 5B), consistent with the heterodimer form showing less stability to elevated temperature than single chain factor VIII. Thus, the decay rates measured are apparently due to heterogeneity of single chain and two chain content in the various factor VIII forms. However, given that all the variants possessed less relative single chain factor VIII compared with the WT (see FIG. 5B), these data indicated that decay rate values for these variants underestimate the increase in stability between the mutants and WT.

TABLE 3

Factor VIII and VIIIa Decay Rates

| | Factor VIII Decay | | Factor VIIIa Decay | |
|---|---|---|---|---|
| | Thermostability at 55° C. (min$^{-1}$) | Plasma stability (hr$^{-1}$) | Factor IXa absent (min$^{-1}$) | Factor IXa present (min$^{-1}$) |
| WT | 0.0471* (1.00) | 0.0178 (1.00) | 0.0836 (1.00) | 0.0154 (1.00) |
| E272A | 0.0542 (1.15) | n.d.† | 0.1638 (1.95) | 0.0163 (1.06) |
| E272V | 0.0602 (1.28) | n.d. | 0.2271 (2.72) | 0.0159 (1.03) |
| D519A | 0.0336 (0.71)‡ | 0.0066 (0.37)‡ | 0.0556 (0.66)‡ | 0.0063 (0.41)‡ |
| D519V | 0.0262 (0.56)‡ | 0.0184 (1.03) | 0.0642 (0.77)‡ | 0.0068 (0.44)‡ |
| E665A | 0.0359 (0.76)‡ | 0.0149 (0.84)§ | 0.0520 (0.62)‡ | 0.0078 (0.51)‡ |
| E665V | 0.0309 (0.66)‡ | 0.0047 (0.26)‡ | 0.0160 (0.19)‡ | 0.0052 (0.34)‡ |
| E1984A | 0.0240 (0.51)‡ | 0.0080 (0.45)‡ | 0.0241 (0.29)‡ | 0.0027 (0.18)‡ |
| E1984V | 0.0211 (0.45)‡ | 0.0078 (0.44)‡ | 0.0217 (0.26)‡ | 0.0019 (0.13)‡ |

Standard deviations for rate decay values are estimated based upon least squares curve fitting and are within ~10% of mean values for thermostability and factor VIIIa decay measurements and within ~15% of mean values for the plasma stability measurements. Values in parentheses are relative to the WT value. Single letter code is used to designate the amino acid residues, E (Glu), D (Asp), A (Ala), and V (Val).
†not determined.
‡p < 0.001 compared to the rate of WT (Student's t-test).
§p < 0.05 compared to the rate of WT (Student's t-test).

Example 6

Factor VIII Stability in Plasma at 37° C.

To test the effects of the mutations on factor VIII stability under more native conditions, a near physiological concentration of the proteins (1 nM) was incubated in (anti-coagulated) factor VIII deficient plasma from a hemophilia A patient free from factor VIII inhibitor activity at 37° C. for up to 4 days. Residual factor VIII was assayed daily using a one-stage clotting assay. Activity of the WT factor VIII was reduced to ~50% after 2 days as was that of the Asp519Val variant, while the Glu665Ala variant showed a modest (~15%) reduction in the rate of activity decay (FIG. 6 and Table 3). However, the activity values for the Asp519Ala, Glu665Val and both Glu1984 variants were ≧50% the initial value at day 4. The results obtained from the plasma incubation in large part parallel those from the incubations performed at elevated temperature with the Glu665Val variant and the two Glu1984 variants demonstrating significant increases in stability under the two reaction conditions as judged by retention of function. While both Asp519 variants showed improved stability at elevated temperature, only the Ala variant showed improvement in the plasma assay.

Example 7

Factor VIIIa Decay Rates of Glu272, Asp519, Glu665 and Glu1984 Variants

The above results indicate that mutations consistent with replacing buried charged residues with hydrophobic residues in general yielded factor VIII protein showing enhanced stability. Inasmuch as these mutations are at or near the interface of the A2 domain with A1 or A3, it was predicted that they could positively impact the lability of factor VIIIa by reducing rates for dissociation of the A2 subunit. Rates of loss of factor VIIa activity resulting from this mechanism were assessed under two conditions. In the first, the WT and factor VII variants were activated with thrombin and at indicated times the remaining cofactor activity was determined following addition of factor IXa and factor X and monitoring rates of factor Xa generation. In the second method, the above assay was modified to include addition of factor IXa prior to factor VIII activation to allow for immediate formation of factor Xase. Incorporation of factor VIIIa in the factor Xase complex has been shown to partially stabilize cofactor activity by reducing its decay rate as much as 10-fold by a mechanism consistent with factor IXa tethering the AS and A3C1C2 subunits with Xase (Fay et al., "Model for the Factor VIIIa-dependent Decay of the Intrinsic Factor Xase: Role of Subunit Dissociation and Factor IXa-catalyzed Proteolysis," *J Biol Chem.* 271:6027-6032 (1996), which is hereby incorporated by reference in its entirety).

Results obtained in the absence or presence of added factor IXa are shown in FIGS. 7A and 7B, respectively. In the absence of factor IXa, WT factor VIIIa lost 50% of its activity in ~8 min (FIG. 7A), whereas this level of activity persisted for ~40 min when factor IXa was included during factor VIII activation (FIG. 7B). Decay rate values are shown in Table 3 and indicate a >5-fold stabilization of cofactor activity by formation of factor Xase. Evaluation of the variants revealed that both Glu272Ala and -Val forms possessed 2- and 3-fold increased rates of decay, respectively, in the absence of factor IXa as compared to the WT control. These results indicate a weakened inter-subunit affinity with either mutation, possibly the result of loss of a relatively weak affinity bonding interaction involving the acidic side chain. In the presence of factor IXa, decay rates for the two variants were essentially indistinguishable from that of WT, indicating that inclusion of factor IXa eliminated any detrimental interaction generated by the mutations at this residue.

Mutations at the other three sites (Asp519, Glu665 and Glu1984) all resulted in reductions in factor VIIIa decay rates with the degree of reduction variable depending upon the specific residue changed and in one case, the replacement residue. Mutations at Asp519 yielded ~30% reductions in decay rates that were similar for both the Ala and Val variants when factor IXa was absent. Rates for activity decay of these variants were decreased >2-fold in the presence of factor IXa, suggesting a synergy of the mutations with the stabilizing effects of binding the enzyme. While the Glu665Ala variant showed similar values to the two Asp519 variants, the Glu665Val variant showed 5-fold and 3-fold reductions in decay rates in the absence and presence of factor IXa, respectively, suggesting replacement with the larger hydrophobic residue yielded a more favorable interaction with neighboring residues for A2 subunit retention. Finally, both Glu1984 variants showed ~4-fold reductions in factor VIIIa decay compared with WT in the absence of factor IXa, and 5-8-fold reductions when factor IXa was present. The significance of this enhanced stability is observed in FIG. 7B which shows >90% factor VIIIa activity remaining after 40 min in factor Xase comprised of either Glu1984 variant. The similarity in responses with either Ala or Val at Glu1984 suggested that both residues were well tolerated with perhaps a slightly stronger inter-subunit affinity achieved in the presence of Val. Overall, these results demonstrate significant enhancement in factor VIIIa stability resulting from improved M2 subunit retention following selective replacement of charged residues with hydrophobic residues.

Discussion of Examples 1-7

The above Examples demonstrate that substitution of selected charged residues with hydrophobic ones at sites predicted to interface the A2 domain resulted in a general, though variable, increase in the stability of factor VIII. This stability was assessed following activity retention at elevated temperature as well as by reduction in the rate of A2 subunit dissociation in the cofactor.

In the initial analysis of Examples 1-3, 30 residues localized to the factor VIII A2 domain interface were selected for mutational analysis based upon spatial separations of <2.8 Å, which could potentially form hydrogen-bonding partners. The 30 charged/polar residues were mutated to Ala (or Phe for Tyr residues), recombinant proteins stably expressed, and rates of loss of activity were measured. Fourteen of the 30 residues examined showed >2-fold increases in rates of factor VIII decay at 55° C. and/or rates for factor VIIIa decay relative to WT, suggesting that multiple residues at the A1 A2 and A2A3 domain interfaces contribute to the stabilization of factor VIII. Interestingly, two acidic residues that were examined, Asp302 and Glu287, yielded modest (<2-fold) enhancement in stability in both the procofactor and active cofactor forms when mutated to Ala. Both of these acidic residues are conserved in human, canine, porcine, mouse, rabbit, rat, and bat factor VIII. These initial results suggested that these acidic side chains did not contribute to stabilizing hydrogen-bonding interactions but rather were somewhat detrimental to factor VIII structure as assessed by functional stability.

Based on these initial studies, the creation of additional hydrophobic interactions were assessed for gain of function. The four acidic residues examined in Examples 4-7 are conserved in human, canine, porcine, mouse, rabbit, and bat factor VIII, while Glu665 is Ala and Glu1984 is Thr in rat factor (see Swiss Institute of Bioinformatics, online analysis UniProtKB/Swiss-Prot Release 55.5 and UniProtKB/TrEMBL Release 38.5 (2008), which is hereby incorporated by reference in its entirety). The results of Examples 4-7 demonstrate that three of these residues, Asp519, Glu665 and Glu 1984, when replaced with Ala and/or Val, resulted in enhancements in protein stability. Only one acidic residue evaluated in Examples 4-7 yielded results that were detrimental to activity when mutated. Mutation at Glu272 to Ala yielded a low specific activity factor VIII form with reduced thrombin generation parameters values; and both Ala and Val replacements possessed moderately decreased thermostability and 2-3-fold higher rates of A2 subunit dissociation in the cofactor form as compared with WT. From these observations, it is believed that Glu272 may indeed participate in bonding interaction(s) with neighboring residues, and subsequent mutations at this site disrupt these interactions. This conclusion is consistent with examination of the Hemophilia A database (Kemball-Cook et al., "The Factor VIII Structure and Mutation Resource Site: HAMSTeRS version 4," *Nucleic Acids Res.* 26:216-219 (1998); Kemball-Cook (MRC Clinical Sciences Centre), Haemophilia A Mutation Database (accessed Jul. 2, 2008), each of which is hereby incorporated by reference in its entirety), which lists Lys (charge reversal) or Gly (small side chain) at position 272 as a moderate/mild phenotype with reduced factor VIII antigen. The latter observation is consistent with the mutations yielding increased plasma instability. However, there was no significant effect of these mutations on levels of expression in cell culture following mutations at this site to Ala or Val. Conversely, no mutations at Asp519, Glu665 and Glu1984 are listed in the database.

Proteins tend to fold so that the charged or polar moieties remain solvent exposed while hydrophobic groups are buried (Pace et al., "Forces Contributing to the Conformational Stability of Proteins," *FASEB J.* 10:75-83 (1996), which is hereby incorporated by reference in its entirety). Therefore, based upon the observed gain-of-function mutations at Glu287, Asp302, Asp519, Glu665 and Glu1984 when these residues are replaced with hydrophobic ones, it is believed that these charged residues are buried at the A2 domain interfaces. Furthermore, these results suggest that these acidic residues do not contribute to electrostatic bonding interactions and are likely destabilizing to WT protein structure and/or subunit interactions.

Because mutagenesis using either Ala or Val resulted in a hydrophobic residue (to replace the charged acidic residues), the Ala or Val substitution would tend to stabilize other hydrophobic contacts at the interface. Furthermore, the Val side chain is larger than Ala, so comparison of effects on activity following replacement at a given site may offer some insights into residue packing and volume at that site. For example, that replacement of Glu1984 with either residue yielded similar results, suggesting both were well-tolerated at that site; whereas Glu665Val showed a 3-fold reduced factor VIIIa decay rate compared with Glu665Ala, suggesting the larger volume side chain of Val was better tolerated in the putative hydrophobic binding pocket.

Overall, the results of Example 1-7 contribute significantly to the understanding of factor VIII A domain structure, which has previously been limited to models derived from homology with a high resolution structure for ceruloplasmin (Pemberton et al., "A Molecular Model for the Triplicated A Domains of Human Factor VIII Based on the Crystal Structure of Human Ceruloplasmin," *Blood* 89:2413-2421 (1997), which is hereby incorporated by reference in its entirety) and a recent, intermediate resolution structure (3.75 Å) of human factor VIII (Shen et al., "The Tertiary Structure and Domain Organization of Coagulation Factor VIII," *Blood* 111:1240-1247 (2008), which is hereby incorporated by reference in its entirety). While the latter structure does not allow for assignments of hydrogen bonding interactions (<2.8 Å), the authors of that study indicate that the A domains of factor VIII can be superimposed onto those of ceruloplasmin with a high degree of accuracy.

While the ceruloplasmin model suggests Asp302 and Glu287 could contribute hydrogen bonding interactions, the stability studies of Example 1-3 demonstrate that this in unlikely. Instead, these acidic side chains are believed to be buried in a hydrophobic environment. Conversely, results from Examples 4-7 support the belief that Glu272 likely contributes a hydrogen bonding interaction at the A2 domain interface, because loss of this charge reduces factor VIII (VIIIa) stability. The remaining three acidic residues evaluated in Examples 4-7 appear to be buried at the interface as predicted by the model, in that no polar atom from a neighboring residue on a complementary domain appears to localize near the carboxylic groups of these residues. Rather, it is noted that these moieties appear to be proximal with hydrophobic groups. For example, the model predicts that the carboxyl oxygen of Asp519 and methyl carbon of Thr275 are separated by ~4.2 Å, the carboxyl oxygen of Glu665 and methyl carbon of Val1982 are separated by ~8.1 Å, and the carboxyl oxygen of Glu1984 and methyl carbon of Val663 are separated by ~6.2 Å.

Factor VIII variants demonstrating enhanced stability and reduced rates of cofactor activity decay represent positive attributes for a therapeutic preparation. The former property should allow for increased yields of active protein during its purification and formulation, resulting in overall higher specific activity values. These reagents may also possess a longer circulating half-life relative to WT (see FIG. 6), exclusive of various cellular clearance mechanisms. Two groups have previously reported on factor VIII variants where cofactor activity has been stabilized by reducing/eliminating the rate of A2 subunit dissociation. In both cases, mutations were employed to covalently link the A2 domain to other regions of the molecule. In one case, an inactivation-resistant factor VIII was prepared by linking the A2 domain to a segment of B-domain contiguous with the A3C1C2 domains and lacking thrombin cleavage sites that would release either the A2 domain or B-domain fragment following procofactor activation (Pipe et al., "Characterization of a Genetically Engineered Inactivation-resistant Coagulation Factor VIIIa," *Proc Natl Acad Sci USA* 94:11851-11856 (1997), which is hereby incorporated by reference in its entirety). In a second case, selected residues in the A3 and A2 domains that were in close proximity were replaced with Cys residues so as to form disulfide bridges between the two domains such that A2 would remain covalent with A3 following thrombin activation (Gale et al., "An Engineered Interdomain Disulfide Bond Stabilizes Human Blood Coagulation Factor VIIIa," *J Thromb Haemost.* 1: 1966-1971 (2003); Radtke et al., "Disulfide Bond-stabilized Factor VIII has Prolonged Factor VIIIa Activity and Improved Potency in Whole Blood Clotting Assays," *J Thromb Haemost.* 5:102-108 (2007), each of which is hereby incorporated by reference in its entirety). The latter mutants also demonstrated augmented activity in thrombin generation assays, although the reaction conditions employed in these studies used a sub-physiologic (<0.5 nM) concentration of factor VIII.

The results of Examples 1-7 using a physiologic factor VIII level (1 nM) showed little difference between WT and the variants demonstrating higher stability, although the Glu272Ala yielded reduced thrombin generation parameters consistent with its lower specific activity. The failure to observe a significant difference with the high stability variants may reflect differences in reaction conditions and/or that these mutations do not covalently bridge the A2 domain and the rates for factor VIIa decay are not sufficiently reduced.

Results presented in Examples 1-7 demonstrate several-fold decreases in rates for cofactor inactivation can be achieved following single point mutations to convert acidic residues to hydrophobic ones. In each of these case, these mutations occur at interfaces where the altered residues are likely buried and not surface exposed, and do not alter covalent interactions within the protein. Based on preliminary results, the cofactor forms of the Glu1984Val and -Ala variants and the WT cofactor show similar rates of inactivation as measured by activated protein C-catalyzed cleavages at Arg336 and Arg562 (Varfaj et al., "Residues Surrounding Arg336 and Arg562 Contribute to the Disparate Rates of Proteolysis of Factor VIIIa Catalyzed by Activated Protein C," *J. Biol. Chem.* 282(28):20264-72 (2007), which is hereby incorporated by reference in its entirety). This supports the belief that down-regulation of these higher stability variants should also proceed via the protein C pathway in much the same way as WT cofactor. Thus, the stabilized variants of the present invention should be free from the problems associated with the inactivation-resistant mutants described above.

Example 8

Stability Analysis of Di- and Tri-substituted Factor VIII Variants

To determine whether additive or synergistic effects will result in further enhancements in factor VIII (VIIa) stability, combinations of the point mutations described in the preceding Examples have been prepared using the same procedures described in the Materials and Methods. In particular, double or triple combination mutants were prepared with the Ala or Val substitutions of residues Asp519, Glu665, and Glu1984. These combination mutants (amino acids are identified using the single letter code) include: D519AE665A, D519AE665V, D519AF1984A, D519AF1984V, D519VE665V, D519VE1984A, D519VE1984V, E665AE1984A, E665AE1984V, E665VE1984A, E665VE1984V, D519AE665VE1984A, D519VE665VE1984A, D519VE665VE1984V. D519VE665A factor VIII was excluded from this analysis, because this mutant showed atypical characteristics in ELISA and Western blot results.

To produce triple mutants, D519A or D519V was combined with either E665VE1984A or E665VE1984V. The other combinations were eliminated because the E665AE1984A and E665AE1984V double mutants did not enhance both factor VIII and factor VIIIa stability as compared with each single mutant. Results using D519AE665VE1984V were excluded for the same reasons as observed for D519VE665A.

The first group of new mutants (Group A), which combined mutation (Ala or Val) at Asp519 with mutation at either Glu665 or Glu 1984, retained normal values for specific activity (>80% the wild type (WI) value, FIG. 8). Interestingly D519AE665A, D519VE665V, D519VE1984A, and D519VE1984V showed significantly increased specific activity values up to ~1.8 fold compared to WT factor VIII as measured by a one stage clotting assay (FIG. 8). The specific activity of the second group of mutants (Group B), which were the combination of mutations at Glu665 and Glu1984 unexpectedly showed reduction in specific activity of up to ~2 fold compared to WT factor VIII, with the exception of E665VE1984A which was somewhat greater than the WT value (FIG. 8). The third group (Group C) represents the triple mutations and showed normal to modestly increased activity by the one-stage assay (D519VE665VE1984V). However, the activity of D519VE665VE1984V as measured by two-stage assay was significantly reduced. Since Asp519 is located at the A1 and A2 interface while Glu665 and Glu1984 are located at the A2 and A3 interface, it is believed that the tendency for elevated specific activity for the Group A mutations compared with Group B may result from more favorable interactions at the A1-A2 junction that affect conformation and preserve the active cofactor form.

FIG. 9 shows the summary of the results from factor VIII thermal stability experiments conducted at 55° C. The rate values obtained for the combination mutants were compared with rate values from the best single mutant in that particular combination using data for the single mutations obtained from Example 5 (FIG. 5A). FIG. 9 also shows the actual value for the rate of factor VIII decay (see also Table 4). The degree of reduction of the relative decay rates appear to relate to the enhancement observed for the combination of mutations. In Group A, mutants D519AE665A, D519AD665V, and D519VE665V showed significant enhancement in stability (reductions in decay rates) and most of the mutants also maintained an absolute decay rate that was ~50% the WT value. On the other hand, the relative rates for two of the Group B mutants were somewhat increased (E665AE1984A and E665AE1984V) as compared with the better single mutation. In Group C, mutants D519AE665VE1984A and D519VE665VE1984A showed no significant change in the rate while the rate value for D519VE665VE1984V was slightly increased.

Interestingly, the enhancement of stability observed for the combination of mutations was more easily observed for the factor VIIIa forms (FIG. 10). To increase the sensitivity of the factor VIIIa decay assay for highly stable mutants, a lower concentration of factor VIIIa (1.5 µM) for the incubation than was employed in the preceding Examples. Large stability enhancements of up to ~4 fold compared to the single mutants were observed for all Group A mutants. Actual values for the factor VIIIa decay rates of D519VE665V and D519VE1984A were 14 and 12% of that of WT factor VIII, respectively (FIG. 10 and Table 4). Group B mutants in general yielded poorer results when compared with the better individual mutation in the pairing, with E665AE1984A and E665AF1984V, showing ~2.2 and ~2.7 fold increases, respectively, in relative decay rate values. The triple mutations (Group C) showed the largest factor VIIIa stability enhancements with maximal stability observed for D519VE665VE1984A, which showed a decay rate that was ~10% of WT (FIG. 10 and Table 4).

A thrombin generation assay was performed on selected mutants and the results are shown in FIGS. 11A-B. There was no significant improvement in thrombin generation profiles when the single mutants were tested using a final concentration of 1 nM factor VIII (see Materials & Methods, and Example 4 above). To better compare the more stable factor VIII mutants, a lower factor VIII concentration (0.2 nM) was used. Results from this analysis showed that D519VE665V possessed an ~20% reduction in the lag time and peak time as well as ~2.3 fold increase in the peak height and ~1.5 fold increase in endogenous thrombin potential (ETP) compared to WT factor VIII (FIGS. 11A-B). Although the lag time and peak time values for D519AE665V, D519VE1984A, and D519VE665VE1984A were not changed significantly relative to WT, the peak height and ETP values were significantly greater than WT (~20% to 70%). Overall, these results indicate that the selected four combination mutants all possessing enhanced factor VIIIa stability showed improved thrombin generation profiles. This observation indicates that these mutants may have greater capacity for increased thrombin generation per unit concentration factor VIII in a physiologic situation.

Example 9

Ala or Val Mutants at Asp519, Glu665, and Glu1984 in Combination with High Specific Activity Glu113Ala (E113A) Mutation The E113A mutation is known to enhance factor VIII specific activity as judged by a one-stage clotting assay (U.S. patent application Ser. No. 10/581,471 to Fay et al.; Wakabayashi et al., "A Glut 13Ala Mutation within a Factor VIII Ca(2+)-Binding Site Enhances Cofactor Interactions in Factor Xase," *Biochemistry* 44:10298-10304 (2005), each of which is hereby incorporated by reference in its entirety). Since the generation of factor VIII with both high stability and

TABLE 4

Factor VIII and VIIIa Decay Rates and Activity Values for Combination Mutants

| | Decay rates (min$^{-1}$) | | Specific Activity | |
|---|---|---|---|---|
| | Factor VIII | Factor VIIIa | One-stage assay | Two-stage assay |
| WT | 0.0473 (1.00[a]) | 0.1400 (1.00) | 4.77[b] (1.00) | 44.5[c] (1.00) |
| D519AE665A | 0.0255 (0.54) | 0.0352 (0.25) | 6.40 (1.34) | 36.6 (0.82) |
| D519AE665V | 0.0213 (0.45) | 0.0222 (0.16) | 3.81 (0.80) | 47.6 (1.07) |
| D519AE1984A | 0.0250 (0.53) | 0.0266 (0.19) | 4.42 (0.93) | 36.0 (0.81) |
| D519AE1984V | 0.0247 (0.53) | 0.0319 (0.23) | 4.55 (0.95) | 47.9 (1.08) |
| D519VE665V | 0.0238 (0.51) | 0.0198 (0.14) | 6.65 (1.39) | 47.5 (1.07) |
| D519VE1984A | 0.0256 (0.54) | 0.0168 (0.12) | 6.08 (1.27) | 43.0 (0.97) |
| D519VE1984V | 0.0259 (0.55) | 0.0262 (0.19) | 8.43 (1.77) | 50.5 (1.13) |
| E665AE1984A | 0.0324 (0.69) | 0.1302 (0.93) | 2.10 (0.44) | 21.5 (0.48) |
| E665AE1984V | 0.0348 (0.74) | 0.1267 (0.90) | 3.89 (0.82) | 30.2 (0.68) |
| E665VE1984A | 0.0232 (0.49) | 0.0360 (0.26) | 5.76 (1.21) | 39.8 (0.89) |
| E665VE1984V | 0.0220 (0.47) | 0.0671 (0.48) | 2.50 (0.53) | 37.9 (0.85) |
| D519AE665VE1984A | 0.0246 (0.52) | 0.0235 (0.17) | 4.97 (1.04) | 46.3 (1.04) |
| D519VE665VE1984A | 0.0254 (0.54) | 0.0142 (0.10) | 4.29 (0.90) | 37.9 (0.85) |
| D519VE665VE1984V | 0.0307 (0.65) | 0.0227 (0.16) | 7.86 (1.65) | 17.4 (0.39) |
| D159A | 0.0336[d] (0.71) | 0.0898 (0.64) | | |
| D519V | 0.0262[d] (0.56) | 0.0836 (0.60) | | |
| E665A | 0.0359[d] (0.76) | 0.0834 (0.60) | | |
| E665V | 0.0309[d] (0.66) | 0.0395 (0.28) | | |
| E1984A | 0.0240[d] (0.51) | 0.0574 (0.41) | | |
| E1984V | 0.0211[d] (0.45) | 0.0471 (0.34) | | |

Standard deviations for rate decay values are estimated based on least squares curve-fitting and are within ~10% of mean values.
[a] values in parentheses are relative to wild type.
[b] Unit/µg.
[c] nM factor Xa generated/min/nM factor VIII.
[d] Data reproduced from Table 3 above.

high specific activity represents a unique class of reagents for potential therapeutic application in the treatment of hemophilia, the effect of combined mutation of E113A with the high stability mutants described in the preceding Examples was analyzed.

Ala or Val mutants at Asp519, Glu665, and Glu1984 were prepared in combination with the E113A mutation using the same procedures described in the Materials and Methods. These double mutants (amino acids are identified using the single letter code) include: E113AD519A, E113AD519V, E113AE665A, E113AE665V, and E113AE1984V.

Specific activity values determined using the one-stage assay for the combined mutants were ~2 to ~3.3 fold higher than WT factor VIII while keeping the normal level of activity by two-stage assay. These results indicate that mutations at Asp519, Glu665, or Glu1984 did not adversely affect the activity enhancement observed for the E113A mutation (FIG. 12A). In addition, the factor VIII and VIIIa decay rates of E113A in combination with the high stability mutants were not significantly different from the value of each original single high stability mutant (see FIGS. 5B-C; Table 5), suggesting that the E113A mutation did not affect the enhanced stability parameters for these mutants.

TABLE 5

Factor VIII and VIIIa Decay Rates and Activity Values

| | Decay rates (min$^{-1}$) | | Specific Activity | |
|---|---|---|---|---|
| | Factor VIII | Factor VIIIa | One-stage assay | Two-stage assay |
| WT | 0.0473 (1.00$^a$) | 0.1400 (1.00) | 4.77$^b$ (1.00) | 44.5$^c$ (1.00) |
| E113AD519A | 0.0471 (0.63) | 0.0748 (0.53) | 14.3 (2.99) | 37.3 (0.84) |
| E113AD519V | 0.0297 (0.57) | 0.0495 (0.35) | 10.3 (2.16) | 40.9 (0.92) |
| E113AE665A | 0.0270 (0.61) | 0.0754 (0.54) | 15.7 (3.29) | 45.4 (1.02) |
| E113AE665V | 0.0286 (0.59) | 0.0333 (0.24) | 9.6 (2.02) | 44.5 (1.00) |
| E113AE1984V | 0.0278 (0.53) | 0.0567 (0.40) | 13.4 (2.81) | 48.5 (0.52) |
| D519A | 0.0336$^d$ (0.71) | 0.0898 (0.64) | | |
| D519V | 0.0262$^d$ (0.56) | 0.0836 (0.60) | | |
| E665A | 0.0359$^d$ (0.76) | 0.0834 (0.60) | | |
| E665V | 0.0309$^d$ (0.66) | 0.0395 (0.28) | | |
| E1984A | 0.0240$^d$ (0.51) | 0.0574 (0.41) | | |
| E1984V | 0.0211$^d$ (0.45) | 0.0471 (0.34) | | |

Standard deviations for rate decay values are estimated based on least squares curve-fitting and are within ~10% of mean values.
$^a$values in parentheses are relative to wild type.
$^b$Unit/µg.
$^c$nM factor Xa generated/min/nM factor VIII.
$^d$Data reproduced from Table 3 above.

From the foregoing results, the mutation of E113A can be combined with any of the currently described increased stability mutations for the purpose of generating a recombinant factor VIII characterized by both increased specific activity and enhanced factor VIII/factor VIIIa stability. This includes the combination of E113A (or other suitable E113 substitutions as described in U.S. patent application Ser. No. 10/581,471 to Fay et al., which is hereby incorporated by reference in its entirety) with single or multiple stability-enhanced mutants of the type described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A recombinant factor VIII comprising one or more mutations that result in enhanced stability of both factor VIII and factor VIIIa, wherein the one or more mutations are selected from the group consisting of substitution of a Glu residue with a hydrophobic amino acid residue at a position corresponding to amino acid 287, 665, and/or 1984 of SEQ ID NO: 2, substitution of an Asp residue with a hydrophobic amino acid residue at a position corresponding to amino acid 302 and/or 519 of SEQ ID NO: 2, and combinations of two or more of said substitutions, and wherein the position of the substitution or substitutions of said recombinant factor VIII aligns with amino acids 287, 302, 519, 665, and/or 1984 of SEQ ID NO: 2 upon alignment of the amino acid sequence of the recombinant factor VIII with the amino acid sequence of SEQ ID NO: 2.

2. The recombinant factor VIII according to claim 1, wherein the hydrophobic amino acid residue is one of Ala, Val, Ile, Leu, Met, Phe, or Trp.

3. The recombinant factor VIII according to claim 1, wherein the one or more mutations is an Asp→Ala substitution at a position corresponding to amino acid 302 of SEQ ID NO: 2.

4. The recombinant factor VIII according to claim 1, wherein the one or more mutations is a Glu→Ala substitution at a position corresponding to amino acid 287 of SEQ ID NO: 2.

5. The recombinant factor VIII according to claim 1, wherein the one or more mutations is a Glu→Ala or Glu→Val substitution at a position corresponding to amino acid 665 of SEQ ID NO: 2.

6. The recombinant factor VIII according to claim 1, wherein the one or more mutations is a Asp→Ala or Asp→Val substitution at a position corresponding to amino acid 519 of SEQ ID NO: 2.

7. The recombinant factor VIII according to claim 1, wherein the one or more mutations is a Glu→Ala or Glu→Val substitution at a position corresponding to amino acid 1984 of SEQ ID NO: 2.

8. The recombinant factor VIII according to claim 1, wherein the one or more mutations is a combination of two or more of said substitutions.

9. The recombinant factor VIII according to claim 8, wherein the two or more substitutions comprise:
   (i) Asp→Val substitution at a position corresponding to amino acid 519 of SEQ ID NO: 2 and Glu→Val substitution at a position corresponding to amino acid 665 of SEQ ID NO: 2;
   (ii) Asp→Ala substitution at a position corresponding to amino acid 519 of SEQ ID NO: 2 and Glu→Val substitution at a position corresponding to amino acid 665 of SEQ ID NO: 2;
   (iii) Asp→Val substitution at a position corresponding to amino acid 519 of SEQ ID NO: 2 and Glu→Ala substitution at a position corresponding to amino acid 1984 of SEQ ID NO: 2;
   (iv) Glu→Val substitution at a position corresponding to amino acid 665 of SEQ ID NO: 2 and Glu→Ala substitution at a position corresponding to amino acid 1984 of SEQ ID NO: 2;
   (v) Glu→Ala substitution at a position corresponding to amino acid 665 of SEQ ID NO: 2 and Glu→Val substitution at a position corresponding to amino acid 1984 of SEQ ID NO: 2;
   (vi) Asp→Ala substitution at a position corresponding to amino acid 519 of SEQ ID NO: 2, Glu→Val substitution at a position corresponding to amino acid 665 of SEQ ID NO: 2, and Glu→Ala substitution at a position corresponding to amino acid 1984 of SEQ ID NO: 2;
   (vii) Asp→Val substitution at a position corresponding to amino acid 519 of SEQ ID NO: 2, Glu→Val substitution at a position corresponding to amino acid 665 of SEQ ID NO: 2, and Glu→Ala substitution at a position corresponding to amino acid 1984 of SEQ ID NO: 2; or
   (viii) Asp→Val substitution at a position corresponding to amino acid 519 of SEQ ID NO: 2, Glu→Val substitution at a position corresponding to amino acid 665 of SEQ ID NO: 2, and Glu→Val substitution at a position corresponding to amino acid 1984 of SEQ ID NO: 2.

10. The recombinant factor VIII according to claim 1, wherein the recombinant factor VIII consists of domains A1, A2, A3, C1, and C2, or portions thereof.

11. The recombinant factor VIII according to claim 1, wherein the recombinant factor VIII comprises one or more domains, or portions thereof, from human factor VIII and one or more domains, or portions thereof, from a non-human mammalian factor VIII.

12. The recombinant factor VIII according to claim 1, wherein the recombinant factor VIII is substantially pure.

13. The recombinant factor VIII according to claim 1 wherein the recombinant factor VIII further comprises one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof; and (v) a modified calcium-binding site that improves specific activity of the recombinant factor VIIIa.

14. The recombinant factor VIII according to claim 1 further comprising substitution of a Glu residue at a position corresponding to amino acid 113 of SEQ ID NO: 2 wherein the position of the Glu substitution of said recombinant factor VIII aligns with amino acid 113 of SEQ ID NO: 2 upon alignment of the amino acid sequence of the recombinant factor VIII with the amino acid sequence of SEQ ID NO: 2.

15. The recombinant factor VIII according to claim 14, wherein the recombinant factor VIII comprises:
   (i) Glu→Ala substitution at a position corresponding to amino acid 113 of SEQ ID NO: 2 and Asp→Ala substitution at a position corresponding to amino acid 519 of SEQ ID NO: 2;
   (ii) Glu→Ala substitution at a position corresponding to amino acid 113 of SEQ ID NO: 2 and Asp→Val substitution at a position corresponding to amino acid 519 of SEQ ID NO: 2;
   (iii) Glu→Ala substitution at a position corresponding to amino acid 113 of SEQ ID NO: 2 and Glu→Ala substitution at a position corresponding to amino acid 665 of SEQ ID NO: 2;
   (iv) Glu→Ala substitution at a position corresponding to amino acid 113 of SEQ ID NO: 2 and Glu→Val substitution at a position corresponding to amino acid 665 of SEQ ID NO: 2; or
   (v) Glu→Ala substitution at a position corresponding to amino acid 113 of SEQ ID NO: 2 and Glu→Val substitution at a position corresponding to amino acid 1984 of SEQ ID NO: 2.

16. A pharmaceutical composition comprising the recombinant factor VIII according to claim 1.

17. The pharmaceutical composition according to claim 16 further comprising a stabilizer.

18. The pharmaceutical composition according to claim 16 further comprising a delivery vehicle.

19. The pharmaceutical composition according to claim 16 further comprising a pharmaceutically acceptable carrier.

20. A method of treating an animal for hemophilia A, the method comprising:
   administering to an animal exhibiting hemophilia A an effective amount of the recombinant factor VIII according to claim 1, whereby the animal exhibits effective blood clotting following vascular injury.

21. The method according to claim 20, wherein the effective amount comprises between about 10 to about 50 units/kg body weight of the animal.

22. The method according to claim 20 wherein the animal is a mammal.

23. The method according to claim 20 wherein the animal is selected from the group consisting of human, rat, mouse, guinea pig, dog, cat, monkey, chimpanzee, orangutan, cow, horse, sheep, pig, goat, rabbit, and chicken.

24. The method according to claim 20 further comprising periodically repeating said administering.

25. A recombinant factor VIII comprising one or more mutations that result in enhanced stability of both factor VIII and factor VIIIa, wherein the one or more mutations is a substitution of a charged amino acid residue with a hydrophobic residue at one or more amino acid positions selected from the group consisting of 287, 302, 519, 665, and 1984 of SEQ ID NO: 2.

26. The recombinant factor VIII according to claim 25, wherein the hydrophobic amino acid residue is one of Ala, Val, Ile, Leu, Met, Phe, or Trp.

27. The recombinant factor VIII according to claim 25, wherein the substitution at position 302 of SEQ ID NO: 2 is Asp→Ala.

28. The recombinant factor VIII according to claim 25, wherein the substitution at position 287 of SEQ ID NO: 2 is Glu→Ala.

29. The recombinant factor VIII according to claim 25, wherein the substitution at position 665 of SEQ ID NO: 2 is Glu→Ala or Glu→Val.

30. The recombinant factor VIII according to claim 25, wherein the substitution at position 519 of SEQ ID NO: 2 is Asp→Ala or Asp→Val.

31. The recombinant factor VIII according to claim 25, wherein the substitution at position 1984 of SEQ ID NO: 2 is Glu→Ala or Glu→Val.

32. The recombinant factor VIII according to claim 25, wherein the one or more mutations is a combination of two or more of said substitutions.

33. The recombinant factor VIII according to claim 32, wherein the two or more substitutions are:
   (i) Asp→Val substitution at position 519 of SEQ ID NO: 2 and Glu→Val substitution at position 665 of SEQ ID NO: 2;
   (ii) Asp→Ala substitution at position 519 of SEQ ID NO: 2 and Glu→Val substitution at position 665 of SEQ ID NO: 2;
   (iii) Asp→Val substitution at position 519 of SEQ ID NO: 2 and Glu→Ala substitution at position 1984 of SEQ ID NO: 2;
   (iv) Glu→Val substitution at position 665 of SEQ ID NO: 2 and Glu→Ala substitution at position 1984 of SEQ ID NO: 2;
   (v) Glu→Ala substitution at position 665 of SEQ ID NO: 2 and Glu→Val substitution at position 1984 of SEQ ID NO: 2;
   (vi) Asp→Ala substitution at position 519 of SEQ ID NO: 2, Glu→Val substitution at position 665 of SEQ ID NO: 2, and Glu→Ala substitution at position 1984 of SEQ ID NO: 2;
   (vii) Asp→Val substitution at position 519 of SEQ ID NO: 2, Glu→Val substitution at position 665 of SEQ ID NO: 2, and Glu→Ala substitution at position 1984 of SEQ ID NO: 2; or
   (viii) Asp→Val substitution at position 519 of SEQ ID NO: 2, Glu→Val substitution at position 665 of SEQ ID NO: 2, and Glu→Val substitution at position 1984 of SEQ ID NO: 2.

34. The recombinant factor VIII according to claim 25, wherein the recombinant factor VIII consists of domains A1, A2, A3, C1, and C2, or portions thereof.

35. The recombinant factor VIII according to claim 25, wherein the recombinant factor VIII is substantially pure.

36. The recombinant factor VIII according to claim 25 wherein the recombinant factor VIII further comprises one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof; and (v) a modified calcium-binding site that improves specific activity of the recombinant factor VIIIa.

37. The recombinant factor VIII according to claim 25 further comprising substitution of a Glu residue at position 113 of SEQ ID NO: 2.

38. The recombinant factor VIII according to claim 37, wherein the recombinant factor VIII comprises:
   (i) Glu→Ala substitution at position 113 of SEQ ID NO: 2 and Asp→Ala substitution at position 519 of SEQ ID NO: 2;
   (ii) Glu→Ala substitution at position 113 of SEQ ID NO: 2 and Asp→Val substitution at position 519 of SEQ ID NO: 2;
   (iii) Glu→Ala substitution at position 113 of SEQ ID NO: 2 and Glu→Ala substitution at position 665 of SEQ ID NO: 2;
   (iv) Glu→Ala substitution at position 113 of SEQ ID NO: 2 and Glu→Val substitution at position 665 of SEQ ID NO: 2; or (v) Glu→Ala substitution at position 113 of SEQ ID NO: 2 and Glu→Val substitution at position 1984 of SEQ ID NO: 2.

39. A pharmaceutical composition comprising the recombinant factor VIII according to claim 25.

40. The pharmaceutical composition according to claim 39 further comprising a stabilizer.

41. The pharmaceutical composition according to claim 39 further comprising a delivery vehicle.

42. A method of treating an animal for hemophilia A, the method comprising:
   administering to an animal exhibiting hemophilia A an effective amount of the recombinant factor VIII according to claim 25, whereby the animal exhibits effective blood clotting following vascular injury.

43. The method according to claim 42, wherein the effective amount comprises between about 10 to about 50 units/kg body weight of the animal.

44. The method according to claim 42 wherein the animal is a mammal.

45. The method according to claim 42 wherein the animal is selected from the group consisting of human, rat, mouse, guinea pig, dog, cat, monkey, chimpanzee, orangutan, cow, horse, sheep, pig, goat, rabbit, and chicken.

46. The method according to claim 42 further comprising periodically repeating said administering.

\* \* \* \* \*